United States Patent
Al-Ali et al.

(10) Patent No.: US 11,095,068 B2
(45) Date of Patent: Aug. 17, 2021

(54) WATER RESISTANT CONNECTOR FOR NONINVASIVE PATIENT MONITOR

(71) Applicant: Masimo Corporation, Irvine, CA (US)

(72) Inventors: Ammar Al-Ali, San Juan Capistrano, CA (US); Kevin Forrest, Rancho Santa Margarita, CA (US); Yassir Kamel Abdul-Hafiz, Irvine, CA (US)

(73) Assignee: MASIMO CORPORATION, Irvine, CA (US)

( * ) Notice: Subject to any disclaimer, the term of this patent is extended or adjusted under 35 U.S.C. 154(b) by 0 days.

(21) Appl. No.: 16/858,421

(22) Filed: Apr. 24, 2020

(65) Prior Publication Data
US 2021/0083421 A1    Mar. 18, 2021

Related U.S. Application Data

(63) Continuation of application No. 16/102,456, filed on Aug. 13, 2018, now Pat. No. 10,637,181.

(60) Provisional application No. 62/545,884, filed on Aug. 15, 2017, provisional application No. 62/545,877, filed on Aug. 15, 2017.

(51) Int. Cl.
*H01R 13/52*       (2006.01)
*A61B 5/30*        (2021.01)

(52) U.S. Cl.
CPC ......... *H01R 13/5224* (2013.01); *A61B 5/303* (2021.01); *H01R 13/5205* (2013.01); *H01R 13/5219* (2013.01); *A61B 2562/227* (2013.01); *A61B 2562/247* (2013.01); *H01R 13/5202* (2013.01); *H01R 2201/12* (2013.01)

(58) Field of Classification Search
CPC ................ H01R 13/5224; H01R 13/5205

USPC ................................... 281/281, 660
See application file for complete search history.

(56) References Cited

U.S. PATENT DOCUMENTS

| | | |
|---|---|---|
| 3,328,744 A | 6/1967 | Fiske |
| 3,945,701 A | 3/1976 | Boeke et al. |
| D244,297 S | 5/1977 | Stropkay |
| 4,445,742 A | 5/1984 | Fullam |
| 4,960,128 A | 10/1990 | Gordon et al. |
| 4,964,408 A | 10/1990 | Hink et al. |
| 5,041,187 A | 8/1991 | Hink et al. |
| 5,069,213 A | 12/1991 | Hink et al. |

(Continued)

FOREIGN PATENT DOCUMENTS

WO    WO 2019/036379    2/2019

OTHER PUBLICATIONS

International Search Report and Written Opinion for PCT Application No. PCT/US2018/046544 dated Jan. 10, 2019 in 19 pages.

(Continued)

*Primary Examiner* — Neil Abrams
(74) *Attorney, Agent, or Firm* — Knobbe, Martens, Olson & Bear, LLP

(57) ABSTRACT

Systems and methods are provided for water resistant connectors. A male connector includes a rib or a draft angle that creates a seal when engaged with a female connector. A male connector includes an overmold that includes or is made of a thermoplastic elastomer. Male or female connectors include molds that include or are made of a thermoplastic polymer, such as polypropylene. A female connector includes spring contacts that fit within individual pockets of the female connector.

20 Claims, 57 Drawing Sheets

(56) References Cited

U.S. PATENT DOCUMENTS

| | | |
|---|---|---|
| 5,163,438 A | 11/1992 | Gordon et al. |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| 5,401,181 A | 3/1995 | Wilson |
| D359,546 S | 6/1995 | Savage et al. |
| 5,431,170 A | 7/1995 | Mathews |
| 5,436,499 A | 7/1995 | Namavar et al. |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,671,914 A | 9/1997 | Kalkhoran et al. |
| 5,685,299 A | 11/1997 | Diab et al. |
| 5,726,440 A | 3/1998 | Kalkhoran et al. |
| D393,830 S | 4/1998 | Tobler et al. |
| 5,743,262 A | 4/1998 | Lepper, Jr. et al. |
| 5,747,806 A | 5/1998 | Khalil et al. |
| 5,750,994 A | 5/1998 | Schlager |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,987,343 A | 11/1999 | Kinast |
| 5,995,855 A | 11/1999 | Kiani et al. |
| 5,997,343 A | 12/1999 | Mills et al. |
| 6,002,952 A | 12/1999 | Diab et al. |
| 6,010,937 A | 1/2000 | Karam et al. |
| 6,011,986 A | 1/2000 | Diab et al. |
| 6,027,452 A | 2/2000 | Flaherty et al. |
| 6,036,642 A | 3/2000 | Diab et al. |
| 6,040,578 A | 3/2000 | Malin et al. |
| 6,045,509 A | 4/2000 | Caro et al. |
| 6,066,204 A | 5/2000 | Haven |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,115,673 A | 9/2000 | Malin et al. |
| 6,124,597 A | 9/2000 | Shehada et al. |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,255,708 B1 | 7/2001 | Sudharsanan et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,896 B1 | 9/2001 | Tobler et al. |
| 6,301,493 B1 | 10/2001 | Marro et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,334,781 B1 | 1/2002 | Nishio et al. |
| 6,343,224 B1 | 1/2002 | Parker |
| 6,349,228 B1 | 2/2002 | Kiani et al. |
| D454,875 S | 3/2002 | McDowell et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,487,429 B2 | 11/2002 | Hockersmith et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,534,012 B1 | 3/2003 | Hazen et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali |
| D485,239 S | 1/2004 | Whalin et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |

(56) References Cited

U.S. PATENT DOCUMENTS

| | | |
|---|---|---|
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,738,652 B2 | 5/2004 | Mattu et al. |
| 6,745,060 B2 | 6/2004 | Diab et al. |
| 6,760,607 B2 | 7/2004 | Al-Ali |
| D494,597 S | 8/2004 | Lucas et al. |
| 6,770,028 B1 | 8/2004 | Ali et al. |
| 6,771,994 B2 | 8/2004 | Kiani et al. |
| 6,788,965 B2 | 9/2004 | Ruchti et al. |
| 6,792,300 B1 | 9/2004 | Diab et al. |
| 6,813,511 B2 | 11/2004 | Diab et al. |
| 6,816,241 B2 | 11/2004 | Grubisic |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,876,931 B2 | 4/2005 | Lorenz et al. |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,956,649 B2 | 10/2005 | Acosta et al. |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,990,364 B2 | 1/2006 | Ruchti et al. |
| 6,993,371 B2 | 1/2006 | Kiani et al. |
| 6,996,427 B2 | 2/2006 | Ali et al. |
| 6,998,247 B2 | 2/2006 | Monfre et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,048,687 B1 | 5/2006 | Reuss et al. |
| 7,067,893 B2 | 6/2006 | Mills et al. |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,132,641 B2 | 11/2006 | Schulz et al. |
| 7,133,710 B2 | 11/2006 | Acosta et al. |
| 7,134,884 B2 | 11/2006 | Wang et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab et al. |
| 7,215,986 B2 | 5/2007 | Diab et al. |
| 7,221,971 B2 | 5/2007 | Diab et al. |
| 7,225,006 B2 | 5/2007 | Al-Ali et al. |
| 7,225,007 B2 | 5/2007 | Al-Ali et al. |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali et al. |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali et al. |
| 7,275,949 B1 | 10/2007 | Speaker, IV |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,390,210 B2 | 6/2008 | Corona et al. |
| 7,395,158 B2 | 7/2008 | Monfre et al. |
| 7,415,297 B2 | 8/2008 | Al-Ali et al. |
| D577,340 S | 9/2008 | Henderson |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| 7,526,328 B2 | 4/2009 | Diab et al. |
| D592,507 S | 5/2009 | Wachman et al. |
| 7,530,942 B1 | 5/2009 | Diab |
| 7,530,949 B2 | 5/2009 | Al Ali et al. |
| 7,530,955 B2 | 5/2009 | Diab et al. |
| 7,553,191 B2 | 6/2009 | Su et al. |
| 7,563,110 B2 | 7/2009 | Al-Ali et al. |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,614,911 B2 | 11/2009 | Hsieh et al. |
| 7,618,375 B2 | 11/2009 | Flaherty et al. |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |

(56) References Cited

U.S. PATENT DOCUMENTS

| | | |
|---|---|---|
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| 8,079,846 B1 | 12/2011 | Cookson |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,532 B2 | 7/2012 | Davis |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,280,473 B2 | 10/2012 | Al-Ali |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-Ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellott et al. |
| 8,471,713 B2 | 6/2013 | Poeze et al. |
| 8,473,020 B2 | 6/2013 | Kiani et al. |
| 8,480,436 B2 | 7/2013 | Chang |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,610 B2 | 9/2013 | Kuster |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,602,825 B2 | 12/2013 | Chen |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| D699,359 S | 2/2014 | Lindekugel et al. |
| D699,686 S | 2/2014 | Chen et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |

(56) References Cited

U.S. PATENT DOCUMENTS

| | | |
|---|---|---|
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,763,909 B2 | 7/2014 | Reed et al. |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,784,123 B1 * | 7/2014 | Leiba ................ H01R 24/28 439/218 |
| 8,788,003 B2 | 7/2014 | Schurman et al. |
| 8,790,268 B2 | 7/2014 | Al-Ali |
| 8,794,981 B1 | 8/2014 | Rodriguez et al. |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,500 B2 | 11/2014 | Gao et al. |
| 8,888,535 B2 | 11/2014 | Knight et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,125,563 B2 | 9/2015 | Abrams et al. |
| 9,130,301 B2 | 9/2015 | Lu |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,172,176 B2 | 10/2015 | Chen et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,263,829 B2 | 2/2016 | Wu et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-Ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| D774,510 S | 12/2016 | Rotsaert |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |

(56) References Cited

U.S. PATENT DOCUMENTS

| | | | |
|---|---|---|---|
| 9,591,975 B2 | 3/2017 | Dalvi et al. | |
| 9,622,692 B2 | 4/2017 | Lamego et al. | |
| 9,622,693 B2 | 4/2017 | Diab | |
| D788,312 S | 5/2017 | Al-Ali et al. | |
| 9,636,055 B2 | 5/2017 | Al Ali et al. | |
| 9,636,056 B2 | 5/2017 | Al-Ali | |
| 9,649,054 B2 | 5/2017 | Lamego et al. | |
| 9,662,052 B2 | 5/2017 | Al-Ali et al. | |
| 9,668,679 B2 | 6/2017 | Schurman et al. | |
| 9,668,680 B2 | 6/2017 | Bruinsma et al. | |
| 9,668,703 B2 | 6/2017 | Al-Ali | |
| 9,675,286 B2 | 6/2017 | Diab | |
| 9,687,160 B2 | 6/2017 | Kiani | |
| 9,693,719 B2 | 7/2017 | Al-Ali et al. | |
| 9,693,737 B2 | 7/2017 | Al-Ali | |
| 9,697,928 B2 | 7/2017 | Al-Ali et al. | |
| 9,717,425 B2 | 8/2017 | Kiani et al. | |
| 9,717,458 B2 | 8/2017 | Lamego et al. | |
| 9,724,016 B1 | 8/2017 | Al-Ali et al. | |
| 9,724,024 B2 | 8/2017 | Al-Ali | |
| 9,724,025 B1 | 8/2017 | Kiani et al. | |
| 9,730,640 B2 | 8/2017 | Diab et al. | |
| 9,743,887 B2 | 8/2017 | Al-Ali et al. | |
| 9,749,232 B2 | 8/2017 | Sampath et al. | |
| 9,750,442 B2 | 9/2017 | Olsen | |
| 9,750,443 B2 | 9/2017 | Smith et al. | |
| 9,750,461 B1 | 9/2017 | Telfort | |
| 9,775,545 B2 | 10/2017 | Al-Ali et al. | |
| 9,775,546 B2 | 10/2017 | Diab et al. | |
| 9,775,570 B2 | 10/2017 | Al-Ali | |
| 9,778,079 B1 | 10/2017 | Al-Ali et al. | |
| 9,782,077 B2 | 10/2017 | Lamego et al. | |
| 9,782,110 B2 | 10/2017 | Kiani | |
| 9,785,204 B1 | 10/2017 | Miller et al. | |
| 9,787,568 B2 | 10/2017 | Lamego et al. | |
| 9,788,735 B2 | 10/2017 | Al-Ali | |
| 9,788,768 B2 | 10/2017 | Al-Ali et al. | |
| 9,795,300 B2 | 10/2017 | Al-Ali | |
| 9,795,310 B2 | 10/2017 | Al-Ali | |
| 9,795,358 B2 | 10/2017 | Telfort et al. | |
| 9,795,739 B2 | 10/2017 | Al-Ali et al. | |
| 9,801,556 B2 | 10/2017 | Kiani | |
| 9,801,588 B2 | 10/2017 | Weber et al. | |
| 9,808,188 B1 | 11/2017 | Perea et al. | |
| 9,814,418 B2 | 11/2017 | Weber et al. | |
| 9,820,691 B2 | 11/2017 | Kiani | |
| D804,477 S | 12/2017 | Harris et al. | |
| D804,478 S | 12/2017 | Harris et al. | |
| D804,479 S | 12/2017 | Harris et al. | |
| 9,833,152 B2 | 12/2017 | Kiani et al. | |
| 9,833,180 B2 | 12/2017 | Shakespeare et al. | |
| 9,839,379 B2 | 12/2017 | Al-Ali et al. | |
| 9,839,381 B1 | 12/2017 | Weber et al. | |
| 9,843,137 B2 * | 12/2017 | McCracken | H01R 13/6315 |
| 9,847,002 B2 | 12/2017 | Kiani et al. | |
| 9,847,749 B2 | 12/2017 | Kiani et al. | |
| 9,848,800 B1 | 12/2017 | Lee et al. | |
| 9,848,806 B2 | 12/2017 | Al-Ali | |
| 9,848,807 B2 | 12/2017 | Lamego | |
| 9,861,298 B2 | 1/2018 | Eckerbom et al. | |
| 9,861,304 B2 | 1/2018 | Al-Ali et al. | |
| 9,861,305 B1 | 1/2018 | Weber et al. | |
| 9,867,578 B2 | 1/2018 | Al-Ali et al. | |
| 9,872,623 B2 | 1/2018 | Al-Ali | |
| 9,876,320 B2 | 1/2018 | Coverston et al. | |
| 9,877,650 B2 | 1/2018 | Muhsin et al. | |
| 9,877,686 B2 | 1/2018 | Al-Ali et al. | |
| 9,891,079 B2 | 2/2018 | Dalvi | |
| 9,895,107 B2 | 2/2018 | Al-Ali et al. | |
| 9,913,617 B2 | 3/2018 | Al-Ali et al. | |
| 9,924,893 B2 | 3/2018 | Schurman et al. | |
| 9,924,897 B1 | 3/2018 | Abdul-Hafiz | |
| 9,936,917 B2 | 4/2018 | Poeze et al. | |
| 9,943,269 B2 | 4/2018 | Muhsin et al. | |
| 9,949,676 B2 | 4/2018 | Al-Ali | |
| 9,955,937 B2 | 5/2018 | Telfort | |
| 9,965,946 B2 | 5/2018 | Al-Ali et al. | |
| 9,979,139 B2 | 5/2018 | Golko et al. | |
| 9,980,667 B2 | 5/2018 | Kiani et al. | |
| D820,865 S | 6/2018 | Muhsin et al. | |
| 9,986,919 B2 | 6/2018 | Lamego et al. | |
| 9,986,952 B2 | 6/2018 | Dalvi et al. | |
| 9,989,560 B2 | 6/2018 | Poeze et al. | |
| 9,991,640 B2 | 6/2018 | Tziviskos et al. | |
| 9,993,207 B2 | 6/2018 | Al-Ali et al. | |
| 10,007,758 B2 | 6/2018 | Al-Ali et al. | |
| D822,215 S | 7/2018 | Al-Ali et al. | |
| D822,216 S | 7/2018 | Barker et al. | |
| D824,332 S | 7/2018 | Ackerman | |
| 10,010,276 B2 | 7/2018 | Al-Ali et al. | |
| 10,032,002 B2 | 7/2018 | Kiani et al. | |
| 10,039,482 B2 | 8/2018 | Al-Ali et al. | |
| 10,052,037 B2 | 8/2018 | Kinast et al. | |
| 10,058,275 B2 | 8/2018 | Al-Ali et al. | |
| 10,064,562 B2 | 9/2018 | Al-Ali | |
| 10,086,138 B1 | 10/2018 | Novak, Jr. | |
| 10,092,200 B2 | 10/2018 | Al-Ali et al. | |
| 10,092,249 B2 | 10/2018 | Kiani et al. | |
| 10,098,550 B2 | 10/2018 | Al-Ali et al. | |
| 10,098,591 B2 | 10/2018 | Al-Ali et al. | |
| 10,098,610 B2 | 10/2018 | Al-Ali et al. | |
| 10,111,591 B2 | 10/2018 | Dyell et al. | |
| D833,624 S | 11/2018 | Dejong et al. | |
| 10,123,726 B2 | 11/2018 | Al-Ali et al. | |
| 10,123,729 B2 | 11/2018 | Dyell et al. | |
| 10,130,289 B2 | 11/2018 | Al-Ali et al. | |
| 10,130,291 B2 | 11/2018 | Schurman et al. | |
| D835,282 S | 12/2018 | Barker et al. | |
| D835,283 S | 12/2018 | Barker et al. | |
| D835,284 S | 12/2018 | Barker et al. | |
| D835,285 S | 12/2018 | Barker et al. | |
| 10,149,616 B2 | 12/2018 | Al-Ali et al. | |
| 10,154,815 B2 | 12/2018 | Al-Ali et al. | |
| 10,159,412 B2 | 12/2018 | Lamego et al. | |
| 10,188,296 B2 | 1/2019 | Al-Ali et al. | |
| 10,188,331 B1 | 1/2019 | Kiani et al. | |
| 10,188,348 B2 | 1/2019 | Al-Ali et al. | |
| RE47,218 E | 2/2019 | Al-Ali | |
| RE47,244 E | 2/2019 | Kiani et al. | |
| RE47,249 E | 2/2019 | Kiani et al. | |
| 10,194,847 B2 | 2/2019 | Al-Ali | |
| 10,194,848 B1 | 2/2019 | Kiani et al. | |
| 10,201,298 B2 | 2/2019 | Al-Ali et al. | |
| 10,205,272 B2 | 2/2019 | Kiani et al. | |
| 10,205,291 B2 | 2/2019 | Scruggs et al. | |
| 10,213,108 B2 | 2/2019 | Al-Ali | |
| 10,219,706 B2 | 3/2019 | Al-Ali | |
| 10,219,746 B2 | 3/2019 | McHale et al. | |
| 10,226,187 B2 | 3/2019 | Al-Ali et al. | |
| 10,226,576 B2 | 3/2019 | Kiani | |
| 10,231,657 B2 | 3/2019 | Al-Ali et al. | |
| 10,231,670 B2 | 3/2019 | Blank et al. | |
| 10,231,676 B2 | 3/2019 | Al-Ali et al. | |
| RE47,353 E | 4/2019 | Kiani et al. | |
| 10,251,585 B2 | 4/2019 | Al-Ali et al. | |
| 10,251,586 B2 | 4/2019 | Lamego | |
| 10,255,994 B2 | 4/2019 | Sampath et al. | |
| 10,258,265 B1 | 4/2019 | Poeze et al. | |
| 10,258,266 B1 | 4/2019 | Poeze et al. | |
| 10,271,748 B2 | 4/2019 | Al-Ali | |
| 10,278,626 B2 | 5/2019 | Schurman et al. | |
| 10,278,648 B2 | 5/2019 | Al-Ali et al. | |
| 10,279,247 B2 | 5/2019 | Kiani | |
| 10,292,628 B1 | 5/2019 | Poeze et al. | |
| 10,292,657 B2 | 5/2019 | Abdul-Hafiz et al. | |
| 10,292,664 B2 | 5/2019 | Al-Ali | |
| 10,299,708 B1 | 5/2019 | Poeze et al. | |
| 10,299,709 B2 | 5/2019 | Perea et al. | |
| 10,299,720 B2 | 5/2019 | Brown et al. | |
| 10,305,775 B2 | 5/2019 | Lamego et al. | |
| 10,307,111 B2 | 6/2019 | Muhsin et al. | |
| 10,325,681 B2 | 6/2019 | Sampath et al. | |
| 10,327,337 B2 | 6/2019 | Triman et al. | |
| 10,327,713 B2 | 6/2019 | Barker et al. | |

(56) References Cited

U.S. PATENT DOCUMENTS

| | | |
|---|---|---|
| 10,332,630 B2 | 6/2019 | Al-Ali |
| 10,335,033 B2 | 7/2019 | Al-Ali |
| 10,335,068 B2 | 7/2019 | Poeze et al. |
| 10,335,072 B2 | 7/2019 | Al-Ali et al. |
| 10,342,470 B2 | 7/2019 | Al-Ali et al. |
| 10,342,487 B2 | 7/2019 | Al-Ali et al. |
| 10,342,497 B2 | 7/2019 | Al-Ali et al. |
| 10,349,895 B2 | 7/2019 | Telfort et al. |
| 10,349,898 B2 | 7/2019 | Al-Ali et al. |
| 10,354,504 B2 | 7/2019 | Kiani et al. |
| 10,357,206 B2 | 7/2019 | Weber et al. |
| 10,357,209 B2 | 7/2019 | Al-Ali |
| 10,366,787 B2 | 7/2019 | Sampath et al. |
| 10,368,787 B2 | 8/2019 | Reichgott et al. |
| 10,376,190 B1 | 8/2019 | Poeze et al. |
| 10,376,191 B1 | 8/2019 | Poeze et al. |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| 10,398,320 B2 | 9/2019 | Kiani et al. |
| 10,405,804 B2 | 9/2019 | Al-Ali |
| 10,413,666 B2 | 9/2019 | Al-Ali et al. |
| 10,420,493 B2 | 9/2019 | Al-Ali et al. |
| D864,120 S | 10/2019 | Forrest et al. |
| 10,433,776 B2 | 10/2019 | Al-Ali |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| RE47,882 E | 3/2020 | Al-Ali |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 * | 4/2020 | Al-Ali ............... A61B 5/303 |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Al-Ali |
| 10,779,098 B2 | 9/2020 | Iswanto et al. |
| 10,799,160 B2 * | 10/2020 | Al-Ali ............... A61B 5/746 |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |
| 2002/0058864 A1 | 5/2002 | Mansfield et al. |
| 2002/0133080 A1 | 9/2002 | Apruzzese et al. |
| 2003/0013975 A1 | 1/2003 | Kiani |
| 2003/0018243 A1 | 1/2003 | Gerhardt et al. |
| 2003/0144582 A1 | 7/2003 | Cohen et al. |
| 2003/0156288 A1 | 8/2003 | Barnum et al. |
| 2003/0212312 A1 | 11/2003 | Coffin, IV et al. |
| 2004/0106163 A1 | 6/2004 | Workman, Jr. et al. |
| 2005/0055276 A1 | 3/2005 | Kiani et al. |
| 2005/0234317 A1 | 10/2005 | Kiani |
| 2006/0073719 A1 | 4/2006 | Kiani |
| 2006/0161054 A1 | 7/2006 | Reuss et al. |
| 2006/0189871 A1 | 8/2006 | Al-Ali et al. |
| 2007/0073116 A1 | 3/2007 | Kiani et al. |
| 2007/0139873 A1 | 6/2007 | Thomas et al. |
| 2007/0180140 A1 | 8/2007 | Welch et al. |
| 2007/0244377 A1 | 10/2007 | Cozad et al. |
| 2007/0282478 A1 | 12/2007 | Al-Ali et al. |
| 2008/0064965 A1 | 3/2008 | Jay et al. |
| 2008/0094228 A1 | 4/2008 | Welch et al. |
| 2008/0221418 A1 | 9/2008 | Al-Ali et al. |
| 2009/0036759 A1 | 2/2009 | Ault et al. |
| 2009/0093687 A1 | 4/2009 | Telfort et al. |
| 2009/0095926 A1 | 4/2009 | MacNeish, III |
| 2009/0247984 A1 | 10/2009 | Lamego et al. |
| 2009/0275813 A1 | 11/2009 | Davis |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2010/0099964 A1 | 4/2010 | O'Reilly et al. |
| 2010/0234718 A1 | 9/2010 | Sampath et al. |
| 2010/0270257 A1 | 10/2010 | Wachman et al. |
| 2010/0291804 A1 | 11/2010 | Zhang et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0082711 A1 | 4/2011 | Poeze et al. |
| 2011/0087081 A1 | 4/2011 | Kiani et al. |
| 2011/0118561 A1 | 5/2011 | Tani et al. |
| 2011/0125060 A1 | 5/2011 | Telfort et al. |
| 2011/0137297 A1 | 6/2011 | Kiani et al. |
| 2011/0172498 A1 | 7/2011 | Olsen et al. |
| 2011/0208015 A1 | 8/2011 | Welch et al. |
| 2011/0230733 A1 | 9/2011 | Al-Ali |
| 2012/0123231 A1 | 5/2012 | O'Reilly |
| 2012/0165629 A1 | 6/2012 | Merritt et al. |
| 2012/0209082 A1 | 8/2012 | Al-Ali |
| 2012/0209084 A1 | 8/2012 | Olsen et al. |
| 2012/0226117 A1 | 9/2012 | Lamego et al. |
| 2012/0283524 A1 | 11/2012 | Kiani et al. |
| 2013/0023775 A1 | 1/2013 | Lamego et al. |
| 2013/0041591 A1 | 2/2013 | Lamego |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0243021 A1 | 9/2013 | Siskavich |
| 2013/0253334 A1 | 9/2013 | Al-Ali et al. |
| 2013/0296672 A1 | 11/2013 | O'Neil et al. |
| 2013/0296713 A1 | 11/2013 | Al-Ali et al. |
| 2013/0324808 A1 | 12/2013 | Al-Ali et al. |
| 2013/0331660 A1 | 12/2013 | Al-Ali et al. |
| 2013/0345921 A1 | 12/2013 | Al-Ali et al. |
| 2014/0012100 A1 | 1/2014 | Al-Ali et al. |
| 2014/0051953 A1 | 2/2014 | Lamego et al. |
| 2014/0120564 A1 | 5/2014 | Workman et al. |
| 2014/0121482 A1 | 5/2014 | Merritt et al. |
| 2014/0127137 A1 | 5/2014 | Bellott et al. |
| 2014/0163344 A1 | 6/2014 | Al-Ali |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0213864 A1 | 7/2014 | Abdul-Hafiz et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0275873 A1 | 9/2014 | Fries et al. |
| 2014/0288400 A1 | 9/2014 | Diab et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0357966 A1 | 12/2014 | Al-Ali et al. |
| 2015/0005600 A1 | 1/2015 | Blank et al. |
| 2015/0011907 A1 | 1/2015 | Purdon et al. |
| 2015/0032029 A1 | 1/2015 | Al-Ali et al. |
| 2015/0038859 A1 | 2/2015 | Dalvi et al. |

(56) References Cited

U.S. PATENT DOCUMENTS

| | | |
|---|---|---|
| 2015/0073241 A1 | 3/2015 | Lamego |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0099950 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0165312 A1 | 6/2015 | Kiani |
| 2015/0196249 A1 | 7/2015 | Brown et al. |
| 2015/0216459 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0272514 A1 | 10/2015 | Kiani et al. |
| 2015/0351697 A1 | 12/2015 | Weber et al. |
| 2015/0359429 A1 | 12/2015 | Al-Ali et al. |
| 2015/0366507 A1 | 12/2015 | Blank et al. |
| 2016/0029932 A1 | 2/2016 | Al-Ali |
| 2016/0058347 A1 | 3/2016 | Reichgott et al. |
| 2016/0066824 A1 | 3/2016 | Al-Ali et al. |
| 2016/0081552 A1 | 3/2016 | Wojtczuk et al. |
| 2016/0093970 A1 | 3/2016 | Wu et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0166182 A1 | 6/2016 | Al-Ali et al. |
| 2016/0166183 A1 | 6/2016 | Poeze et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0234944 A1 | 8/2016 | Schmidt et al. |
| 2016/0270735 A1 | 9/2016 | Diab et al. |
| 2016/0283665 A1 | 9/2016 | Sampath et al. |
| 2016/0287090 A1 | 10/2016 | Al-Ali et al. |
| 2016/0287786 A1 | 10/2016 | Kiani |
| 2016/0296169 A1 | 10/2016 | McHale et al. |
| 2016/0310052 A1 | 10/2016 | Al-Ali et al. |
| 2016/0314260 A1 | 10/2016 | Kiani |
| 2016/0324488 A1 | 11/2016 | Olsen |
| 2016/0327984 A1 | 11/2016 | Al-Ali et al. |
| 2016/0331332 A1 | 11/2016 | Al-Ali |
| 2016/0367173 A1 | 12/2016 | Dalvi et al. |
| 2017/0000394 A1 | 1/2017 | Al-Ali et al. |
| 2017/0007134 A1 | 1/2017 | Al-Ali et al. |
| 2017/0007198 A1 | 1/2017 | Al-Ali et al. |
| 2017/0014083 A1 | 1/2017 | Diab et al. |
| 2017/0014084 A1 | 1/2017 | Al-Ali et al. |
| 2017/0024748 A1 | 1/2017 | Haider |
| 2017/0042488 A1 | 2/2017 | Muhsin |
| 2017/0055851 A1 | 3/2017 | Al-Ali |
| 2017/0055882 A1 | 3/2017 | Al-Ali et al. |
| 2017/0055887 A1 | 3/2017 | Al-Ali |
| 2017/0055896 A1 | 3/2017 | Al-Ali |
| 2017/0079594 A1 | 3/2017 | Telfort et al. |
| 2017/0086723 A1 | 3/2017 | Al-Ali et al. |
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0173632 A1 | 6/2017 | Al-Ali |
| 2017/0187146 A1 | 6/2017 | Kiani et al. |
| 2017/0188919 A1 | 7/2017 | Al-Ali et al. |
| 2017/0196464 A1 | 7/2017 | Jansen et al. |
| 2017/0196470 A1 | 7/2017 | Lamego et al. |
| 2017/0224262 A1 | 8/2017 | Al-Ali |
| 2017/0228516 A1 | 8/2017 | Sampath et al. |
| 2017/0245790 A1 | 8/2017 | Al-Ali et al. |
| 2017/0251974 A1 | 9/2017 | Shreim et al. |
| 2017/0251975 A1 | 9/2017 | Shreim et al. |
| 2017/0258403 A1 | 9/2017 | Abdul-Hafiz et al. |
| 2017/0311851 A1 | 11/2017 | Schurman et al. |
| 2017/0311891 A1 | 11/2017 | Kiani et al. |
| 2017/0325728 A1 | 11/2017 | Al-Ali et al. |
| 2017/0332976 A1 | 11/2017 | Al-Ali |
| 2017/0340293 A1 | 11/2017 | Al-Ali et al. |
| 2017/0360310 A1 | 12/2017 | Kiani |
| 2017/0367632 A1 | 12/2017 | Al-Ali et al. |
| 2018/0008146 A1 | 1/2018 | Al-Ali et al. |
| 2018/0013562 A1 | 1/2018 | Haider et al. |
| 2018/0014752 A1 | 1/2018 | Al-Ali et al. |
| 2018/0028124 A1 | 2/2018 | Al-Ali et al. |
| 2018/0055385 A1 | 3/2018 | Al-Ali |
| 2018/0055390 A1 | 3/2018 | Kiani et al. |
| 2018/0055430 A1 | 3/2018 | Diab et al. |
| 2018/0064381 A1 | 3/2018 | Shakespeare et al. |
| 2018/0069776 A1 | 3/2018 | Lamego et al. |
| 2018/0070867 A1 | 3/2018 | Smith et al. |
| 2018/0082767 A1 | 3/2018 | Al-Ali et al. |
| 2018/0085068 A1 | 3/2018 | Telfort |
| 2018/0087937 A1 | 3/2018 | Al-Ali et al. |
| 2018/0103874 A1 | 4/2018 | Lee et al. |
| 2018/0103905 A1 | 4/2018 | Kiani |
| 2018/0110478 A1 | 4/2018 | Al-Ali |
| 2018/0116575 A1 | 5/2018 | Perea et al. |
| 2018/0125368 A1 | 5/2018 | Lamego et al. |
| 2018/0125430 A1 | 5/2018 | Al-Ali et al. |
| 2018/0125445 A1 | 5/2018 | Telfort et al. |
| 2018/0130325 A1 | 5/2018 | Kiani et al. |
| 2018/0132769 A1 | 5/2018 | Weber et al. |
| 2018/0132770 A1 | 5/2018 | Lamego |
| 2018/0146901 A1 | 5/2018 | Al-Ali et al. |
| 2018/0146902 A1 | 5/2018 | Kiani et al. |
| 2018/0153442 A1 | 6/2018 | Eckerbom et al. |
| 2018/0153446 A1 | 6/2018 | Kiani |
| 2018/0153447 A1 | 6/2018 | Al-Ali et al. |
| 2018/0153448 A1 | 6/2018 | Weber et al. |
| 2018/0161499 A1 | 6/2018 | Al-Ali et al. |
| 2018/0168491 A1 | 6/2018 | Al-Ali et al. |
| 2018/0174679 A1 | 6/2018 | Sampath et al. |
| 2018/0174680 A1 | 6/2018 | Sampath et al. |
| 2018/0182484 A1 | 6/2018 | Sampath et al. |
| 2018/0184917 A1 | 7/2018 | Kiani |
| 2018/0192924 A1 | 7/2018 | Al-Ali |
| 2018/0192953 A1 | 7/2018 | Shreim et al. |
| 2018/0192955 A1 | 7/2018 | Al-Ali et al. |
| 2018/0199871 A1 | 7/2018 | Pauley et al. |
| 2018/0206795 A1 | 7/2018 | Al-Ali |
| 2018/0206815 A1 | 7/2018 | Telfort |
| 2018/0213583 A1 | 7/2018 | Al-Ali |
| 2018/0214031 A1 | 8/2018 | Kiani et al. |
| 2018/0214090 A1 | 8/2018 | Al-Ali et al. |
| 2018/0218792 A1 | 8/2018 | Muhsin et al. |
| 2018/0225960 A1 | 8/2018 | Al-Ali et al. |
| 2018/0238718 A1 | 8/2018 | Dalvi |
| 2018/0242853 A1 | 8/2018 | Al-Ali |
| 2018/0242921 A1 | 8/2018 | Muhsin et al. |
| 2018/0242923 A1 | 8/2018 | Al-Ali et al. |
| 2018/0242924 A1 | 8/2018 | Barker et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0249933 A1 | 9/2018 | Schurman et al. |
| 2018/0253947 A1 | 9/2018 | Muhsin et al. |
| 2018/0256087 A1 | 9/2018 | Al-Ali et al. |
| 2018/0256113 A1 | 9/2018 | Weber et al. |
| 2018/0285094 A1 | 10/2018 | Housel et al. |
| 2018/0289325 A1 | 10/2018 | Poeze et al. |
| 2018/0289337 A1 | 10/2018 | Al-Ali et al. |
| 2018/0296161 A1 | 10/2018 | Shreim et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin et al. |
| 2018/0317841 A1 | 11/2018 | Novak, Jr. |
| 2018/0333055 A1 | 11/2018 | Lamego et al. |
| 2018/0333087 A1 | 11/2018 | Al-Ali |
| 2019/0000317 A1 | 1/2019 | Muhsin et al. |
| 2019/0000362 A1 | 1/2019 | Kiani et al. |
| 2019/0015023 A1 | 1/2019 | Monfre |
| 2019/0021638 A1 | 1/2019 | Al-Ali et al. |
| 2019/0029574 A1 | 1/2019 | Schurman et al. |
| 2019/0029578 A1 | 1/2019 | Al-Ali et al. |

(56) References Cited

U.S. PATENT DOCUMENTS

| | | |
|---|---|---|
| 2019/0038143 A1 | 2/2019 | Al-Ali |
| 2019/0058280 A1 | 2/2019 | Al-Ali et al. |
| 2019/0058281 A1 | 2/2019 | Al-Ali et al. |
| 2019/0069813 A1 | 3/2019 | Al-Ali |
| 2019/0069814 A1 | 3/2019 | Al-Ali |
| 2019/0076028 A1 | 3/2019 | Al-Ali et al. |
| 2019/0082979 A1 | 3/2019 | Al-Ali et al. |
| 2019/0090748 A1 | 3/2019 | Al-Ali |
| 2019/0090760 A1 | 3/2019 | Kinast et al. |
| 2019/0090764 A1 | 3/2019 | Al-Ali |
| 2019/0104973 A1 | 4/2019 | Poeze et al. |
| 2019/0110719 A1 | 4/2019 | Poeze et al. |
| 2019/0117070 A1 | 4/2019 | Muhsin et al. |
| 2019/0117139 A1 | 4/2019 | Al-Ali et al. |
| 2019/0117140 A1 | 4/2019 | Al-Ali et al. |
| 2019/0117141 A1 | 4/2019 | Al-Ali |
| 2019/0117930 A1 | 4/2019 | Al-Ali |
| 2019/0122763 A1 | 4/2019 | Sampath et al. |
| 2019/0133525 A1 | 5/2019 | Al-Ali et al. |
| 2019/0142283 A1 | 5/2019 | Lamego et al. |
| 2019/0142344 A1 | 5/2019 | Telfort et al. |
| 2019/0150800 A1 | 5/2019 | Poeze et al. |
| 2019/0150856 A1 | 5/2019 | Kiani et al. |
| 2019/0167161 A1 | 6/2019 | Al-Ali et al. |
| 2019/0175019 A1 | 6/2019 | Al-Ali et al. |
| 2019/0192076 A1 | 6/2019 | McHale et al. |
| 2019/0200941 A1 | 7/2019 | Chandran et al. |
| 2019/0201623 A1 | 7/2019 | Kiani |
| 2019/0209025 A1 | 7/2019 | Al-Ali |
| 2019/0214778 A1 | 7/2019 | Scruggs et al. |
| 2019/0216319 A1 | 7/2019 | Poeze et al. |
| 2019/0216379 A1 | 7/2019 | Al-Ali et al. |
| 2019/0221966 A1 | 7/2019 | Kiani et al. |
| 2019/0223804 A1 | 7/2019 | Blank et al. |
| 2019/0231199 A1 | 8/2019 | Al-Ali et al. |
| 2019/0231241 A1 | 8/2019 | Al-Ali et al. |
| 2019/0231270 A1 | 8/2019 | Abdul-Hafiz et al. |
| 2019/0239787 A1 | 8/2019 | Pauley et al. |
| 2019/0239824 A1 | 8/2019 | Muhsin et al. |
| 2019/0254578 A1 | 8/2019 | Lamego |
| 2019/0261857 A1 | 8/2019 | Al-Ali |
| 2019/0269370 A1 | 9/2019 | Al-Ali et al. |
| 2019/0274606 A1 | 9/2019 | Kiani et al. |
| 2019/0274627 A1 | 9/2019 | Al-Ali et al. |
| 2019/0274635 A1 | 9/2019 | Al-Ali et al. |
| 2019/0290136 A1 | 9/2019 | Dalvi et al. |
| 2019/0298270 A1 | 10/2019 | Al-Ali et al. |
| 2019/0304601 A1 | 10/2019 | Sampath et al. |
| 2019/0304605 A1 | 10/2019 | Al-Ali |
| 2019/0307377 A1 | 10/2019 | Perea et al. |
| 2019/0320906 A1 | 10/2019 | Olsen |
| 2019/0320959 A1 | 10/2019 | Al-Ali |
| 2019/0320988 A1 | 10/2019 | Ahmed et al. |
| 2019/0374139 A1 | 12/2019 | Kiani et al. |
| 2019/0374173 A1 | 12/2019 | Kiani et al. |
| 2019/0374713 A1 | 12/2019 | Kiani et al. |
| 2020/0060869 A1 | 2/2020 | Telfort et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |

OTHER PUBLICATIONS

Promed Technologies, RD SET MP—05, Code 4083, dated Apr. 14, 2017. Available from https://www.promedtech.co.nz/shop/masimo/masimo-cables/cables-rd-set/rd-set-mp-05-code-4083/, 1 page.

Masimo, LNCS Series M20 Patient Cable, dated May 12, 2018. Available from http://www.masimo.com/products/sensors/lncs/cables/, 1 page.

* cited by examiner

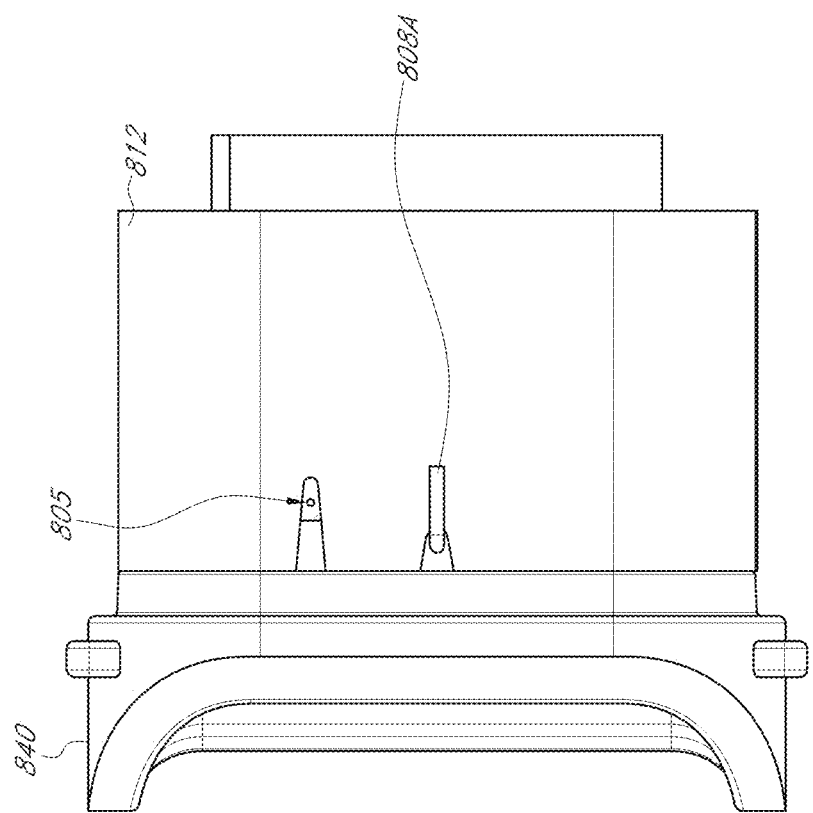

WATER RESISTANT CONNECTOR FOR NONINVASIVE PATIENT MONITOR

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

This application is a continuation of U.S. patent application Ser. No. 16/102,456 entitled "Water Resistant Connector for Noninvasive Patient Monitor" filed Aug. 13, 2018, which claims benefit of U.S. Provisional Patent Application Ser. No. 62/545,884 entitled "Water Resistant Connector for Noninvasive Patient Monitor" filed Aug. 15, 2017, and U.S. Provisional Patent Application Ser. No. 62/545,877 entitled "Water Resistant Connector for Noninvasive Patient Monitor" filed Aug. 15, 2017, which are hereby incorporated by reference in their entireties.

BACKGROUND

Energy is often transmitted through or reflected from a medium to determine characteristics of the medium. For example, in the medical field, instead of extracting material from a patient's body for testing, light or sound energy may be caused to be incident on the patient's body and transmitted (or reflected) energy may be measured to determine information about the material through which the energy has passed. This type of non-invasive measurement is more comfortable for the patient and can be performed more quickly than invasive measurement techniques.

Non-invasive physiological monitoring of bodily function is often required. For example, during surgery or other hospital visits, blood pressure and the body's available supply of oxygen, or the blood oxygen saturation, are often monitored. Measurements such as these are often performed with non-invasive techniques where assessments are made by measuring the ratio of incident to transmitted (or reflected) light through a portion of the body, for example a digit such as a finger, or an earlobe, foot, or forehead.

Durable and disposable sensors are often used for such physiological measurements. These sensors have connectors that allow detachment from the instrument or cable from the instrument.

SUMMARY

For purposes of summarizing the disclosure, certain aspects, advantages and novel features are discussed herein. It is to be understood that not necessarily all such aspects, advantages or features will be embodied in any particular embodiment of the invention and an artisan would recognize from the disclosure herein a myriad of combinations of such aspects, advantages or features.

One embodiment includes a water-resistant medical device cable assembly configured to interface one or more noninvasive physiological sensors with a patient monitor, the cable assembly comprising: a cable configured to connect to a physiological sensor, the cable comprising a plurality of conductors configured to obtain physiological signals from a patient; and a male connector attached to the cable and configured to couple the cable with a patient monitor so as to convey the physiological signals from the physiological sensor to the patient monitor, the male connector comprising: a rigid frame; a circuit board disposed within the rigid frame and connected with the conductors in the cable; a plurality of electrical contacts disposed on the circuit board, the plurality of electrical contacts operative to contact second electrical contacts in a corresponding female connector of the patient monitor when the male connector is inserted into the female connector; a pliable overmold configured to cover a portion of the rigid frame and a portion of the circuit board but not the plurality of electrical contacts, wherein the plurality of electrical contacts are open to air when the male connector is disconnected from the female connector of the patient monitor; and a raised rib disposed on the pliable overmold, the raised rib circumferentially surrounding the pliable overmold and configured to create a seal with the female connector when the male connector is inserted into the female connector, such that when the male connector is inserted into the female connector, the plurality electrical contacts of the male connector are no longer exposed to air, such that a water-resistant seal is created between the male connector and the female connector.

One embodiment includes a water-resistant medical device cable assembly configured to interface one or more noninvasive physiological sensors with a patient monitor, the cable assembly comprising: a cable configured to connect to a physiological sensor, the cable comprising a plurality of conductors configured to obtain physiological signals from a patient; and a male connector attached to the cable and configured to couple the cable with a patient monitor so as to convey the physiological signals from the physiological sensor to the patient monitor, the male connector comprising: a rigid frame; a circuit board disposed within the rigid frame and connected with the conductors in the cable; a plurality of electrical contacts disposed on the circuit board, the plurality of electrical contacts operative to contact second electrical contacts in a corresponding female connector of the patient monitor when the male connector is inserted into the female connector; and a pliable overmold configured to cover a portion of the rigid frame and a portion of the circuit board but not the plurality of electrical contacts, wherein the plurality of electrical contacts are open to air when the male connector is disconnected from the female connector of the patient monitor, and wherein the pliable overmold is further configured to create a seal with the female connector when the male connector is inserted into the female connector, such that when the male connector is inserted into the female connector, the plurality electrical contacts of the male connector are no longer exposed to air, such that a water-resistant seal is created between the male connector and the female connector.

In some embodiments, the water-resistant medical device cable assembly of the preceding paragraph can include a combination or sub-combination of features. The male connector can include a raised rib disposed on the pliable overmold, the raised rib circumferentially surrounding the pliable overmold.

One embodiment includes a cable assembly comprising: a cable comprising a plurality of conductors; and a male connector attached to the cable, the male connector comprising: a rigid frame; a circuit board disposed within the rigid frame and connected with the conductors in the cable; a plurality of electrical contacts disposed on the circuit board, the plurality of electrical contacts operative to contact second electrical contacts in a corresponding female connector when the male connector is inserted into the female connector; a pliable overmold configured to cover a portion of the rigid frame and a portion of the circuit board but not the plurality of electrical contacts, wherein the plurality of electrical contacts are open to air when the male connector is disconnected from the female connector; and a raised rib disposed on the pliable overmold, the raised rib circumferentially surrounding the pliable overmold and configured to create a seal with the female connector when the male connector is inserted into the female connector, such that when the male connector is inserted into the female connector, the plurality electrical contacts of the male connector are no longer exposed to air, such that a water-resistant seal is created between the male connector and the female connector.

In some embodiments, the water-resistant medical device cable assembly or the cable assembly of the preceding paragraphs can include a combination or sub-combination of features. The raised rib can be a part of the pliable overmold. The raised rib can include a thermoplastic elastomer. The pliable overmold can include a thermoplastic elastomer. A width of the raised rib can be between approximately 0.762 millimeters (0.03 inches) and approximately 0.8128 millimeters (0.032 inches). A height of the raised rib can be between approximately 0.254 millimeters (0.01 inches) and approximately 0.508 millimeters (0.02 inches). The pliable overmold can further include a first portion and a second portion, the first portion can be located between the plurality of electrical contacts and the second portion, the second portion can be adjacent to the cable, wherein a first width of a proximal end of the first portion can be narrower than a second width of a distal end of the first portion. The first width can be between 2.03 centimeters (0.8 inches) and approximately 2.06 centimeters (0.81 inches), and the second width can be between approximately 2.06 centimeters (0.8H inches) and approximately 2.08 centimeters (0.82 inches). The water-resistant medical device cable assembly or the cable assembly can further include an inner covering configured to cover a portion of the cable, the inner covering can be adjacent to the rigid frame and can be located between the rigid frame and a distal end of the cable, wherein the inner covering can be further configured to seal a distal end of the rigid frame and a proximal end of the cable, and wherein the pliable overmold can be further configured to cover the inner covering. The inner covering can further include a thermoplastic polymer. The thermoplastic polymer can include polypropylene.

One embodiment includes a patient monitor comprising: a hardware processor configured to process physiological signals to obtain measurements; a display configured to present at least some of the measurements; and a female connector configured to receive the physiological signals from a physiological sensor, the female connector further configured to couple the physiological sensor with the patient monitor, the female connector comprising: a rigid frame comprising a plurality of pockets; a circuit board disposed within the rigid frame and configured to transmit the physiological signals to the hardware processor; a plurality of electrical contacts disposed on the circuit board, each electrical contact of the plurality of electrical contacts disposed within each pocket of the plurality of pockets, the plurality of electrical contacts: operative to contact second electrical contacts in a corresponding male connector when the male connector is inserted into the female connector, the male connector coupled to the physiological sensor, and partially exposed to air when the male connector is not inserted into the female connector; a rigid mold circumferentially surrounding the plurality of electrical contacts and configured to create a water-resistant seal around the plurality of electrical contacts; a proximal opening configured to receive the male connector; and a distal opening configured to receive the male connector, wherein a first height of the distal opening is shorter than a second height of the proximal opening In some embodiments, the patient monitor of the preceding paragraph can include a combination or sub-combination of features. The first height of the distal opening can be between approximately 0.74 centimeters (0.29 inches) and approximately 0.76 centimeters (0.3 inches), and wherein the second height of the proximal opening is between approximately 0.16 centimeters (0.063 inches) and approximately 0.18 centimeters (0.07 inches).

One embodiment includes a patient monitor comprising: a hardware processor configured to process physiological signals to obtain measurements; a display configured to present at least some of the measurements; and a female connector configured to receive the physiological signals from a physiological sensor, the female connector further configured to couple the physiological sensor with the patient monitor, the female connector comprising: a rigid frame comprising a plurality of pockets; a circuit board disposed within the rigid frame and configured to transmit the physiological signals to the hardware processor; a plurality of electrical contacts disposed on the circuit board, each electrical contact of the plurality of electrical contacts disposed within each pocket of the plurality of pockets, the plurality of electrical contacts: operative to contact second electrical contacts in a corresponding male connector when the male connector is inserted into the female connector, the male connector coupled to the physiological sensor, and partially exposed to air when the male connector is not inserted into the female connector; a rigid mold circumferentially surrounding the plurality of electrical contacts and configured to create a water-resistant seal around the plurality of electrical contacts; and a detent holder configured to engage with a detent of the male connector.

One embodiment includes a patient monitor comprising: a hardware processor configured to process physiological signals to obtain measurements; a display configured to present at least some of the measurements; and a female connector configured to receive the physiological signals from a physiological sensor, the female connector further configured to couple the physiological sensor with the patient monitor, the female connector comprising: a rigid frame comprising a plurality of pockets; a circuit board disposed within the rigid frame and configured to transmit the physiological signals to the hardware processor; a plurality of electrical contacts disposed on the circuit board, each electrical contact of the plurality of electrical contacts disposed within each pocket of the plurality of pockets, the plurality of electrical contacts: operative to contact second electrical contacts in a corresponding male connector when the male connector is inserted into the female connector, the male connector coupled to the physiological sensor, and partially exposed to air when the male connector is not inserted into the female connector; and a rigid mold circumferentially surrounding the plurality of electrical contacts and configured to create a water-resistant seal around the plurality of electrical contacts.

One embodiment includes a patient monitor connector configured to interface one or more noninvasive physiological sensors, the patient monitor connector comprising: a female connector of a patient monitor, the female connector configured to receive physiological signals from a physiological sensor, the female connector comprising: a rigid frame comprising a plurality of pockets; a circuit board disposed within the rigid frame and configured to transmit the physiological signals to a hardware processor; a plurality of electrical contacts disposed on the circuit board, each electrical contact of the plurality of electrical contacts disposed within each pocket of the plurality of pockets, the plurality of electrical contacts: operative to contact second electrical contacts in a corresponding male connector when the male connector is inserted into the female connector, the male connector coupled to the physiological sensor, and partially exposed to air when the male connector is not inserted into the female connector; and a rigid mold circumferentially surrounding the plurality of electrical contacts and configured to create a water-resistant seal around the plurality of electrical contacts.

On embodiment includes a female connector comprising: a rigid frame comprising a plurality of pockets; a circuit board disposed within the rigid frame; a plurality of electrical contacts disposed on the circuit board, each electrical contact of the plurality of electrical contacts disposed within each pocket of the plurality of pockets, the plurality of electrical contacts: operative to contact second electrical contacts in a corresponding male connector when the male connector is inserted into the female connector, and partially exposed to air when the male connector is not inserted into the female connector; and a rigid mold circumferentially surrounding the plurality of electrical contacts and configured to create a water-resistant seal around the plurality of electrical contacts.

In some embodiments, the patient monitor or the female connector of the preceding paragraphs can include a combination or sub-combination of features. The female connector can further include a distal opening configured to receive the male connector, wherein a first height of the distal opening can be between approximately 0.74 centimeters (0.29 inches) and approximately 0.76 centimeters (0.3 inches); and a proximal opening configured to receive the male connector, wherein a second height of the proximal opening can be between approximately 0.16 centimeters (0.063 inches) and approximately 0.18 centimeters (0.07 inches). A first contact of the plurality of electrical contacts can include a spring contact. The female connector can further include a detent holder configured to engage with a detent of the male connector. The detent holder can include a pocket. The rigid mold can further include a thermoplastic polymer. The thermoplastic polymer can include polypropylene.

DETAILED DESCRIPTION

I. Connector Introduction

Figure 1:
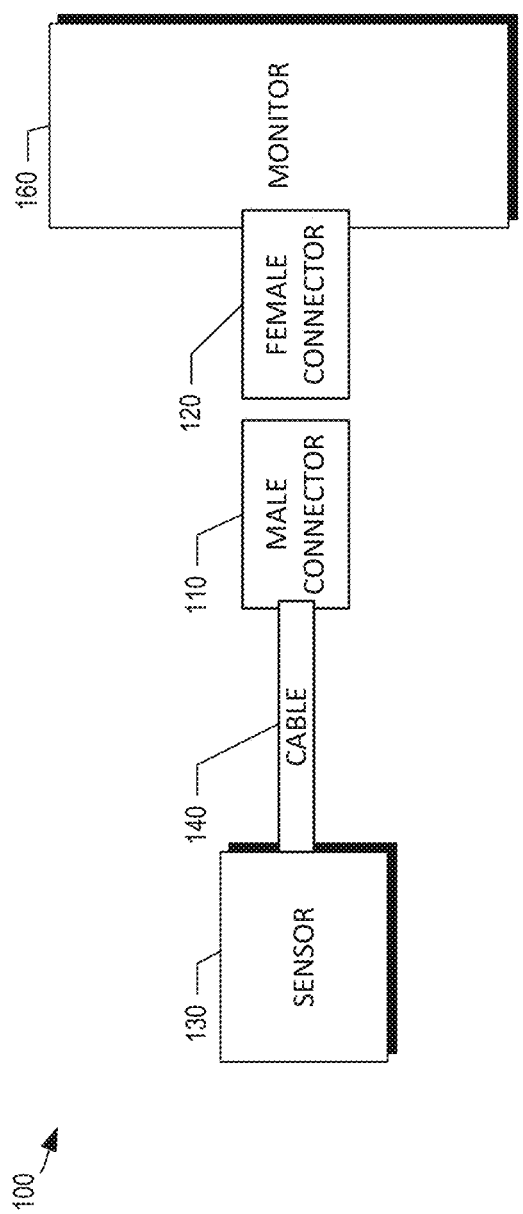
FIG. 1 is a block diagram illustrating connectors in a patient monitoring system, according to some embodiments of the present disclosure.

A water resistant connector may be advantageous in one or more situations. A clinician, such as an emergency medical technician (EMT), may respond to an emergency situation and may use one or more electronic medical devices, such as a noninvasive physiological sensor and a patient monitor. It can be outdoors, raining, and the electronic medical devices can get wet. An EMT may also respond to a fire, there may be water around, and the EMT drops the electronic medical device in a puddle or the electronic medical device gets sprayed with a hose. In a hospital or clinic setting, a staff person can clean, wipe down, or spray the electronic medical devices with a cleaning solution such as isopropyl alcohol. A water resistant connector may be advantageous in any of the previous situations where a clinician does not have to be concerned about an electronic device shorting or not working if the device gets wet. Thus, a water resistant connector can improve the reliability of electronic medical devices in emergency or medical situations and can assist in saving lives.

Disclosed herein are embodiments of connectors that may be water resistant. A connector may include a rib that creates a seal when engaged with another connector. A connector may include a draft angle that creates a seal when engaged with another connector. Some connector embodiments can include a mold. Some connector embodiments include an overmold that can include and/or can be made of a thermoplastic elastomer (TPE) that advantageously improves sealing and/or water resistance. Some molds can include and/or can be made of a thermoplastic polymer, such as polypropylene, that may advantageously improve sealing and/or water resistance. Some connector embodiments can include spring contacts that fit within individual pockets and that when combined with a sealing material, such as a thermoplastic polymer, can create a water resistant barrier. In some embodiments, the water resistant features described herein may reduce and/or prevent electrical shorts.

In some embodiments, a water resistant connector can be used with physiological monitoring systems, such as systems that use a pulse oximetry device and/or an acoustic respiration monitor. Pulse oximetry provides a noninvasive procedure for measuring the oxygen status of circulating blood and may be used in a wide variety of medical contexts, such as surgical wards, intensive care units, neonatal units, general wards, home care, physical training, clinics, and emergency medical situations. A pulse oximetry system generally includes a physiological sensor applied to a patient, a monitor, and a cable connecting the sensor and the monitor. The sensor has light emitters and a detector, which are attached to a tissue site, such as a finger. The cable can transmit emitter drive signals from the monitor to the sensor where the emitters respond to the drive signals to transmit light into the tissue site. The detector is responsive to the emitted light after attenuation by pulsatile blood flowing in the tissue site. The detector outputs a detector signal to the monitor. The monitor processes the detector signal to provide a numerical readout of physiological parameters such as oxygen saturation (SpO2) and pulse rate. Enhanced oximetry systems can also include a multiple parameter monitor and a multiple wavelength sensor that provide enhanced measurement capabilities, including the measurement of a multitude of blood constituents and related parameters in addition to oxygen saturation and pulse rate, such as, carboxyhemoglobin (HbCO), methemoglobin (HbMet), total Hematocrit (Hct), total hemoglobin (Hbt), oxygen concentrations, glucose concentrations, blood pressure, electrocardiogram data, temperature, respiratory rate, and/or acoustic respiration rate (RRa®), as a few examples. Advanced physiological monitors and multiple wavelength optical sensors capable of measuring parameters in addition to SpO2, such as HbCO, HbMet, Hct, and/or Hbt are described in at least U.S. patent application Ser. No. 11/367,013, filed Mar. 1, 2006, titled Multiple Wavelength Sensor Emitters, now issued as U.S. Pat. No. 7,764,982, and U.S. patent application Ser. No. 11/366,208, filed Mar. 1, 2006, titled Noninvasive Multi-Parameter Patient Monitor, now issued as U.S. Pat. No. 8,130,105, which are hereby incorporated by reference in their entireties. Further, noninvasive blood parameter monitors and optical sensors including Rainbow™ adhesive and reusable sensors and RAD-57™ and Radical-7™ monitors capable of measuring SpO2, pulse rate, perfusion index (PI), signal quality (SiQ), pulse variability index (PVI), HbCO and/or HbMet, among other parameters, are also commercially available from Masimo Corp. of Irvine, Calif.

As used herein, in addition to having its ordinary meaning, the term "water resistant" refers to the ability to resist the penetration of water and/or other liquids. In some embodiments, water resistance does not require complete prevention of liquid penetration, but rather resistance to some degree or complete penetration prevention for a finite period of time. Water resistance may be defined by a code, such as the Ingress Protection code. Example water resistant standards can include IPX6, IPX7, and IP67. IPX6 indicates protection from a 12.5 millimeters spray of water (100 liters per minute), such as powerful jets, in any direction for at least 3 minutes. IPX7 indicates protection from water submersion for up to one-meter deep for at least 30 minutes. IP67 indicates protection from contact with dust (6) and protection from water submersion for up to one-meter deep for at least 30 minutes (7). Some embodiments described herein may meet IPX6, IPX7, and/or IP67 standards. Additional details regarding water resistance, ingress protection, and/or standards thereof may be found in IEC 60529, "Degrees of Protection Provided by Enclosures (IP Codes)" (International Electrotechnical Commission, ed. 2.1, 2001), which is hereby incorporated by reference in its entirety.

For convenience, the terms "proximal" and "distal" are used herein to describe structures relative to the insertion point between a male connector and a female connector. The term "distal" refers to a portion of a first connector (either male or female) that is farther away from the deepest insertion point between the first connector and a second connector. The term "proximal" refers to a portion of a first connector (either male or female) that is closer to the deepest insertion point between the first connector and a second connector.

II. Connector Overview

FIG. 1 illustrates a connector environment 100 as part of a patient monitoring system. The connector environment 100 can include a sensor 130, a monitor 160, and a cable 140. The cable 140 can interconnects the sensor 130 and the monitor 160. A first cable assembly can include the cable 140 and the male connector 110 that connects to the female connector 120 of the monitor 160, which may advantageously enable a water resistant connection. The male connector 110 can be attached to the cable 140.

The features of the male connector 110 may improve water resistance. The male connector 110 can include a rib that creates a seal when engaged with the female connector 120. The male connector 110 can include a draft angle that creates a seal when engaged with the female connector 120. The male connector 110 can include an overmold that can include and/or can be made of thermoplastic elastomer. Additional details regarding the male connector 110 are described below with respect to FIGS. 4A-4F and 5A-5E.

The features of the female connector 120 may improve water resistance. The female connector 120 can include spring contacts that fit within individual pockets of the female connector 120. The female connector 120 can include a mold that can include and/or can be made of a thermoplastic polymer, such as polypropylene. The spring contacts that fit within individual pockets when combined with the mold may create a water resistant barrier that prevents water from entering the monitor 160. Additional details regarding the female connector 120 are described below with respect to FIGS. 8A-8S and 9A-9F.

In some embodiments, the first cable assembly can interface one or more noninvasive physiological sensors with a patient monitor. The sensor 130 can be a physiological sensor and the monitor 160 can be a patient monitor. Thus, the cable 140 can interconnect with the physiological sensor 130. The cable 140 can include a set of conductors that can obtain physiological signals from a patient. The male connector 110, which is attached to the cable 140, can couple the cable 140 with the patient monitor 130 to convey the physiological signals from the physiological sensor 130 to the patient monitor 160.

In some embodiments, the male connector 110 and/or the female connector 120 accept different types of sensors and sensor configurations. As shown, the male connector can be coupled to a direct connector sensor, such as a DCI, DCIP, or DCI-mini sensor. The male connector 110 and/or the female connector 120 can accept a SpO2 sensor. In other embodiments, the male connector 110 and/or the female connector 120 can accept a multiple wavelength sensor, such as a 3, 8, 16 or more or another numbered wavelength sensor. In yet further embodiments, the male connector 110 and/or the female connector 120 can accept both a SpO2 connector and a multiple wavelength sensor. Other sensor types and/or configurations are described in further detail below, such as with respect to FIG. 13.

In some embodiments, the cable 140 can connect to multiple sensors. An example cable 140 is a dual cable (not illustrated). The dual cable can have dual channels. An example dual cable is shown and described below with respect to FIGS. 7D-7F. A first sensor and a second sensor can connect to the dual cable. Each of the first and second sensors can have their own respective cables and connectors. Accordingly, a first channel of the dual cable can be compatible with a first sensor and a second channel of the dual cable can be compatible with a second sensor. An example first sensor is an SpO2 sensor. An example second connector is an acoustic monitoring sensor. Additional sensors are described in further detail below, such as with respect to FIG. 13.

III. Male Connectors

Figure 4A:
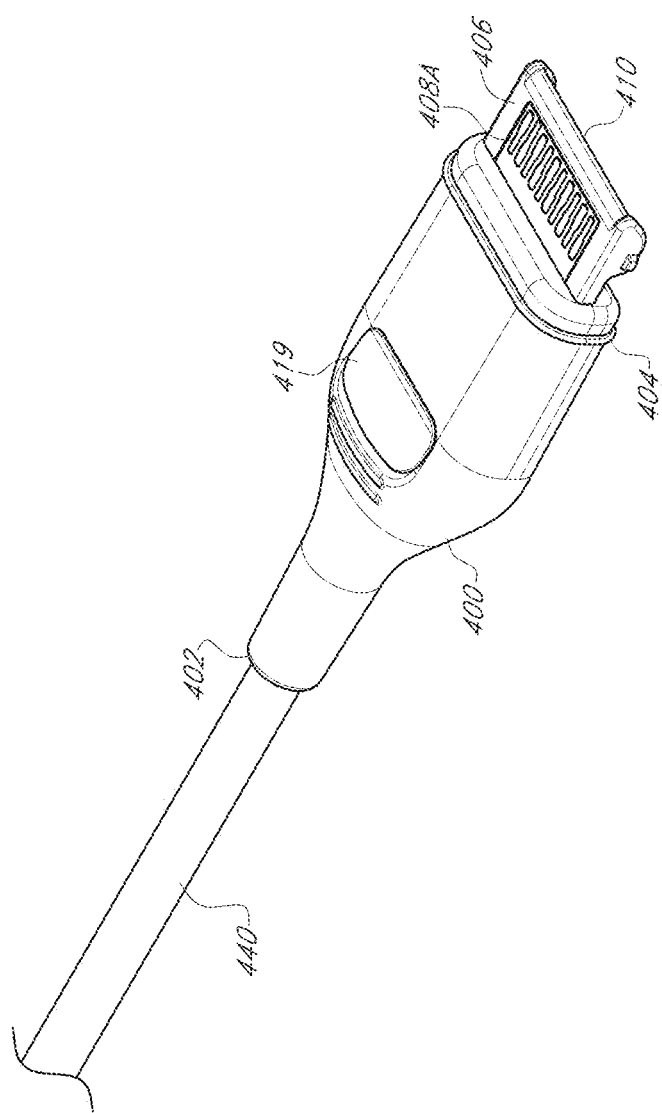
FIGS. 4A-4F are perspective, top, bottom, side, close-up, and front views of a male connector, according to some embodiments of the present disclosure.

FIGS. 4A-4F illustrates a connector 400. The connector 400 is an example of the male connector 110 described above with respect to FIG. 1. Referring to FIG. 4A, the connector 400 can include a rib 404 and a first insertion portion 406. The connector 400 can be attached to a cable 440. As described herein, insertion of the connector 400 into a female connector can cause the rib 404 to come in contact with a surface of the female connector that creates positive interference and/or a seal, which may advantageously result in water resistance. The rib 404 can come into contact with an inner wall of the female connector, such as the connectors 820 and/or 920 of FIGS. 8L and 9B, respectively. The rib 404 may not be exposed when inserted into the female connector, which is described below with respect to FIGS. 12A and 12B.

The rib 404 is raised in one embodiment. The rib 404 can be a protrusion that circumferentially surrounds at least a portion of, or an entire circumference of, the connector 400. In surrounding a portion of the connector 400, the protrusion may have approximately consistent dimensions, such as an approximately consistent width and a height. Thus, the protrusion can correspond to a protruding ring surrounding the portion of the connector 400. As shown, the rib 404 can have a rounded outer shape. The curved outer shape of the rib 404 can further be approximately symmetrical. Additional details regarding the rib 404 are described below with respect to FIG. 4E.

In some embodiments, the outer material of the connector 400 starting at a point 402 after the cable 440 and including the rib 404, but excluding the exposed surface 419, can be pliable. The outer material of the connector 400 starting at the point 402 after the cable 440 and including the rib 404 may be an overmold. The overmold can include and/or can be made of thermoplastic elastomer. The rib 404 possibly including and/or being made of a thermoplastic elastomer may provide further advantages by allowing for variances in the manufacturing process of the rib 404 while still being capable of forming a water resistant seal. A manufacturing process may result in the rib 404 being taller than the manufacturing specifications. A greater insertion force may then be needed; however, the functionality of the connector may not be adversely affected since a water resistant seal may still be formed with the taller rib 404 when inserted. Conversely, if the rib 404 is slightly shorter than manufacturing specifications, the insertion force may be reduced, but the connector 400 may maintain some water resistance. In other embodiments, the outer material of the connector 400 starting at the point 402 after the cable 440 and up to the rib 404 can be rigid and the material of the rib 404 can be pliable.

The first insertion portion 406 can include one or more contacts, such as a first set of contacts 408A, and a proximal end 410. Example contacts, such as the first set of contacts 408A, are electrical contacts and/or contact pads. In some embodiments, the first set of contacts 408A can be disposed on a circuit board and can be operative to contact another set of electrical contacts in a corresponding female connector of a patient monitor when the male connector 400 is inserted into the female connector. A second set of contacts may be on the bottom side of the first insertion portion 406, which is described below respect to FIG. 4C. The connector 400 can include 20 contact pads, such as 10 contact pads for the first set of contacts 408A and another 10 contact pads for the second set of contacts. In some embodiments, all of the contact pads are electrically active, and, in other embodiments, only a subset of the contact pads may be active and used to communicate with sensor signals. Only 8 or 9 contact pads may be active. Some of the contacts may transmit data for physiologically monitoring sensors, which may include a SpO2 sensor and/or an acoustic respiration sensor. Example contacts include, but are not limited to, emitters, anodes, cathodes, shields and/or may be used for electrically erasable programmable read-only memory (EE-PROM) data, temperature data, and/or thermistor data.

The proximal end 410 can be wedge shaped. In some embodiments, the wedge shaped proximal end 410 advantageously reduces the insertion force required to spread the spring contacts of a female connector, as described herein. Other shapes for the proximal end 410 can include, but are not limited to, a curved shape, a rectangular shape, or shape that is narrower at the apex and wider at the base.

Figure 4B:
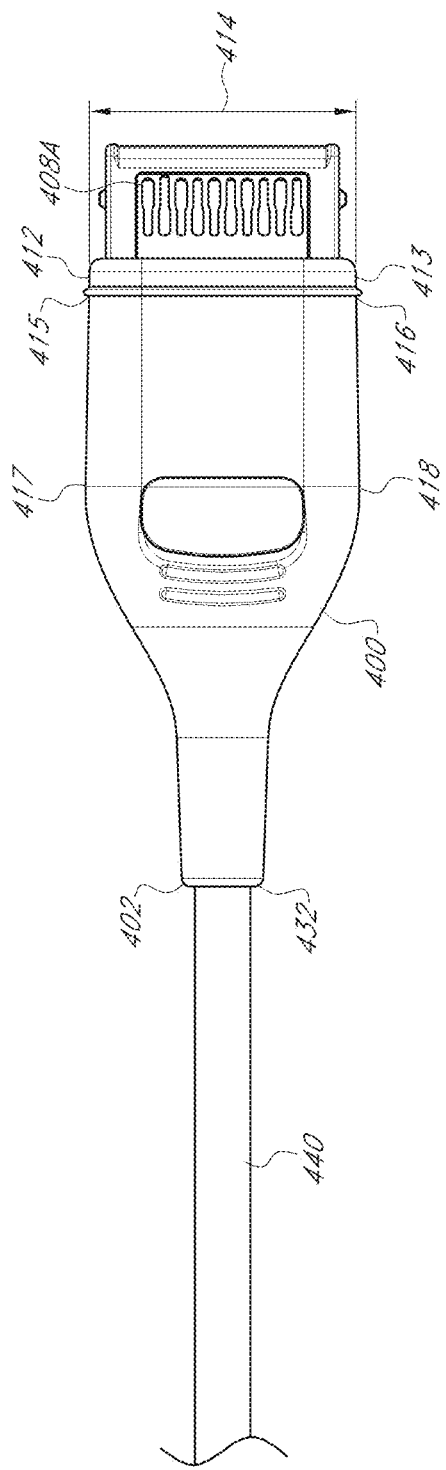

FIG. 4B illustrates a top view of the connector 400. In some embodiments, the portion of the connector 400 at the edge points 412 and 413 (e.g., between the rib and the first insertion portion 406) is the width measurement 414, which can be approximately 2.06 centimeters (0.81 inches). The width measurement 414 can be between approximately 2.03 centimeters (0.8 inches) and approximately 2.06 centimeters (0.81 inches). In other embodiments, the width measurement 414 can be between approximately 2.01 centimeters (0.79 inches) and approximately 2.08 centimeters (0.82 inches). In yet further embodiments, the width measurement 414 can be between approximately 2.01 centimeters (0.79 inches) and approximately 2.29 centimeters (0.9 inches).

The connector 400 can include a draft angle. The connector 400 can include a first portion and a second portion of the overmold. The first portion of the overmold is between the contacts 408A and the second portion of the overmold. The second portion of the overmold is adjacent to the cable 440. The first portion of the overmold corresponds to the area within and including the points 415, 416, 417, and 418 before the contacts 408A, and/or the second portion of the overmold corresponds to the area within and including the points 402, 417, 418, and 432 adjacent to the cable 440. A width of the proximal end of the first portion (points 415 and 416) may be narrower than a width of the distal end of the first portion (points 417 and 418). The first portion, which corresponds to the points 415, 416, 417, and 418 before the contacts 408A, can be tapered.

In some embodiments, the width of the proximal end of the first portion (points 415 and 416) can be approximately 2.03 centimeters (0.8 inches) and the width of the distal end of the first portion (points 417 and 418) can be approximately 2.08 centimeters (0.819 inches). The width of the proximal end of the first portion (points 415 and 416) can be between approximately 2.03 centimeters (0.8 inches) and approximately 2.06 centimeters (0.81 inches), and the width of the distal end of the first portion (points 417 and 418) can be between approximately 2.06 centimeters (0.811 inches) and approximately 2.08 centimeters (0.82 inches). In other embodiments, the width of the proximal end of the first portion (points 415 and 416) can be between approximately 1.98 centimeters (0.78 inches) and approximately 2.06 centimeters (0.81 inches), and the width of the distal end of the first portion (points 417 and 418) can be between approximately 2.06 centimeters (0.811 inches) and approximately 2.10 centimeters (0.825 inches).

A ratio of the width of the proximal end of the first portion (points 415 and 416) relative to the width of the distal end of the first portion (points 417 and 418) can be approximately 97.68/100. The width of the proximal end of the first portion (points 415 and 416) may be approximately 97.68% of the width of the distal end of the first portion (points 417 and 418). The width of the proximal end of the first portion (points 415 and 416) can be between approximately 97% and approximately 98% the width of the distal end of the first portion (points 417 and 418). In other embodiments, the width of the proximal end of the first portion (points 415 and 416) can be between approximately 96% and approximately 99% the width of the distal end of the first portion (points 417 and 418).

In some embodiments, the draft angle between the proximal end and the distal end of the first portion (points 415 and 417 and/or points 416 and 418) can be approximately 1.43 degrees. The draft angle between the proximal end and the distal end of the first portion (points 415 and 417 and/or points 416 and 418) can be between approximately 1.4 degrees and approximately 1.46 degrees. In other embodiments, the draft angle between the proximal end and the distal end of the first portion (points 415 and 417 and/or points 416 and 418) can be between approximately 1.33 degrees and approximately 1.53 degrees. In yet further embodiments, the draft angle between the proximal end and the distal end of the first portion (points 415 and 417 and/or points 416 and 418) can be between approximately 1 degree and approximately 2 degrees.

Figure 4C:
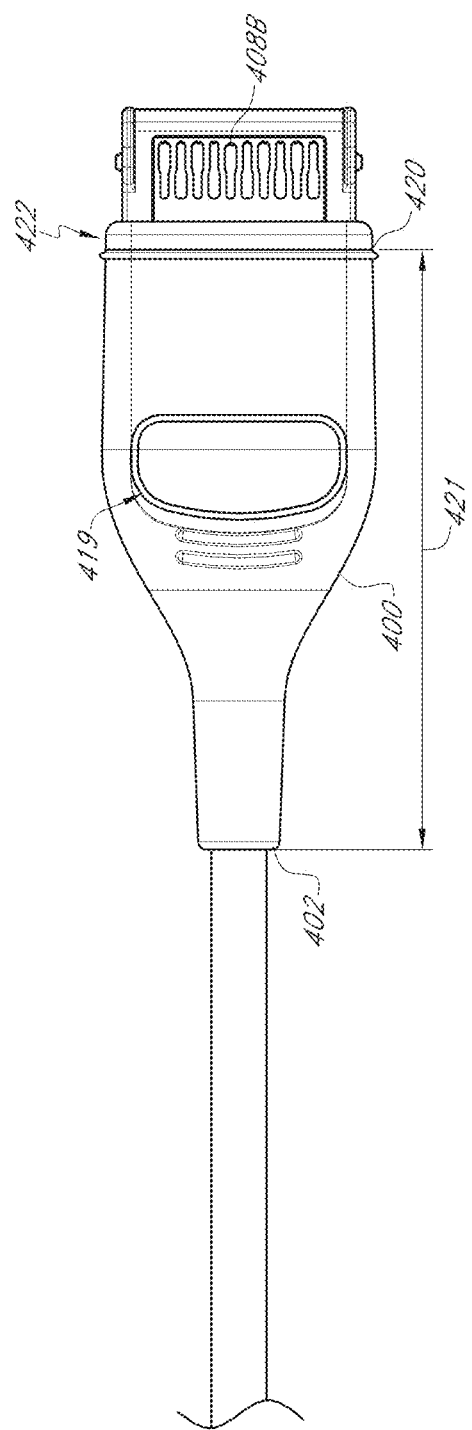

FIG. 4C illustrates a bottom view of the connector 400. The bottom of the connector 400 can include a second set of contacts 408B. The second set of contacts 408B can include contact pads, such as 10 contact pads, which may be similar to the first set of contacts 408A. In some embodiments, the portion of the connector 400 at the points 402 and 420 between the cable and the contacts 408B can be the length measurement 421, which can be approximately 4.52 centimeters (1.78 inches) and/or approximately 4.62 centimeters (1.82 inches). The length measurement 421 can be between approximately 0.52 centimeters (1.78 inches) and approximately 4.62 centimeters (1.82 inches). In other embodiments, the length measurement 421 can be between approximately 4.50 centimeters (1.77 inches) and approximately 4.55 centimeters (1.79 inches). In yet further embodiments, the length measurement 421 can be between approximately 4.60 centimeters (1.81 inches) and approximately 4.65 centimeters (1.83 inches). In yet even further embodiments, the length measurement 421 can be between approximately 1.40 centimeters (0.55 inches) and approximately 5.08 centimeters (2 inches). In some embodiments, the exposed surface 419 on the bottom of the connector 400 may be the same material as the exposed proximal portion 422. These exposed surfaces and/or portions may correspond to the frame 510 of FIG. 5A. An exposed surface on the top of the connector 400 may be similar to the exposed surface 419. In some embodiments, the first set of contacts 408A and/or second set of contacts 408B advantageously may not be energized until the contacts 408A and/or 408B are inserted into the female connector. Since the contacts 408A and/or 408B may not be energized until inserted, the exposed contacts 408A and/or 408B may be safely touched by a patient or clinician without transmitting electricity to the person or shocking the person.

Figure 4D:
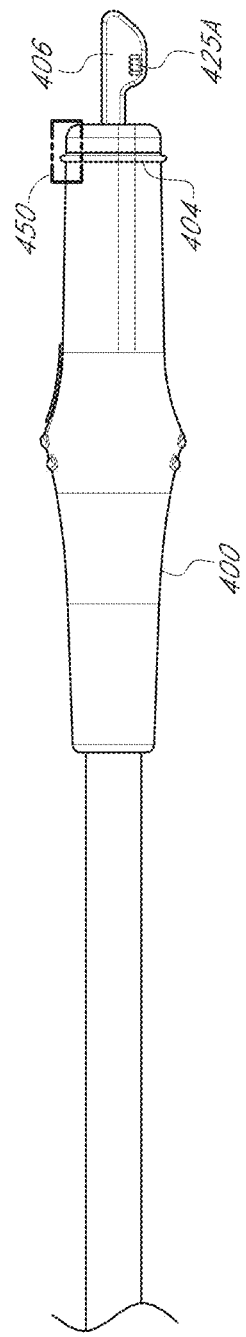

FIG. 4D illustrates a side view of the connector 400. The first insertion portion 406 of the connector 400 can include a detent 425A. The detent 425A can engage with a portion of a female connector. The detent 425A may advantageously provide a securing mechanism to hold the connector 400 in place while inserted into a female connector. Thus, the connector 400 may be less likely to be inadvertently removed from a female connector when the detent 425A is engaged. The detent 425A may also advantageously provide positive feedback to a user (such as a snap sensation feedback) to indicate when the connector 400 has been properly inserted into a female connector. The area 450 of the connector 400 includes the rib 404, which is described below with respect to FIG. 4E.

In other embodiments, a different detent mechanism may be used other than what is shown in FIG. 4D. Additional example detents and/or detent mechanisms include other catches, pins, and/or spring-operated devices, such as spring-operated balls.

Figure 4E:
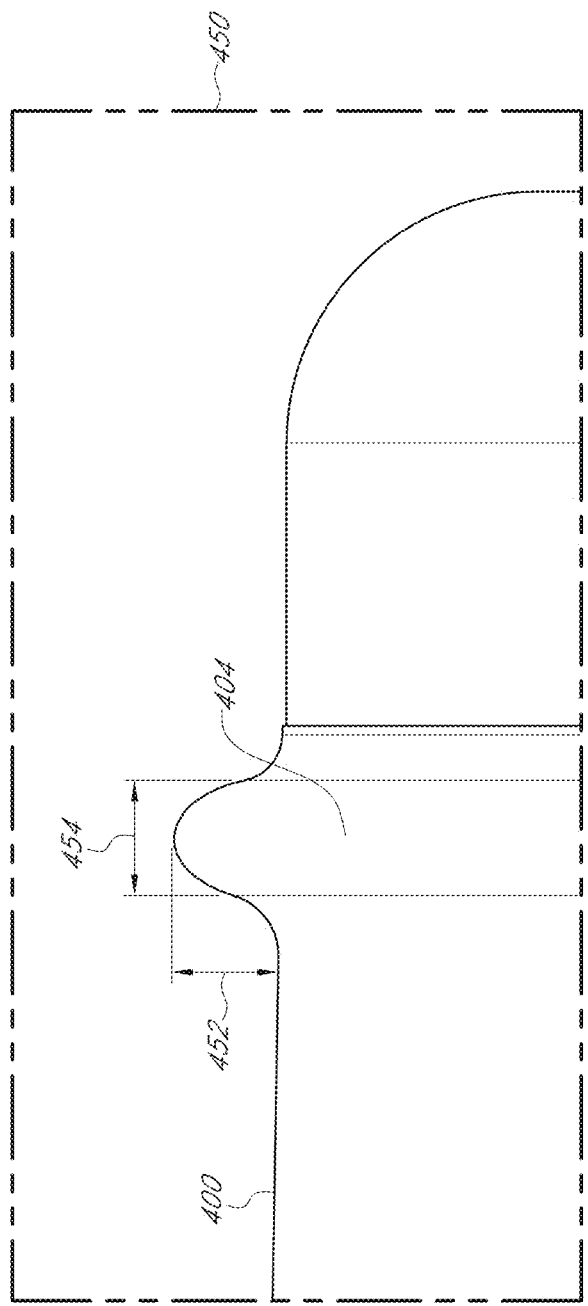

FIG. 4E illustrates a close-up side view of the connector 400. The area 450 of FIG. 4E may correspond to the area 450 of FIG. 4D. The close-up side view shows the rib 404 of the connector 400. The rib 404 can correspond to a ring surrounding a portion of the connector 400. As shown, the rib 404 can have a rounded outer shape, which may be approximately symmetrical.

The rib 404 may have approximately consistent dimensions, such as an approximately consistent width and a height. In some embodiments, the width 454 of the rib 404 can be between approximately 0.762 millimeters (0.03 inches) and approximately 0.8128 millimeters (0.032 inches), and/or the height 452 of the rib 404 can be between approximately 0.254 millimeters (0.01 inches) and approximately 0.508 millimeters (0.02 inches). The height 452 of the rib 404 can be between approximately 0.254 millimeters (0.01) inches and approximately 0.762 millimeters (0.03 inches). In other embodiments, the height 452 of the rib 404 can be between approximately 0.254 millimeters (0.01 inches) and approximately 1.016 millimeters (0.04 inches). In yet further embodiments, the height 452 of rib 404 can be between approximately 0.254 millimeters (0.01 inches) and approximately 1.27 millimeters (0.05 inches). The width 454 of the rib 404 can be between approximately 0.762 millimeters (0.03 inches) and approximately 1.016 millimeters (0.04 inches). In other embodiments, the width 454 of the rib 404 can be between approximately 0.762 millimeters (0.03 inches) and approximately 0.8128 millimeters (0.032 inches), and the height 452 of the rib 404 can be between approximately 0.762 millimeters (0.03 inches) and approximately 0.8128 millimeters (0.32 inches).

Figure 4F:
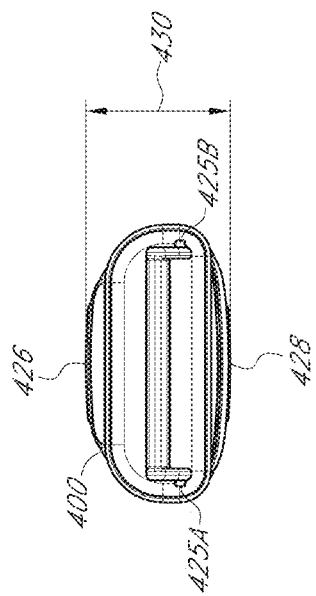

FIG. 4F illustrates a front view of the connector 400. The connector 400 can include the detents 425A and 425B. In FIG. 4F, the front view of the connector 400 illustrates the detents 425A and 425B. As described above with respect to FIG. 4D, the detent 425A can engage with a portion of a female connector. The detent 425B may be similar to the detent 425A and the detent 425B can engage with another portion of the female connector. In some embodiments, the portion of the connector 400 at the bottom and top points 426 and 428 can be the height measurement 430, which can be approximately 1.12 centimeters (0.44 inches). The height measurement 430 can be between approximately 1.12 centimeters (0.44 inches) and approximately 1.14 centimeters (0.45 inches). In other embodiments, the height measurement 430 can be between approximately 1.02 centimeters (0.4 inches) and approximately 1.07 centimeters (0.42 inches). The height measurement 430 can be between approximately 1.02 centimeters (0.4 inches) and approximately 1.12 centimeters (0.44 inches). The height measurement 430 can be between approximately 1.02 centimeters (0.4 inches) and approximately 1.27 centimeters (0.5 inches). Although many measurements are described herein, each measurement is an example, and other sizes of components can be used. For instance, the scale of any of the components here may be shrunk or enlarged to include similar proportions. Or, a subset of the components described herein may be sized differently.

In some embodiments, as shown in FIGS. 4A-4F, the overmold of the connector 400 can cover a portion of the frame and a portion of the circuit board but may not cover the electrical contacts 408A and 408B. The electrical contacts 408A and 408B may be open to air when the connector 400 is disconnected from a female connector of a patient monitor. The rib 404 can be raised and can be disposed on the overmold of the connector 400. The rib 404 can be a part of the overmold of the connector 400. As shown in FIGS. 4A-4F, the rib 404 can circumferentially surround the overmold. The rib 404 can create a seal with the female connector when the connector 400 is inserted into the female connector. When the connector 400 is inserted into the female connector, the electrical contacts 408A and 408B of the connector 400 may no longer be exposed to air, such that a water-resistant seal is created between the connector 400 and the female connector.

In some embodiments, the connector 400 is advantageously water resistant. The overmold, molding, a draft angle, and/or rib 404 may provide water resistance during an emergency situation involving water. The connector 400 can be inserted into female connector of a device that creates positive interference and/or a seal. The connected connector 400 and device may be dropped in a puddle and the device will not short circuit because of the water resistant features of the connector 400. Even if a disconnected connector 400 is dropped into a puddle or is sprayed with water, the water resistant features of the connector 400 may enable a clinician to shake and/or blow on the connector 400 to remove water. Thus, the clinician can then insert the connector 400, which was previously covered in water, into the female connector without a short circuit occurring.

Some connector embodiments may be different than the connector 400. Unlike the connector 400 of FIGS. 4A-4F, some connector embodiments do not include a rib yet may still provide some or all the water resistance functionality due to other features, such as a draft angle, a mold, and/or an overmold. The overmold can be configured to create a water-resistant seal with a female connector when the male connector is inserted into the female connector. When the male connector is inserted into the female connector, electrical contacts of the male connector may no longer be exposed to air, and a water-resistant seal can thereby be created between the male connector and the female connector. When the male connector is inserted into the female connector, positive resistance, such as friction, between the overmold (of the male connector) and the female connector can create a water-resistant seal. The draft angle of a male connector can create positive resistance to create a seal when the male connector is inserted into the female connector. A mold and/or an overmold of a male connector include materials that have low viscosity during their application and can flow in and fill in spaces that can create water resistant seals. In some embodiments, the one or more contacts of a male connector are covered. A cover over the contacts of a male connector can slide out of the way and/or retract when the male connector comes into contact with the female connector. In some embodiments, in addition or alternative to a male connector with an overmold, a male connector can include a silicone sheet that includes a slit that covers the one or more contacts. In some embodiments, when the male connector is inserted into the female connector, the contacts can push through the slit in the silicone sheet. Thus, the male connector with covered contacts and/or a silicone sheet may be water resistant.

Additionally or alternatively, some connector embodiments have different contacts, a different number of contacts, and/or a different insertion portion 406. Some connector embodiments do not have exposed surfaces on the bottom and/or top of the connector, such as the exposed surface 419.

FIGS. 5A-5E illustrate a connector assembly. The connector components of FIGS. 5A-5E are example components of the connector 400 described above with respect to FIGS. 4A-4F. FIGS. 5A-5E may further illustrate the steps of a connector assembly process, such as one or more blocks of the method 200 described below with respect to FIG. 2.

Figure 5A:
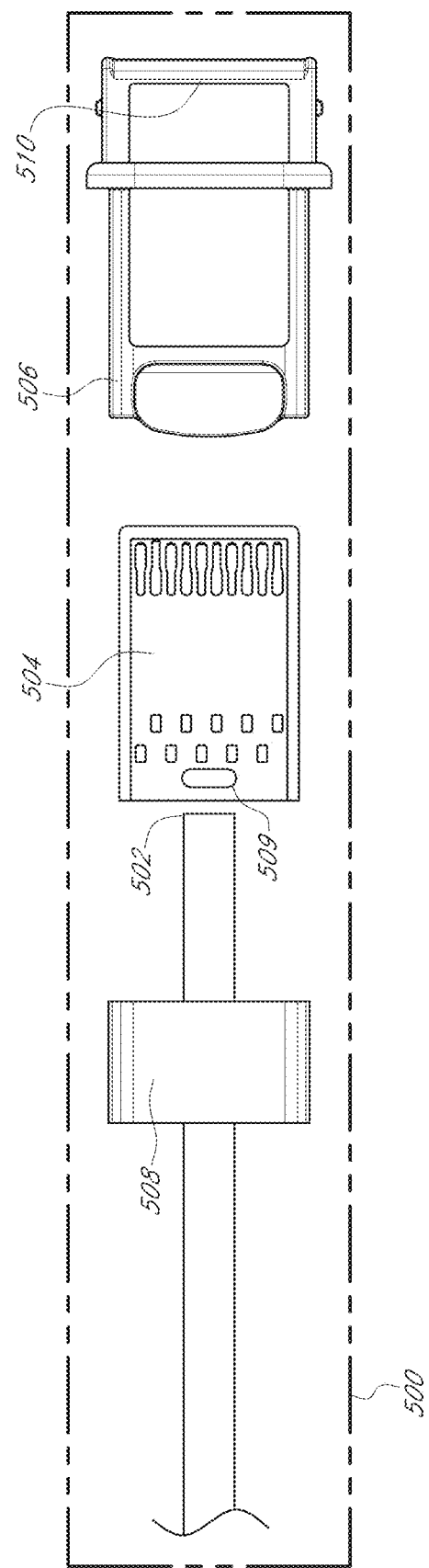
FIGS. 5A-5E are top exploded, top, and side views of male connector components, according to some embodiments of the present disclosure.

Referring to FIG. 5A, the top exploded view of the partial connector assembly 500 can include a cable 502, a circuit 504, a frame 506, and a shield 508. The circuit 504 can include an opening 509 in the distal portion of the circuit 504. The cable 502 can be attached to an opening 509 of the circuit 504. The cable 502 can include conductor strands (not illustrated). The cable 504 can include a fiber material and/or strands (not illustrated) that can be looped through the opening in the circuit 509. In some embodiments, the loop can be pulled snug to the circuit 504 and knotted. An adhesive, such as a drop of adhesive, can be applied to the connection between the cable 502 and the circuit 504, such as where the fiber material is connected to the circuit.

Figure 5B:
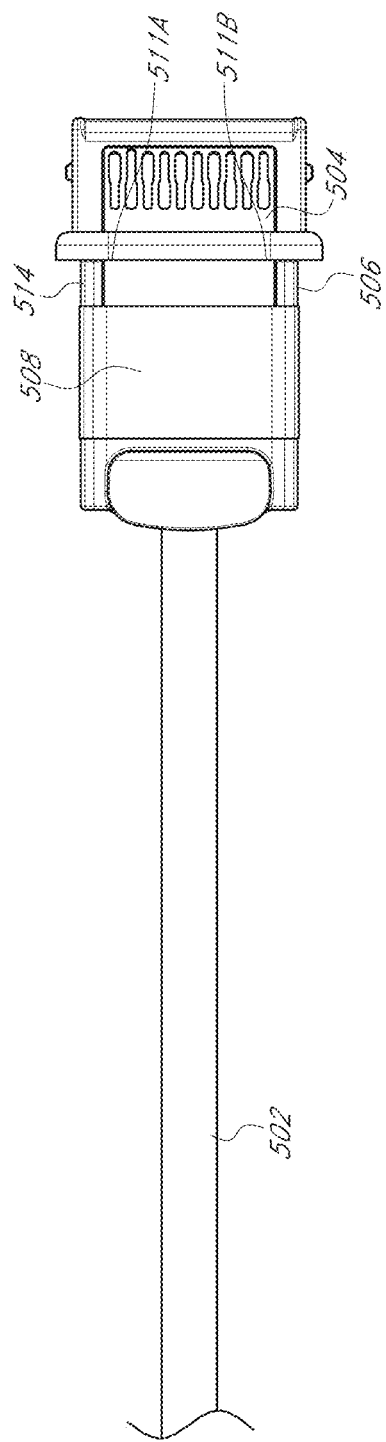

The circuit assembly including the circuit 504, which can be attached to the cable 502, can be inserted into the frame 506. In some embodiments, the frame 506 is rigid. The frame 506 can include and/or can be made of plastic, such as polycarbonate and/or a polycarbonate blend. An adhesive, such as a bead of adhesive, can be applied at an edge point 510 of the frame 506 to connect the circuit 504 to the frame 506. A bead of adhesive can be applied to the edge point 510 where a proximal portion of the frame 506 contacts to the proximal end of the circuit 504. As shown in FIG. 5B, the circuit board 504 can be disposed within the frame 506 and connected with the conductors in the cable 502.

Figure 5C:
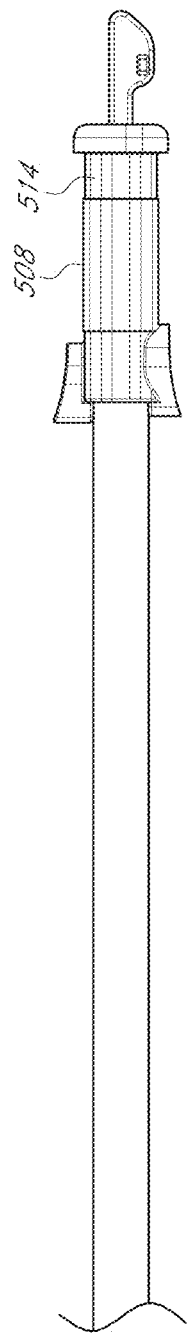

FIG. 5B illustrates a step in a connector assembly process to attach the shield 508 to the frame assembly 514. The shield 508 can include and/or can be made of copper. The shield 508 may advantageously reduce electromagnetic interference. In some embodiments, the cable strands (not illustrated) can be connected to the circuit 504 and/or the shield 508. A first set of cable strands can be soldered to the circuit 504 and a second set of cable strands can be soldered to the shield 508 (not illustrated). A drop of adhesive can be applied to each of the edge points 511A and 511B between the circuit 504 and the frame assembly 514. FIG. 5C illustrates a side view of the shield 508 attached to the frame assembly 514.

Figure 5D:
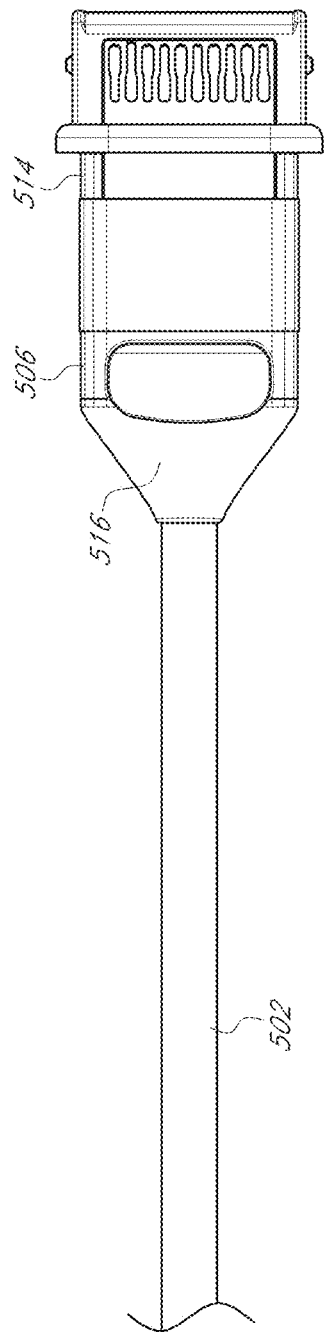
Figure 5E:
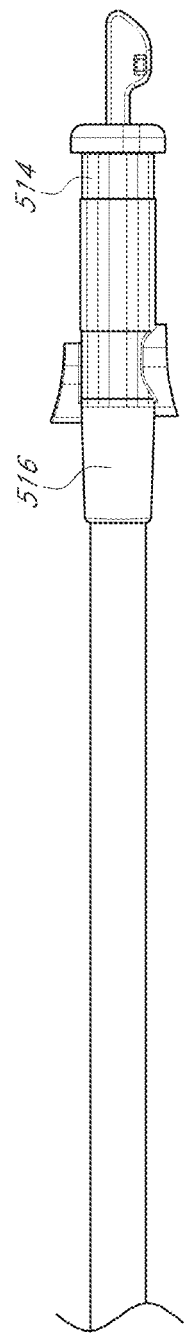

FIG. 5D illustrates another step in a connector assembly process to apply a covering. The inner covering 516, such as a mold, can be applied to the frame assembly 514. An inner covering 516 can include and/or can be made of a thermoplastic polymer, such as polypropylene. In some embodiments, the inner covering 516, such as an inner mold, can have a low viscosity during application and can flow in and fill in spaces of the frame assembly 514 well, which may advantageously improve sealing and/or water resistance. Thus, the inner covering 516 can seal a distal end of the frame 506 and a proximal end of the cable 502. The inner covering 516 can be between the cable 502 and the frame 506 and/or the frame assembly 514. The inner covering 516 can cover a portion of the cable 502. The inner covering 516 can be adjacent to the frame 506. The inner covering 516 can be located between the frame 506 and a distal end of the cable 502. At a later step in the process, the overmold can cover the inner covering 516 and/or other components of the connector, which may provide further water resistance. The connector 400 of FIGS. 4A-4F illustrates a completed connector with an overmold. FIG. 5E illustrates a side view of the inner covering 516 attached to the frame assembly 514.

Figure 6A:
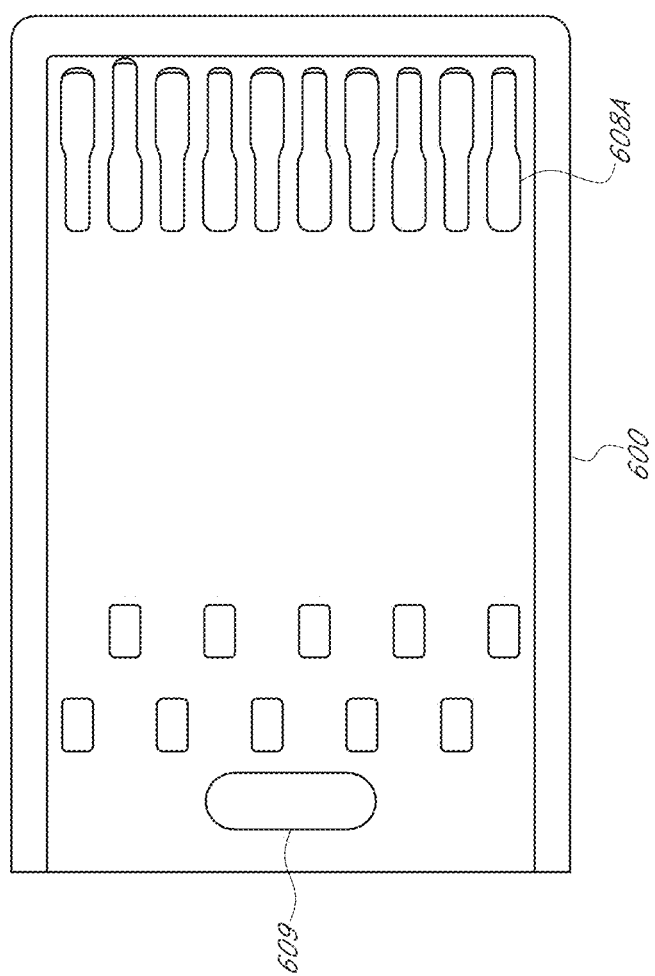
FIGS. 6A-6C are top, side, and bottom views of a circuit, according to some embodiments of the present disclosure.
Figure 6B:
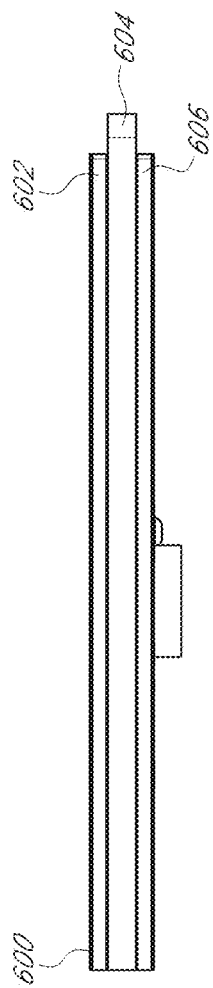
Figure 6C:
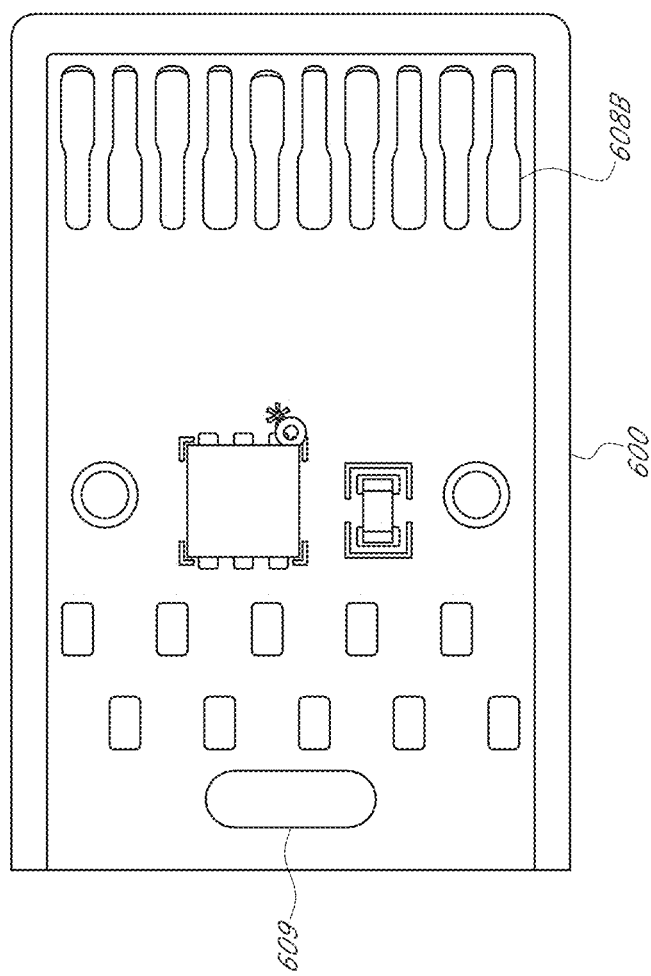

FIGS. 6A-6C illustrate a circuit. The circuit 600 is an example of the circuit 504 described above with respect to FIG. 5A. Referring to FIG. 6A, a top view of the circuit 600 is shown. The circuit 600 can include the opening 609 and a first set of contacts 608A. An example circuit is a circuit board, such as a printed circuit board (PCB). The circuit 600 can include multiple layers.

FIG. 6B illustrates a side view of the circuit 600. The circuit 600 can include a first and/or top layer 602, a second and/or middle layer 604, and a third and/or bottom layer 606. In some embodiments, the circuit 600 is a single multilayer assembly as opposed to separate circuit boards, and, therefore, the circuit 600 may be advantageously compact and space efficient. During the assembly process of a connector, the circuit 600 can slide into a frame of the connector assembly. The circuit 600 includes one or more ground planes. There may be a ground plane in and/or between the top layer 602 and the bottom layer 606. Turning to FIG. 6C, a bottom view of the circuit 600 is shown. The circuit 600 may include the opening 609 and a second set of contacts 608B.

Figure 7A:
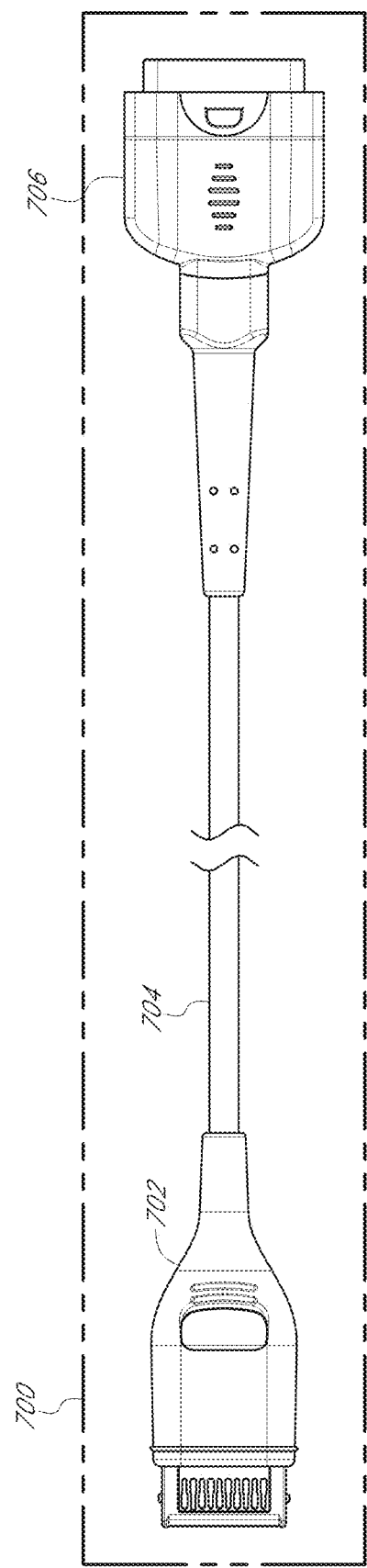
FIGS. 7A-7F are top, side, and back views of cable assemblies, according to some embodiments of the present disclosure.
Figure 7B:
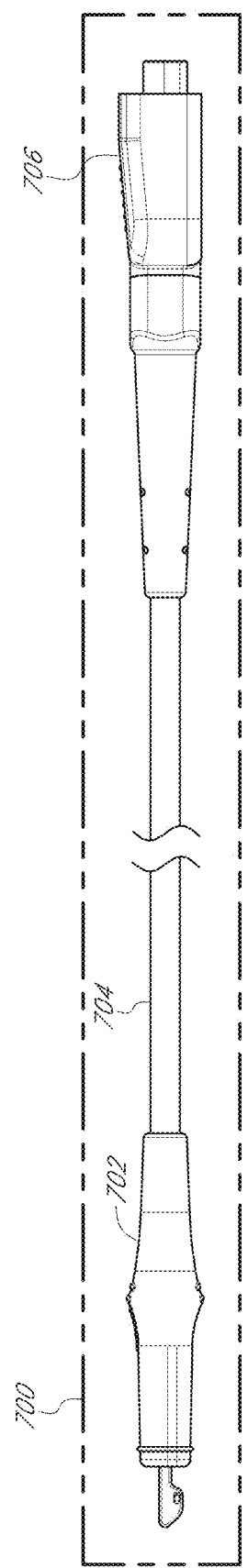
Figure 7C:
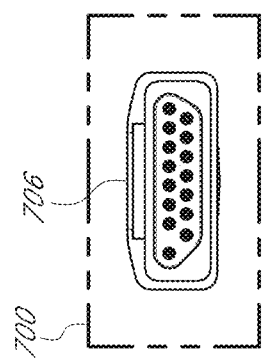

FIGS. 7A-7C illustrate a cable assembly. Referring to FIG. 7A, the top view of the cable assembly 700 can include a first connector 702, a cable 704, and a second connector 706. The first connector 702 is an example of the male connector 110 described above with respect to FIG. 1 and/or the male connector 400 described above with respect to FIGS. 4A-4F. The second connector 706 may connect to a sensor, such as a physiologically monitoring sensor. Turning to FIG. 7B, a side view of the cable assembly 700 is shown. Turning to FIG. 7C, a back view of the cable assembly 700 is shown. As shown, the second connector 706 may correspond or be similar to a commercially-available M15 connector to patient cable from Masimo Corp. In some embodiments, the cable assembly 700 includes a different second connector other than the one shown in FIGS. 7A-7C.

Figure 7D:
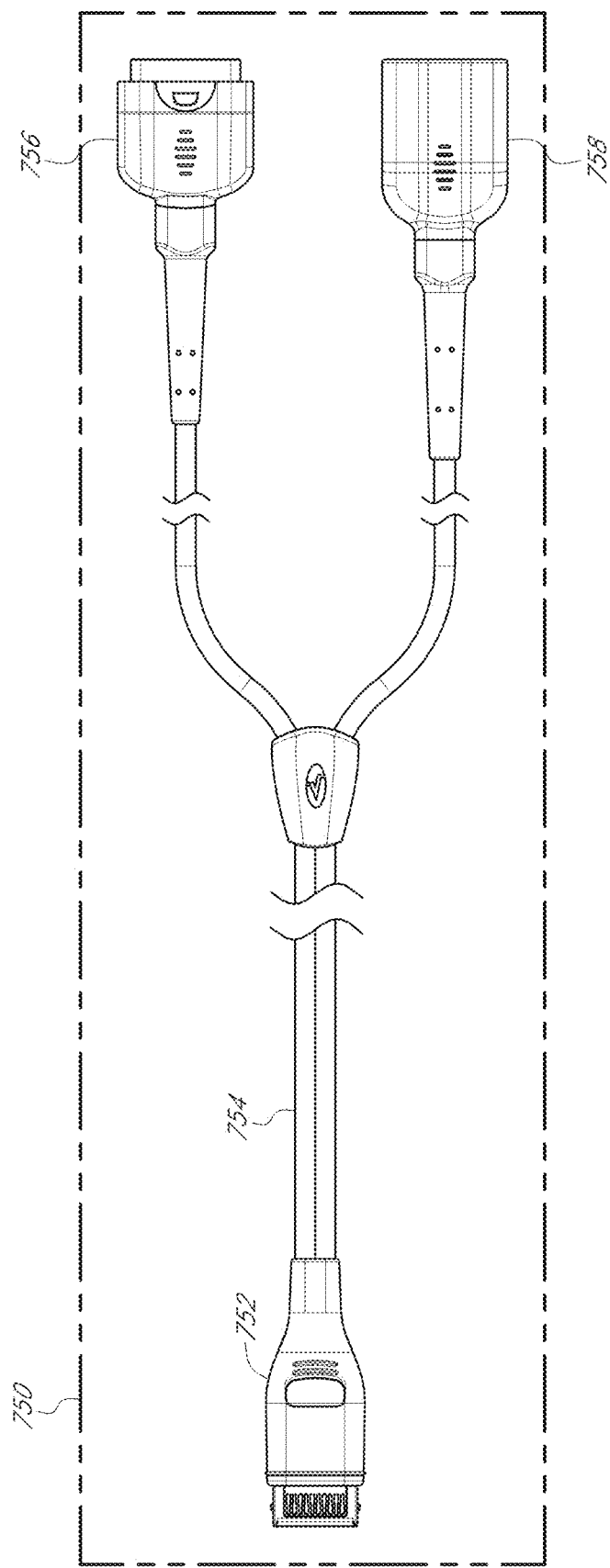
Figure 7E:
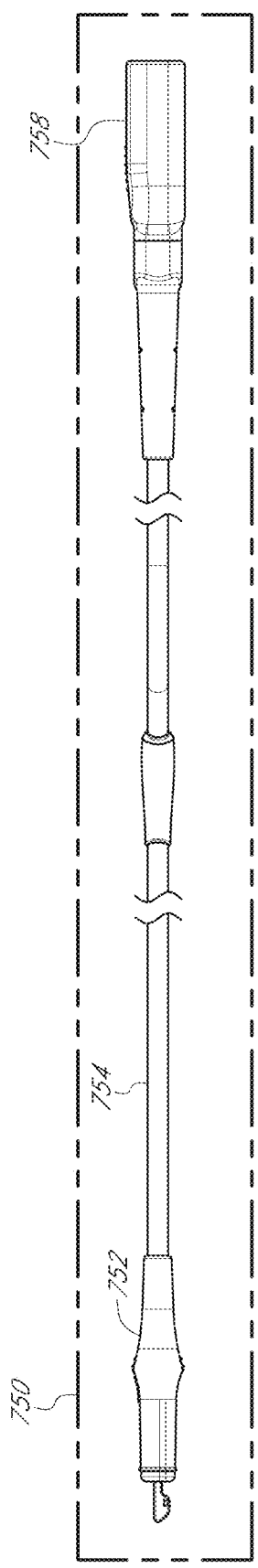
Figure 7F:
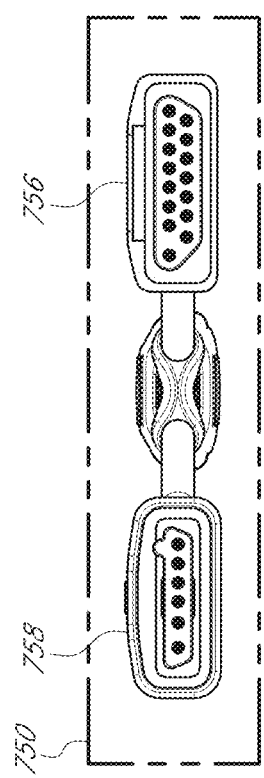

FIGS. 7D-7F illustrate another cable assembly. Referring to FIG. 7D, the top view of the cable assembly 750 can include a first connector 752, a dual cable 754, a second connector 756, and a third connector 758. The dual cable 754 can have dual channels. The first connector 752 is an example of the male connector 110 described above with respect to FIG. 1 and/or the male connector 400 described above with respect to FIGS. 4A-4F. The second connector 756 may be the same or similar to second connector 706 of FIGS. 7A-7C. Accordingly, the second connector 756 may connect to a sensor, such as a physiologically monitoring sensor. The second connector 758 may connect to another sensor, such as a physiologically monitoring sensor. Turning to FIG. 7E, a side view of the cable assembly 750 is shown. Turning to FIG. 7F, a back view of the cable assembly 750 is shown. As shown, the second connector 756 may correspond or be similar to a commercially-available M15 connector to patient cable from Masimo Corp. As shown, the third connector 758 can be different from the second connector 756. In some embodiments, the third connector 758 can correspond to an acoustic monitoring connector to cable, such as a commercially-available rainbow Acoustic Monitoring® (RAM™) connector to cable from Masimo Corp. In other embodiments, the cable assembly 750 includes different second and/or third connectors other than the ones shown in FIGS. 7D-7F.

IV. Female Connectors

Figure 8A:
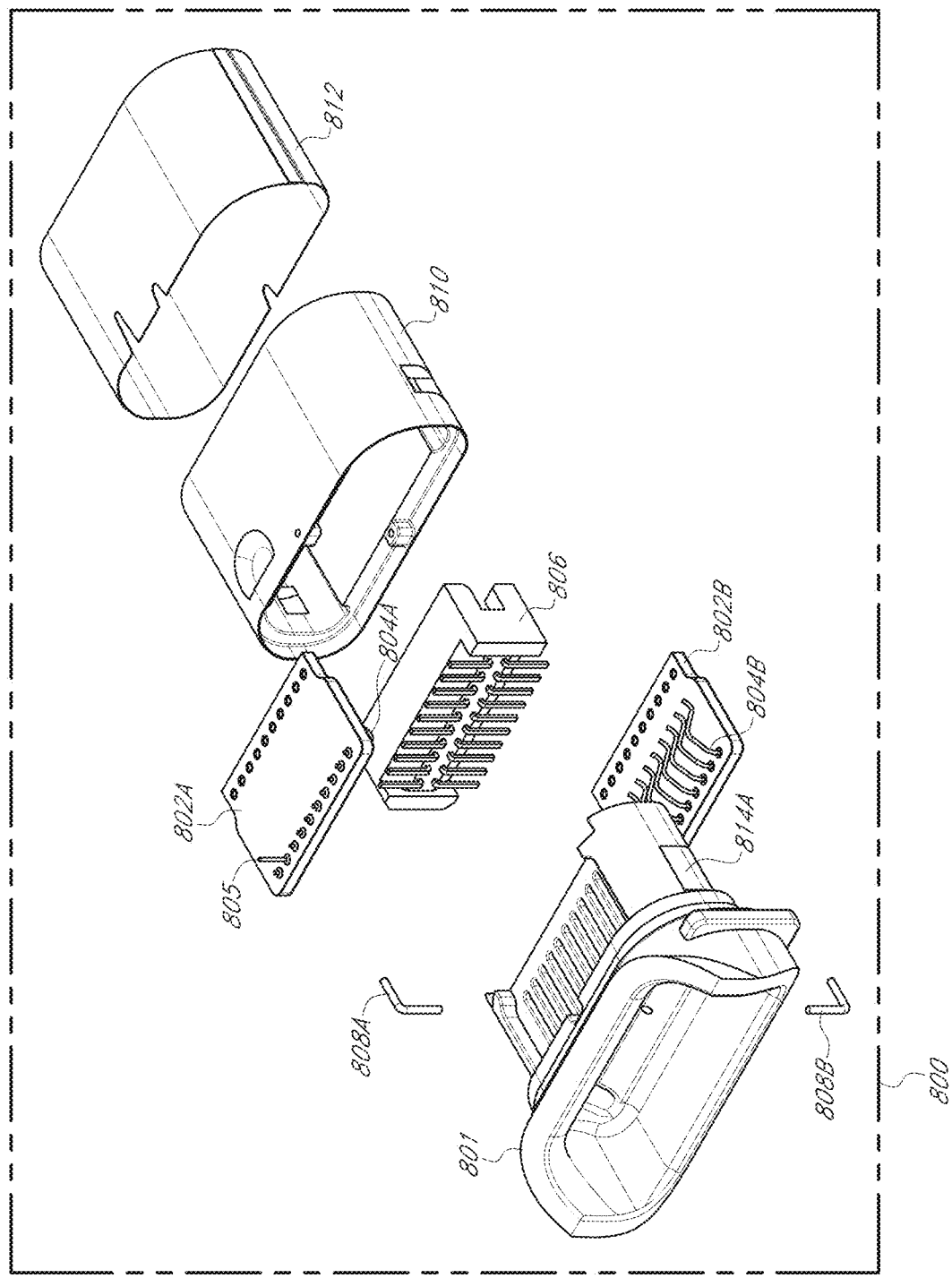
FIGS. 8A-8S are perspective exploded, top, bottom, side, front, back, perspective, and cross-section views of female connector components and a female connector, according to some embodiments of the present disclosure.
Figure 8B:
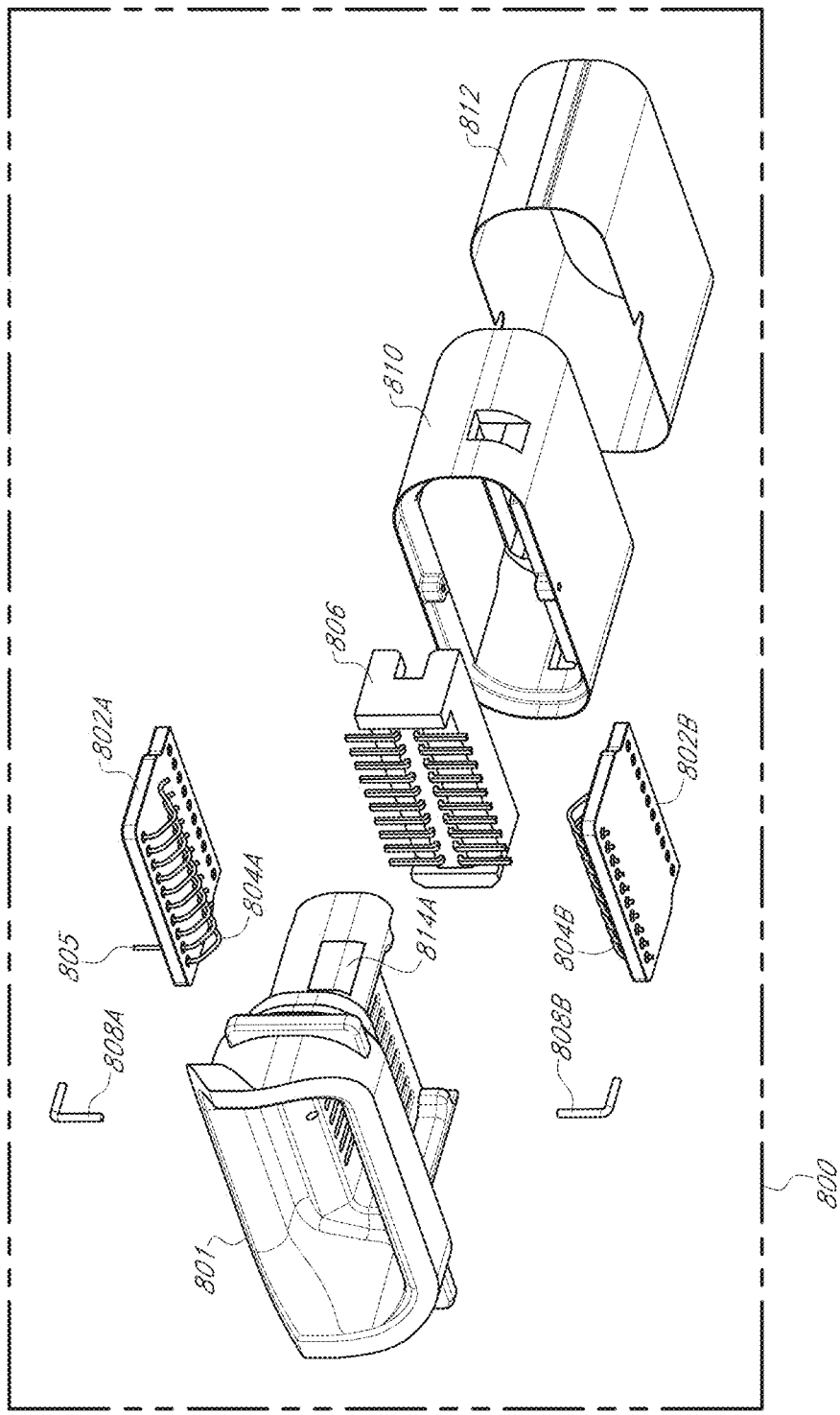

In FIGS. 8A-8B, exploded views of a connector assembly are shown. Referring to FIG. 8A, a top perspective exploded view of a connector assembly 800 is shown. The connector assembly 800 can include a frame 801, one or more boards 802A and 802B, a connector header 806, one or more electrostatic discharge pins 808A and 808B, a mold 810, and a shield 812. The frame 801 can include and/or can be made of plastic, such as polycarbonate and/or a polycarbonate blend. The frame 801 can include a cap 814A. The boards 802A and 802B can include one or more contacts 804A and 804B, respectively. The contacts 804A and 804B can include and/or can be spring contacts. The board 802B may differ from the board 802A in that the board 802B does not include a ground pin 805. The mold 810 can include and/or can be made of a thermoplastic polymer, such as polypropylene. The shield 812 can include and/or can be made of copper. Turning to FIG. 8B, a bottom perspective exploded view of the connector assembly 800 is shown.

Figure 8C:
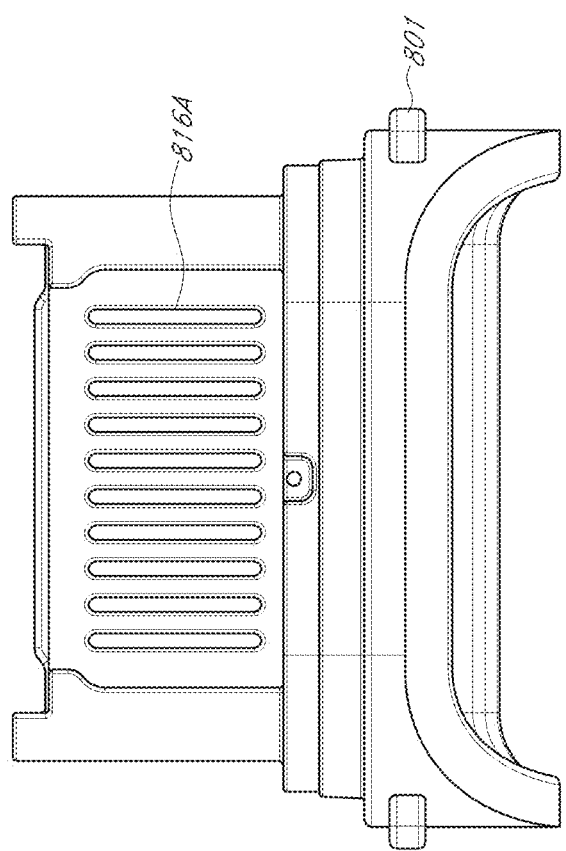
Figure 8D:
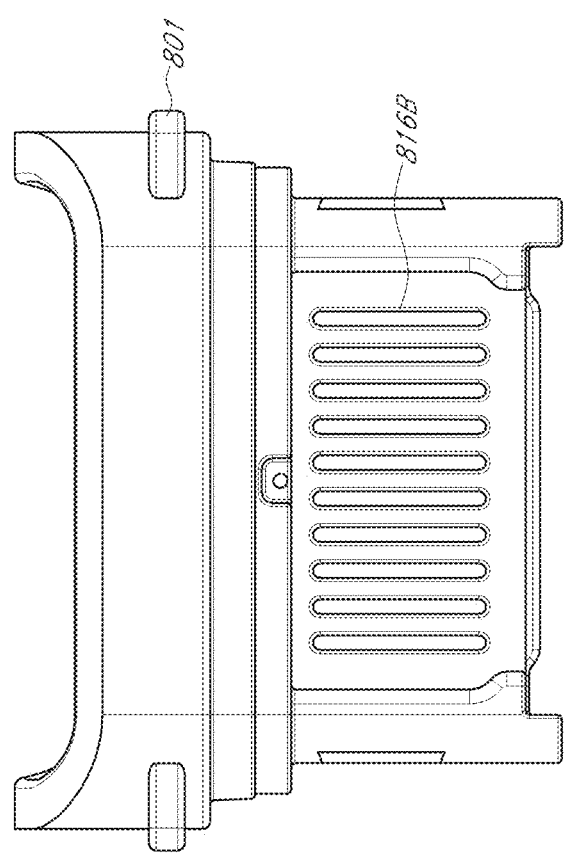
Figure 8E:
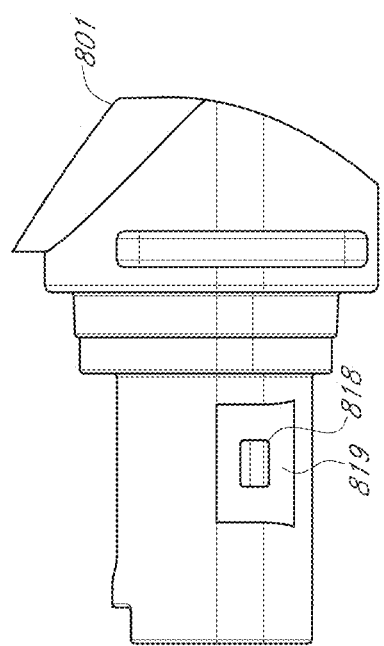

In FIGS. 8C-8E, views of the frame 801 are shown. FIG. 8C illustrates a top view of the frame 801. The frame 801 can include a first set of one or more openings 816A. FIG. 8D illustrates a bottom view of the frame 801. The frame 801 can include a second set of one or more openings 816B. FIG. 8E illustrates a side view of the frame 801. The frame 801 can include one or more recesses 819 and one or more detent holders 818. The detent holder 818 can include and/or can be an opening.

Figure 8F:
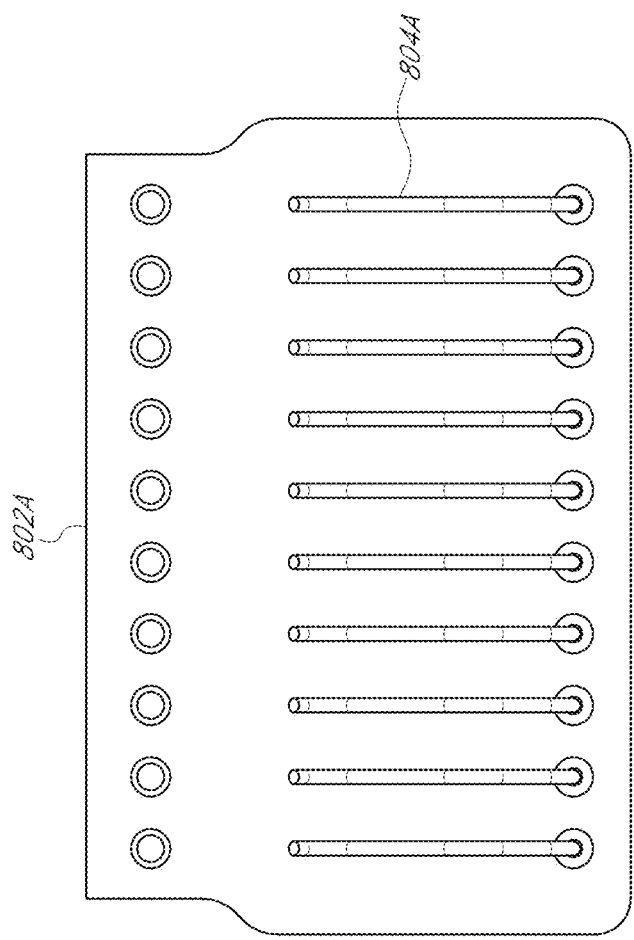
Figure 8G:
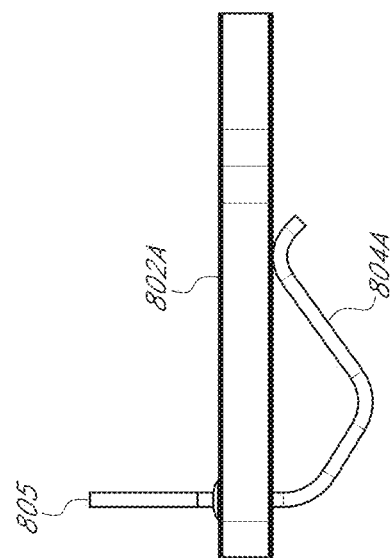

In FIGS. 8F and 8G, views of the board 802A are shown. FIG. 8F illustrates a bottom view of the board 802A that can include one or more contacts 804A. FIG. 8F illustrates a side view of the board 802A. The contacts 804A can be electrical. The one or more contacts 804A can be shaped to provide an elastic spring. Thus, when a male connector's contact pad is engaged with the contact 804A, the contact 804A can be compressed and when the contact pad is removed the contact 804A can return to its unengaged shape as shown in FIG. 8G.

Figure 8H:
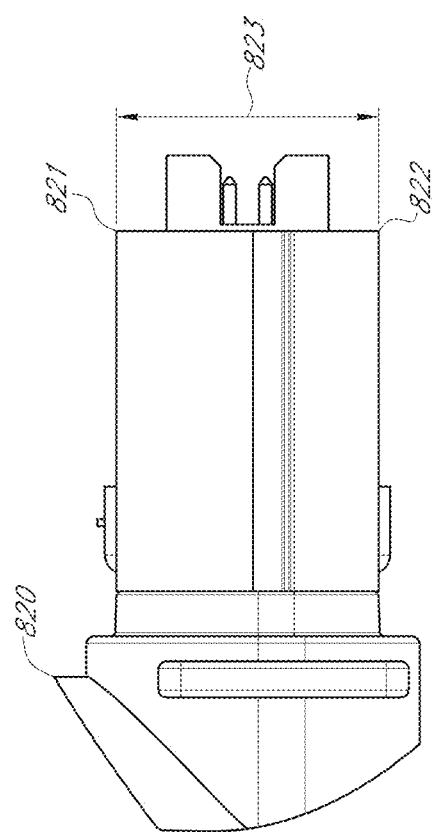

FIGS. 8H-8L illustrate another connector 820. The connector 820 is an example of the female connector 120 described above with respect to FIG. 1. The connector 820 is a non-exploded example of the connector assembly 800 described above with respect to FIGS. 8A and 8B. Referring to FIG. 8H, a side view of the connector 820 is shown. In some embodiments, the portion of the connector 820 at the top and bottom points 821 and 822 is the height measurement 823, which can be approximately 0.91 centimeters (0.36 inches). The height measurement 823 can be between approximately 0.89 centimeters (0.35 inches) and approximately 0.91 centimeters (0.36 inches). In other embodiments, the height measurement 823 can be between approximately 0.89 centimeters (0.35 inches) and approximately 0.94 centimeters (0.37 inches). In yet further embodiments, the height measurement 823 is between approximately 0.89 centimeters (0.35 inches) and approximately 1.02 centimeters (0.4 inches).

Figure 8I:
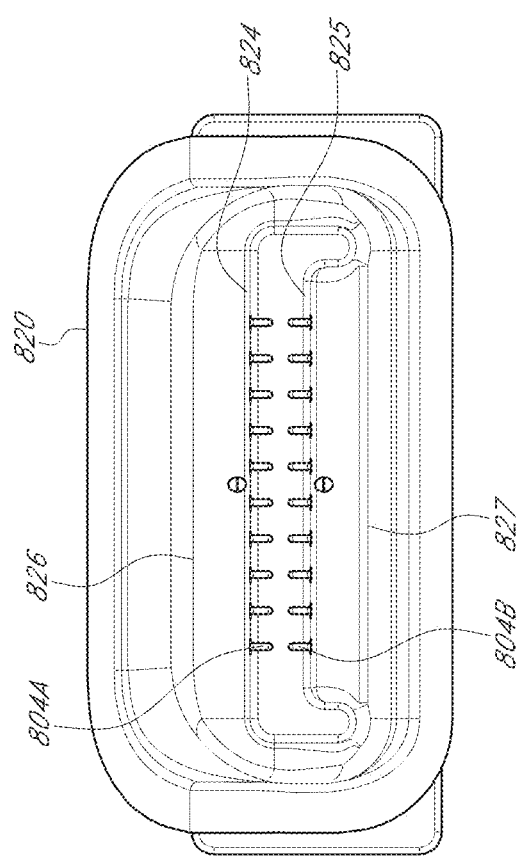

Turning to FIG. 8I, a front view of the connector 820 is shown. The connector 820 can include the top and bottom points 826 and 827 of a distal opening and other top and bottom points 824 and 825 of a proximal opening. The distal opening and the proximal opening can receive a male connector. In some embodiments, the height of the distal opening at the top and bottom points 826 and 827 can be between approximately 0.74 centimeters (0.29 inches) and approximately 0.76 centimeters (0.3 inches), and/or the height of the proximal opening at the other top and bottom points 824 and 825 can be between approximately 0.16 centimeters (0.063 inches) and approximately 0.18 centimeters (0.07 inches). In other embodiments, the height of the first distal opening at the top and bottom points 826 and 827 can be between approximately 0.74 centimeters (0.29 inches) and approximately 0.79 centimeters (0.31 inches), and/or the height of the proximal opening at the other top and bottom points 824 and 825 can be between approximately 0.15 centimeters (0.06 inches) and approximately 0.18 centimeters (0.07 inches). The height of the proximal opening at the other top and bottom points 824 and 825 can be between approximately 0.15 centimeters (0.06 inches) and approximately 0.19 centimeters (0.075 inches). In yet further embodiments, the height of the first distal opening at the top and bottom points 826 and 827 can be between approximately 0.74 centimeters (0.29 inches) and approximately 0.84 centimeters (0.33 inches), and/or the height of the proximal opening at the other top and bottom points 824 and 825 can be between approximately 0.15 centimeters (0.06 inches) and approximately 0.20 centimeters (0.08 inches). The proximal opening at the other top and bottom points 824 and 825 can include the contacts 804A and 804B. In some embodiments, the dimensions of the distal opening at the top and bottom points 826 and 827 and/or the dimensions of the proximal opening at the other top and bottom points 824 and 825 may advantageously prevent inadvertent touching of the contacts 804A and 804B. A person, such as a small child, may be unable to touch the contacts 804A and 804B with their finger due to the dimensions of the distal and/or proximal opening.

Figure 8J:
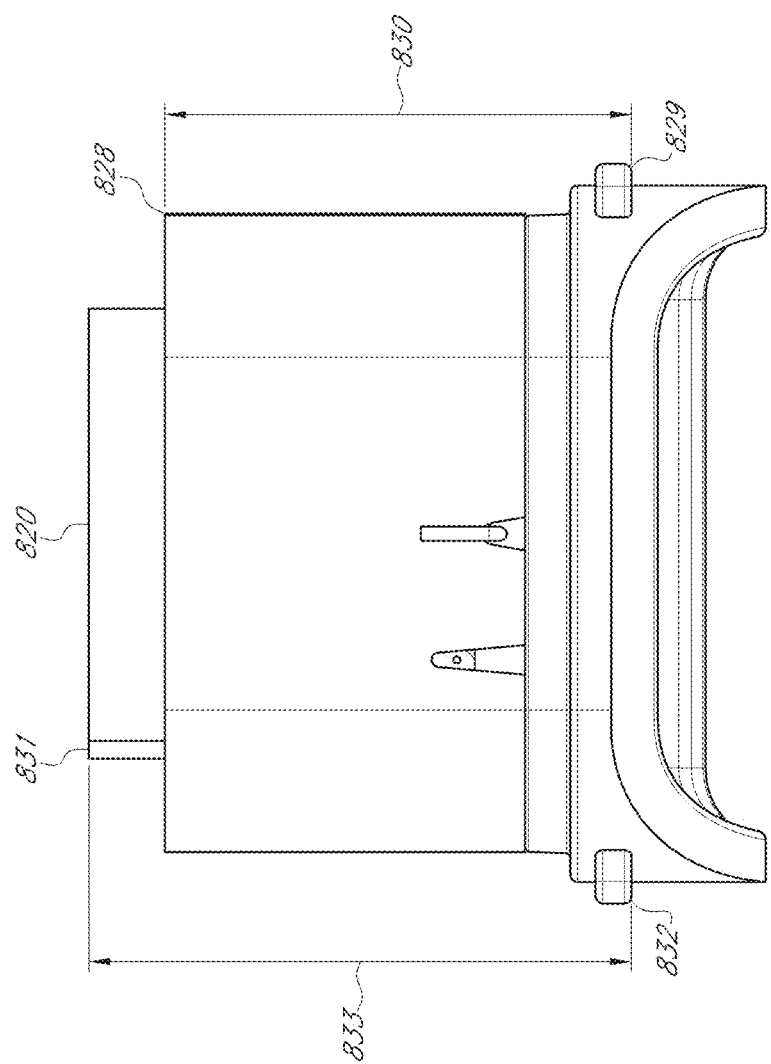
Figure 8K:
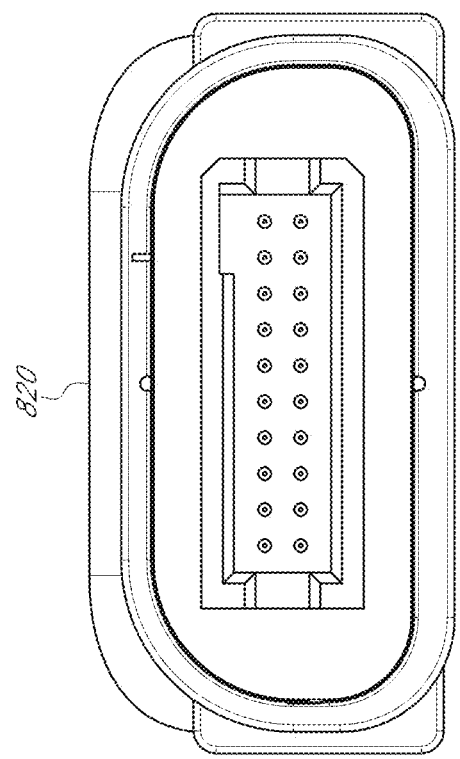

Turning to FIG. 8J, a top view of the connector 820 is shown. In some embodiments, the portion of the connector 820 at the proximal and distal points 828 and 829 is the length measurement 830, which can be approximately. 65 inches. The length measurement 830 can be between approximately 1.65 centimeters (0.65 inches) and approximately 1.91 centimeters (0.75 inches). In other embodiments, the length measurement 830 can be between approximately 1.65 centimeters (0.65 inches) and approximately 2.16 centimeters (0.85 inches). The portion of the connector 820 at the distal and proximal points 831 and 832 is the length measurement 833, which can be approximately 1.91 centimeters (0.75 inches). The length measurement 833 can be between approximately 1.91 centimeters (0.75 inches) and approximately 2.16 centimeters (0.85 inches). In other embodiments, the length measurement 833 can be between approximately 1.91 centimeters (0.75 inches) and approximately 2.41 centimeters (0.95 inches). In FIG. 8K, a back view of the connector 820 is shown.

Figure 8L:
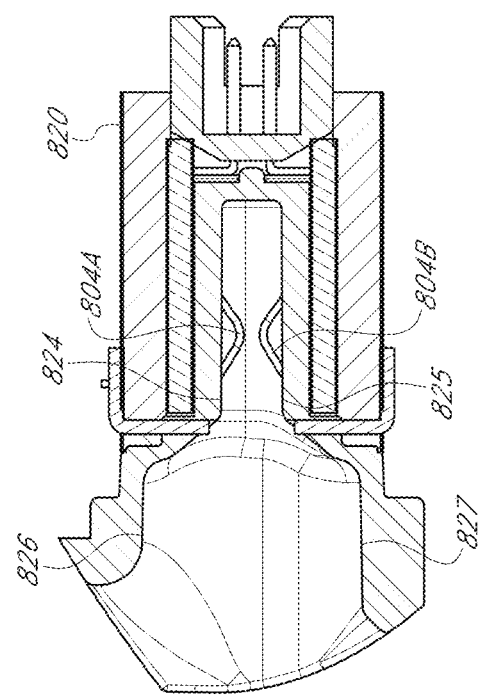

Turning to FIG. 8L, a cross-section view of the connector 820 is shown. The components and/or dimensions of the connector 820 shown and described above with respect to FIG. 8I may be similar to the components and/or dimensions of the connector 820 in FIG. 8L. The connector 820 can include the top and bottom points 826 and 827 of a distal opening and other top and bottom points 824 and 825 of a proximal opening. The proximal opening at the other top and bottom points 824 and 825 can include the contacts 804A and 804B. A rib of a male connector, such as the male connector 400 of FIG. 4A, may come into with a surface wall beginning at the top and bottom points 826 and 827 of the female connector 820.

Some connector embodiments may be different than the connector 820. Unlike the connector 820 of FIGS. 8H-8L, some connector embodiments include a covering over the opening to the contacts, such as a silicone sheet with a slit. A covering over the opening can be pliable. When a male connector is inserted into the female connector, the covering can partially or fully move and create a seal around the male connector.

Figure 8M:
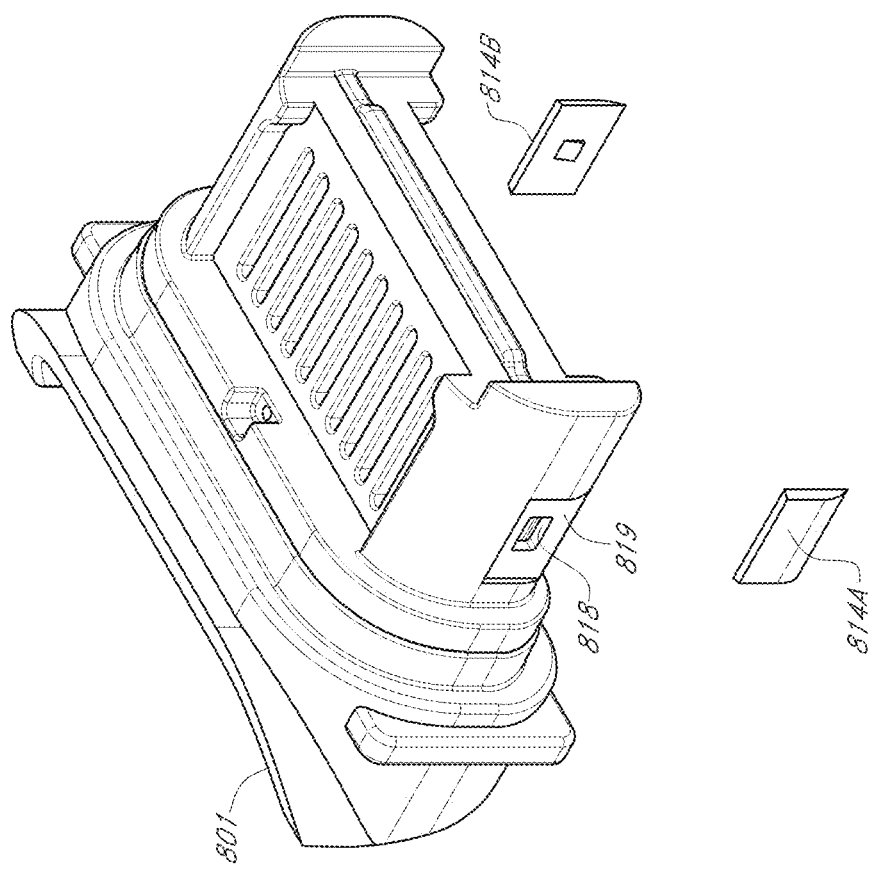
Figure 8N:
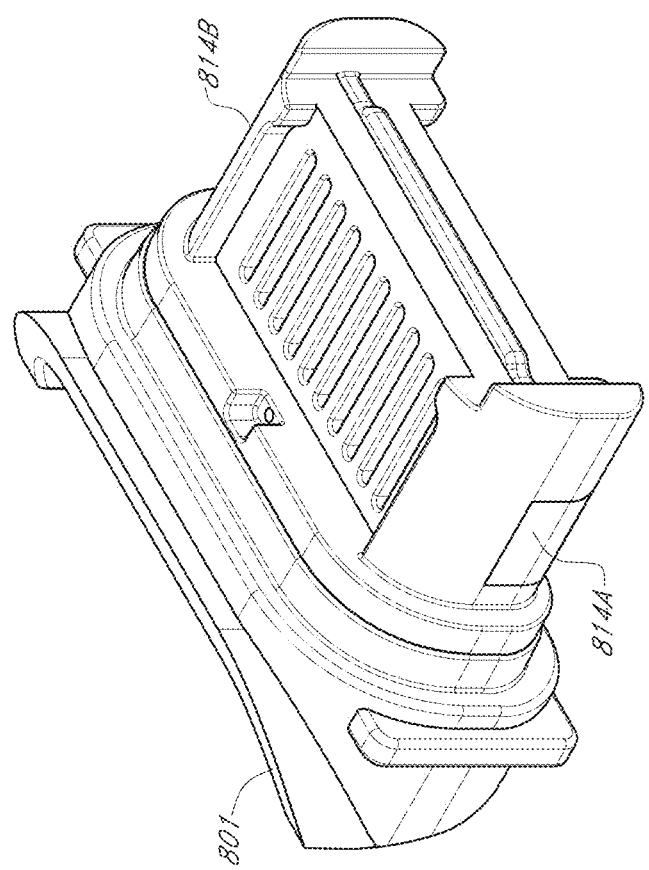
Figure 80:
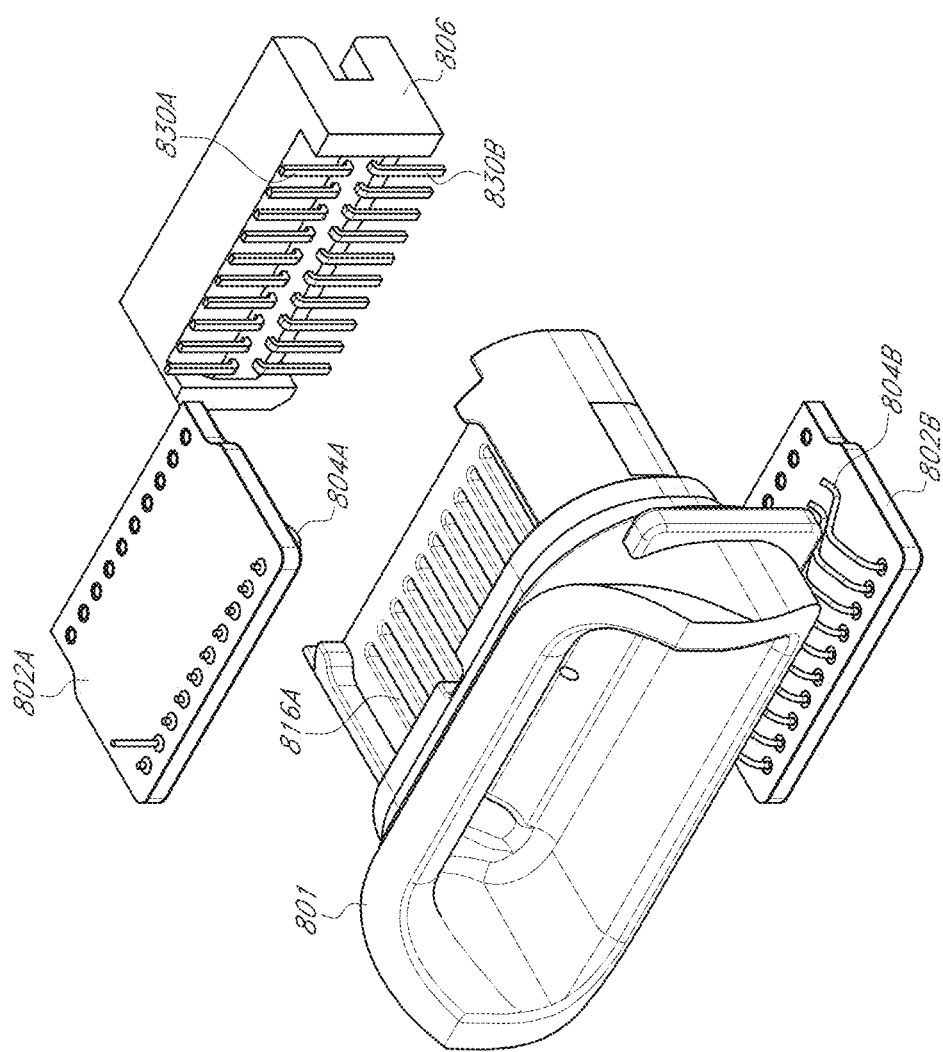

FIGS. 8M-8S may further illustrate steps of another connector assembly process, such as one or more blocks of the method 300 described below with respect to FIG. 3. Turning to FIG. 8M, a perspective exploded view of the frame 801 is shown. The frame can include one or more detent holders 818, one or more recesses 819, one or more caps 814A and 814B. The detent holder 818 can be an opening in the frame 801. An adhesive can be applied to the recess 819 in the frame 801. The recess 819 can engage with the cap 814A that covers the detent holder 818 of the frame 801. Attaching the cap 814A to the frame 801 can cause the detent holder 818 to form a pocket, which can engage with a detent of a male connector. Turning to FIG. 8N, the one or more caps 814A and 814B can be connected to the frame.

Figure 8P:
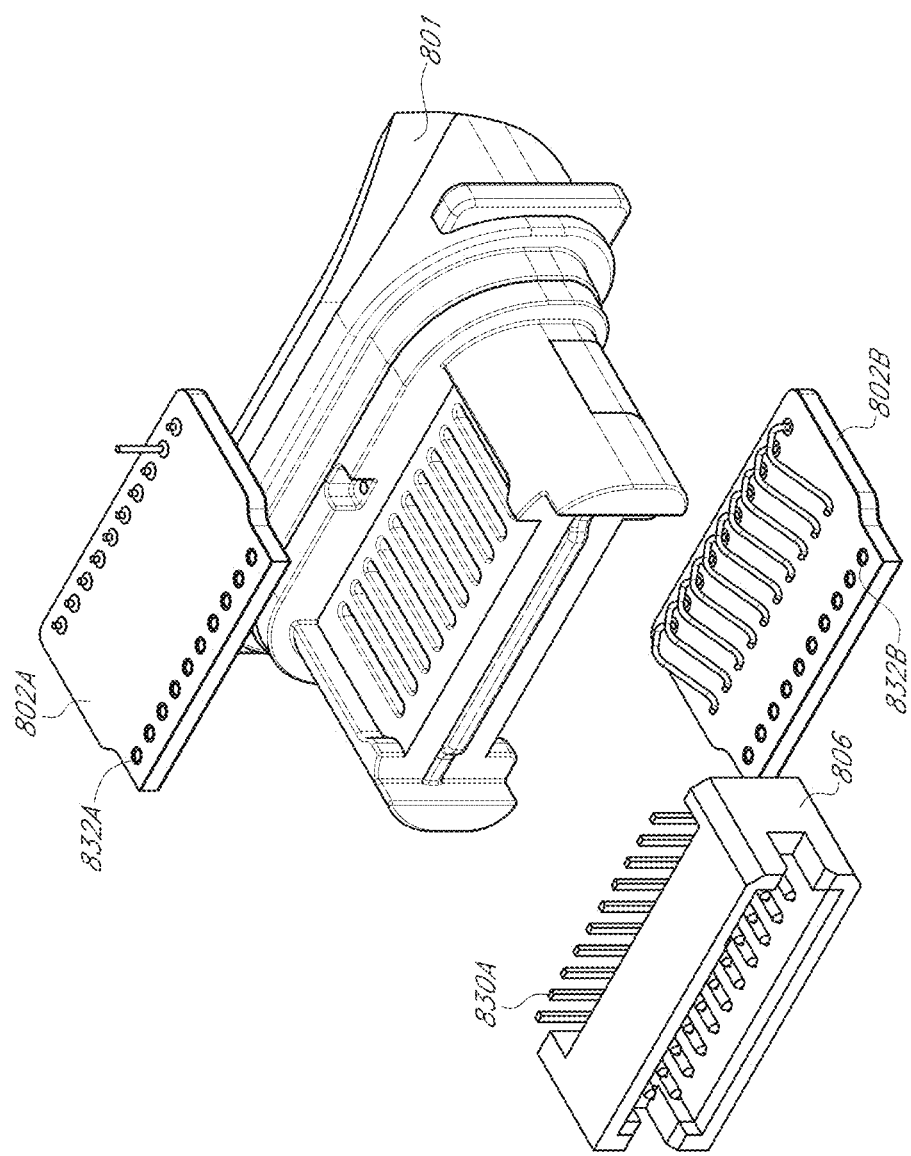

Turning to FIG. 8O, a perspective exploded view of the frame 801 and other components are shown. The frame 801 can include one or more openings 816A that can fit the one or more contacts 804A. The one or more contacts 804A and 804B can be attached to one or more boards 804A and 804B, respectively. Turning to FIG. 8P, a perspective, exploded, and back view of the frame 801 and other components are shown. In FIGS. 8O and 8P, the one or more boards 802A and 802B can be attached to a connector header 806 with one or more pins 830A and 830B. The one or more pins 830A and 830B of the connector header 806 may fit within the one or more openings 832A and 832B in the one or more boards 802A and 802B, respectively.

Figure 8Q:
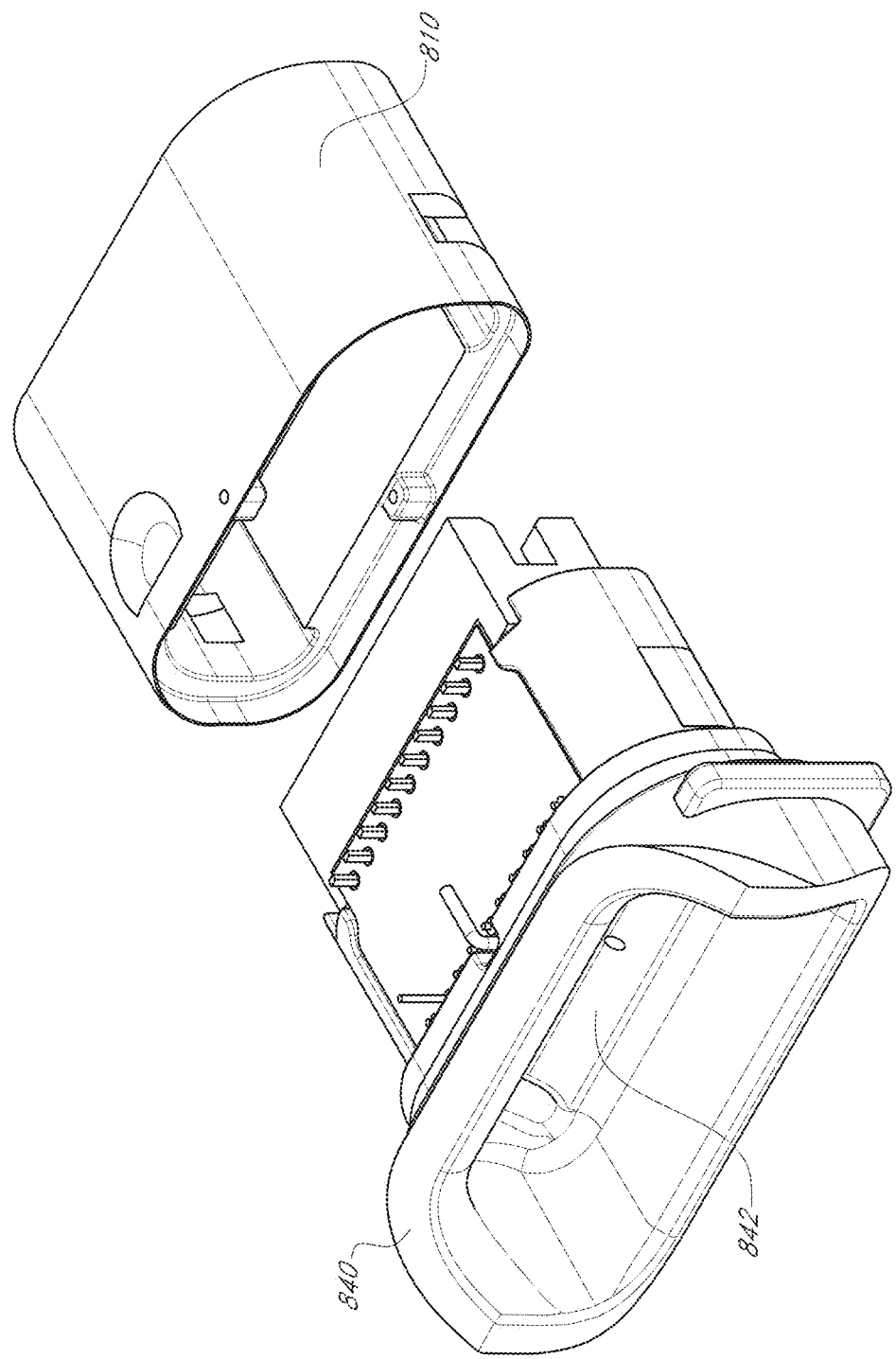

Turning to FIG. 8Q, a partially exploded perspective view of a connector assembly is shown. A mold 810 can be applied to the connector assembly 840. Example applications of the mold 810 to the connector assembly 840 include injection molding techniques. The mold 810 can include and/or can be made of a thermoplastic polymer, such as polypropylene. The mold material, such as a thermoplastic polymer, can have a low viscosity during application and can flow in and fill in spaces well, which may advantageously improve sealing and/or water resistance in a cost effective manner. Accordingly, the connector assembly 840 with the mold 810 and/or the pockets with the contacts (not shown) can create a water resistant barrier. If water were to get into the opening 842 with the contacts, the mold 810 and/or the pockets can prevent water from entering the device with the connector and the opening may behave like a cup. Thus, even if water gets into the opening 842, the water resistant features of the connector assembly 840 may enable a clinician to shake and/or blow inside the connector assembly 840 to remove water and water may not enter the device. Thus, the clinician can then insert a male connector into the connector assembly 840 without a short circuit occurring.

Figure 8R:
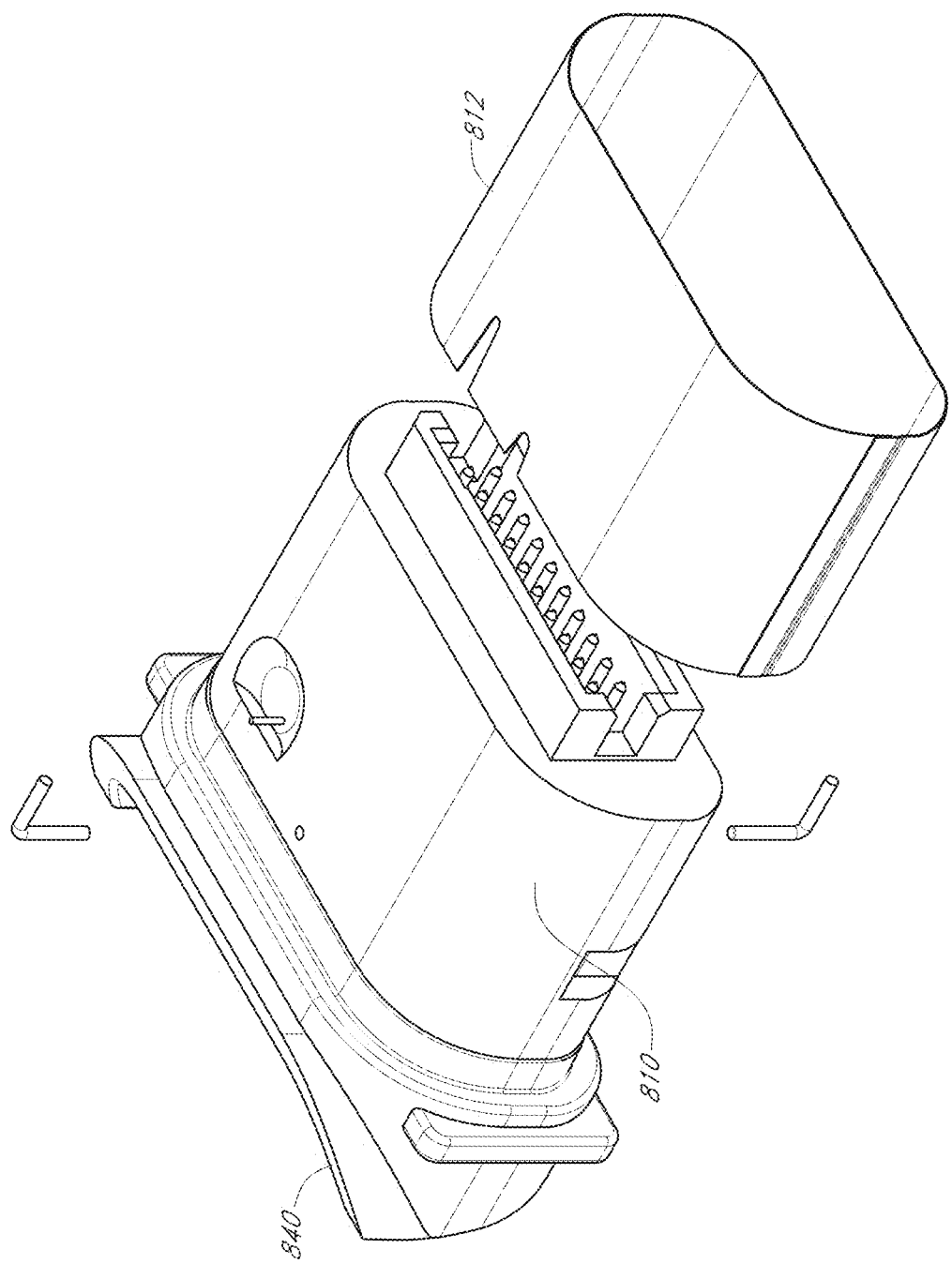

Turning to FIGS. 8R and 8S, additional views of a connector assembly are shown. In FIG. 8R, shield 812 can be attached to the connector assembly 840. The shield 812 can include and/or can be made of copper. In FIG. 8S, the ground pin 805 can be located within a slit in the shield 812. The one or more electrostatic discharge pins 808A can be folded to contact the shield 812. The one or more electrostatic discharge pins 808A and 808B and/or the ground pin 805 can include and/or can be made of brass. The one or more pins 808A, 808B, and 805, such as the one or more electrostatic discharge pins and/or the ground pin, can be soldered to the shield 812.

In some embodiments, the female connector can receive physiological signals from a physiological sensor. The female connector 820 of FIGS. 8H-8L can further couple the physiological sensor with a patient monitor, which is described above and/or below with respect to FIGS. 1 and/or 13. The female connector 820 can include a frame. An example frame is the frame 801 of FIGS. 8A-8E and/or 8M-8P, which may be rigid. The frame 801 can include a set of openings and/or pockets 816A and 816B as shown and described above with respect to FIGS. 8C and 8D. A circuit may be disposed within the frame. An example circuit is the circuit board 802A of FIGS. 8A, 8B, 8F, 8G, 8I, 8O, and/or 8P. The circuit board 802A can transmit the physiological signals to a hardware processor of a patient monitor. A set of contacts can be disposed on the circuit board. Example contacts are the electrical contacts 804A of FIGS. 8F and/or 8G. Each of the electrical contacts 804A can be disposed in a respective pocket 816A of the frame 801 as shown and described above with respect to FIG. 8O. The electrical contacts 804A can contact second electrical contacts in a corresponding male connector when the male connector is inserted into the female connector, where the male connector can be coupled to a physiological sensor. As shown in FIG. 8I, the electrical contacts 804A can be partially exposed to air when the male connector is not inserted into the female connector 820. As shown and described above with respect to FIGS. 8Q and/or 8R, a mold 810 can circumferentially surround the electrical contacts and/or the circuit. The mold 810 can be rigid. Thus, according to some embodiments, the mold 810 may advantageously create a water-resistant seal around the electrical contacts and/or may prevent water from entering the device where the female connector resides, such as a patient monitor.

Figure 9A:
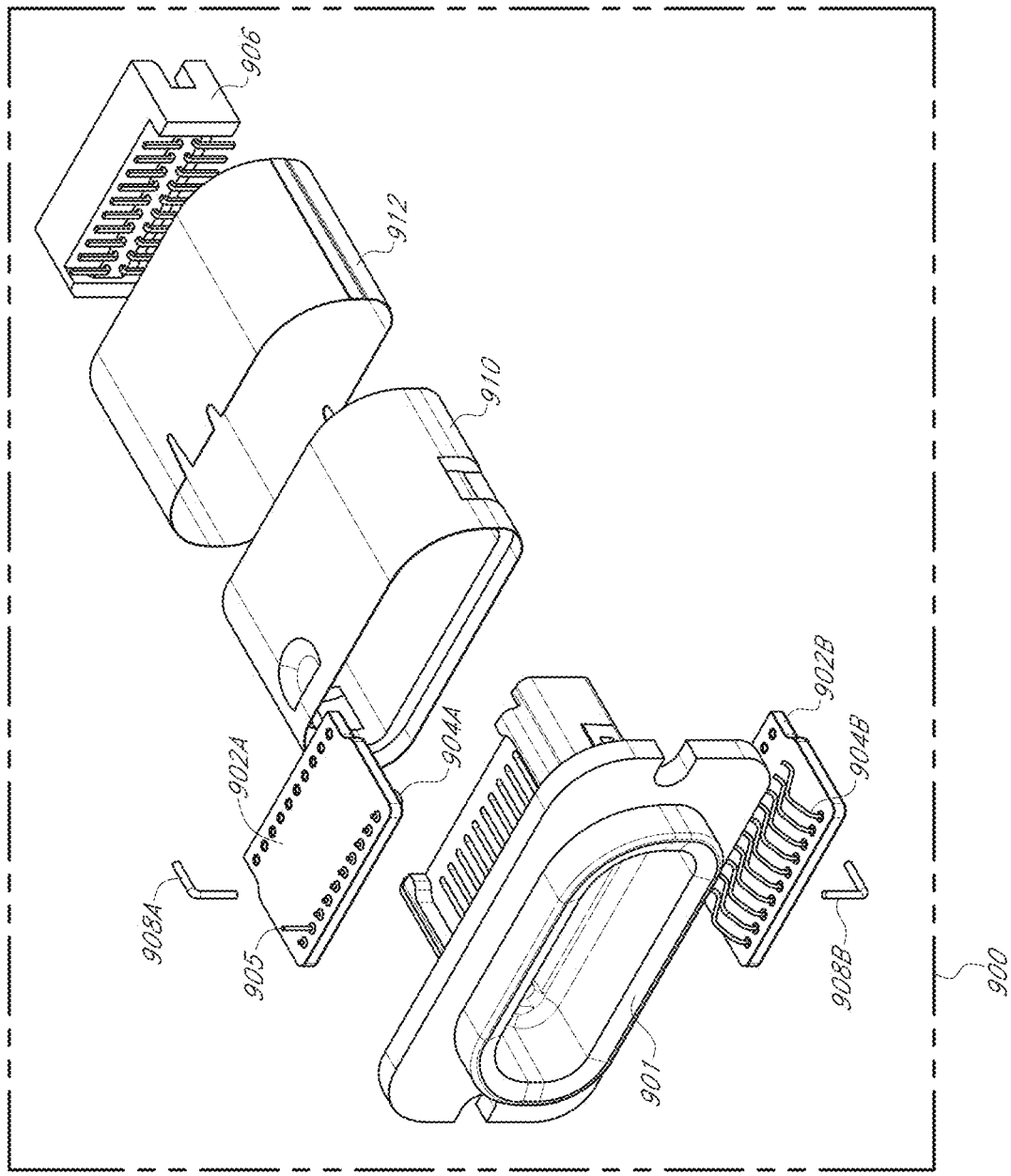
FIGS. 9A-9F are perspective exploded, front, top, side, back, and cross-section views of additional female connector components and another female connector, according to some embodiments of the present disclosure.

FIGS. 9A-9F illustrate another connector assembly and/or connector. The connector assembly 900 and/or connector 920 of FIGS. 9A-9F may be similar to the connector assembly 800 and/or the connector 820 of FIGS. 8A-8S. Referring to FIG. 9A, the connector assembly 900 can include a frame 901, one or more boards 902A and 902B, a connector header 906, one or more electrostatic discharge pins 908A and 908B, a mold 910, and a shield 912. The boards 902A and 902B can include one or more contacts 904A and 904B, respectively. The board 802A can include a ground pin 905.

Figure 9B:
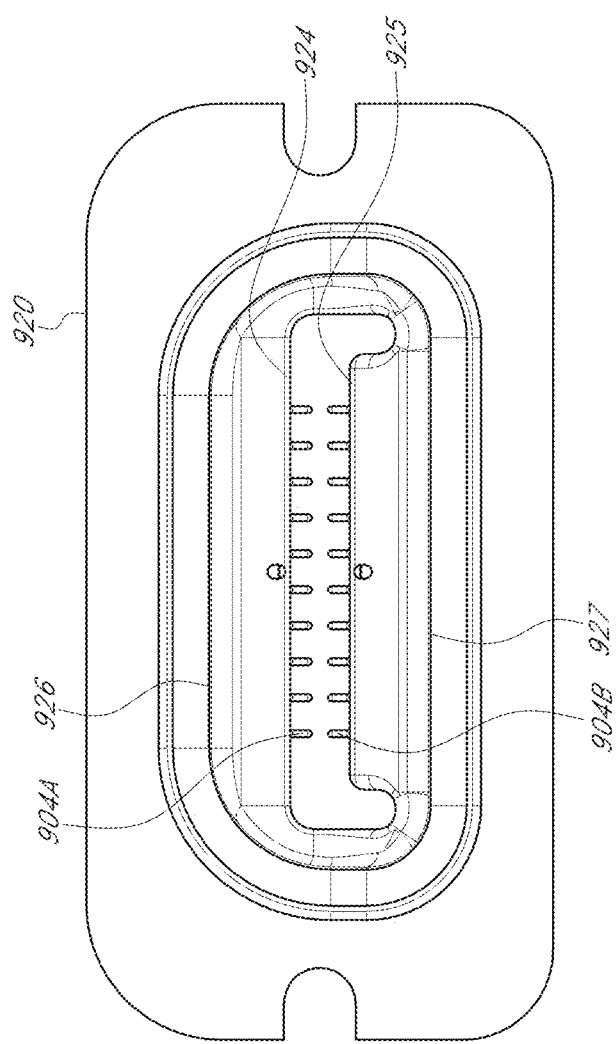
Figure 9C:
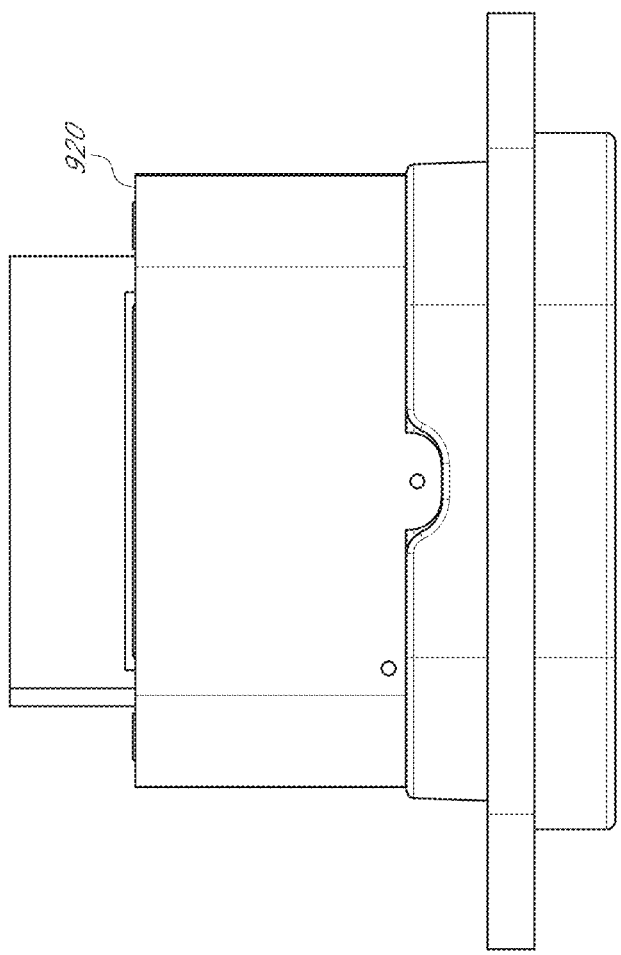
Figure 9D:
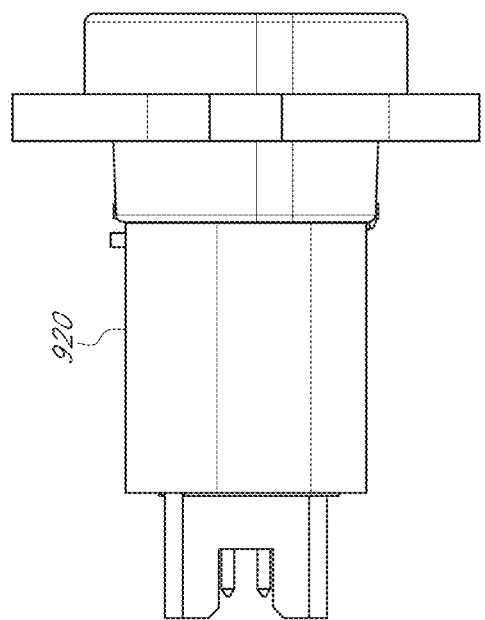
Figure 9E:
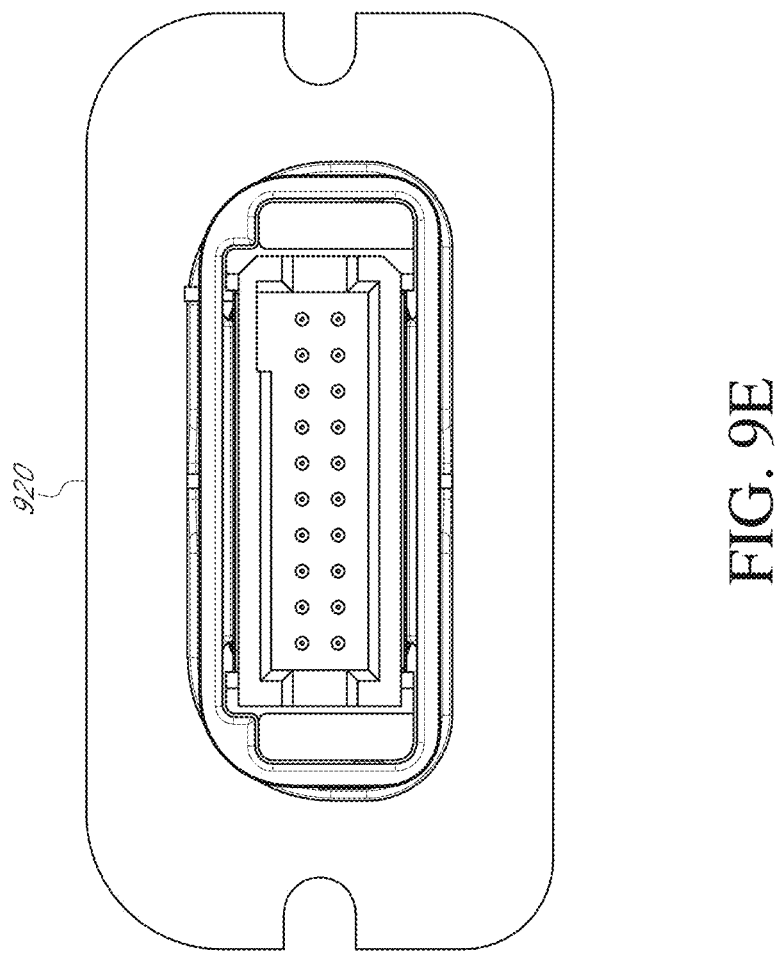

In FIGS. 9B-9F, another connector 920 is shown. The connector 920 is an example of the female connector 120 described above with respect to FIG. 1. Turning to FIG. 9B, a front view of the connector 920 is shown. The connector 920 can include the top and bottom points 926 and 927 of a distal opening and other top and bottom points 924 and 925 of a proximal opening. The distal opening and the proximal opening can receive a male connector. In some embodiments, the height of the distal opening at the top and bottom points 926 and 927 can be between approximately 0.80 centimeters (0.315 inches) and approximately 0.81 centimeters (0.32 inches), and/or the height of the proximal opening at the other top and bottom points 924 and 925 can be between approximately 0.16 centimeters (0.063 inches) and approximately 0.18 centimeters (0.07 inches). In other embodiments, the height of the first distal opening at the top and bottom points 926 and 927 can be between approximately 0.74 centimeters (0.29 inches) and approximately 0.81 centimeters (0.32 inches), and/or the height of the proximal opening at the other top and bottom points 924 and 925 can be between approximately 0.15 centimeters (0.06 inches) and approximately 0.18 centimeters (0.07 inches). The height of the proximal opening at the other top and bottom points 924 and 925 can be between approximately 0.15 centimeters (0.06 inches) and approximately 0.19 centimeters (0.075 inches). In yet further embodiments, the height of the first distal opening at the top and bottom points 926 and 927 can be between approximately 0.74 centimeters (0.29 inches) and approximately 0.84 centimeters (0.33 inches), and/or the height of the proximal opening at the other top and bottom points 924 and 925 can be between approximately 0.15 centimeters (0.06 inches) and approximately 0.20 centimeters (0.08 inches). The proximal opening at the other top and bottom points 924 and 925 can include the contacts 904A and 904B. In some embodiments, the dimensions of the distal opening at the top and bottom points 926 and 927 and/or the dimensions of the proximal opening at the other top and bottom points 924 and 925 may advantageously prevent inadvertent touching, such as touching by a finger, of the contacts 904A and 904B. In FIG. 9C, a top view of the connector 920 is shown. In FIG. 9D, a side view of the connector 920 is shown. In FIG. 9E, a back view of the connector 920 is shown.

Figure 9F:
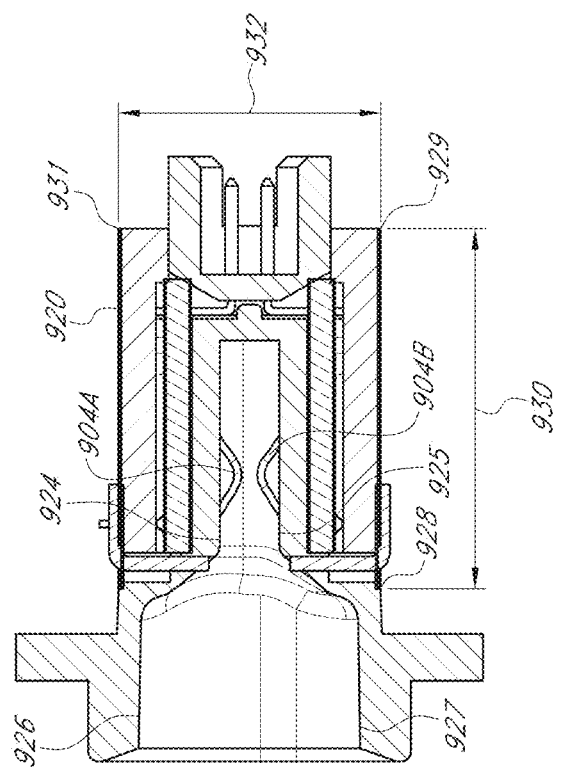

Turning to FIG. 9F, a cross-section view of the connector 920 is shown. The components and/or dimensions of the connector 920 shown and described above with respect to FIG. 9B may be similar to the components and/or dimensions of the connector 920 in FIG. 9F. The connector 920 can include the top and bottom points 926 and 927 at a distal opening and other top and bottom points 924 and 925 at a proximal opening. The proximal opening at the other top and bottom points 924 and 925 can include the contacts 904A and 904B. In some embodiments, the portion of the connector 920 at the edge points 928 and 929 is the length measurement 930, which can be approximately 1.27 centimeters (0.5 inches). The length measurement 930 can be between approximately 1.27 centimeters (0.5 inches) and approximately 1.40 centimeters (0.55 inches). In other embodiments, the length measurement 930 can be between approximately 1.27 centimeters (0.5 inches) and approximately 1.52 centimeters (0.6 inches). The portion of the connector 920 at the other edge points 929 and 931 is the height measurement 932, which can be approximately 0.91 centimeters (0.36 inches). The height measurement 932 can be between approximately 0.91 centimeters (0.36 inches) and approximately 0.94 centimeters (0.37 inches). In other embodiments, the height measurement 932 can be between approximately 0.91 centimeters (0.36 inches) and approximately 0.97 centimeters (0.38 inches). In some embodiments, the cross-section of the connector 920 is similar to a cross-section of the connector 820 of FIG. 8L.

V. Connector Assembly Processes

Figure 2:
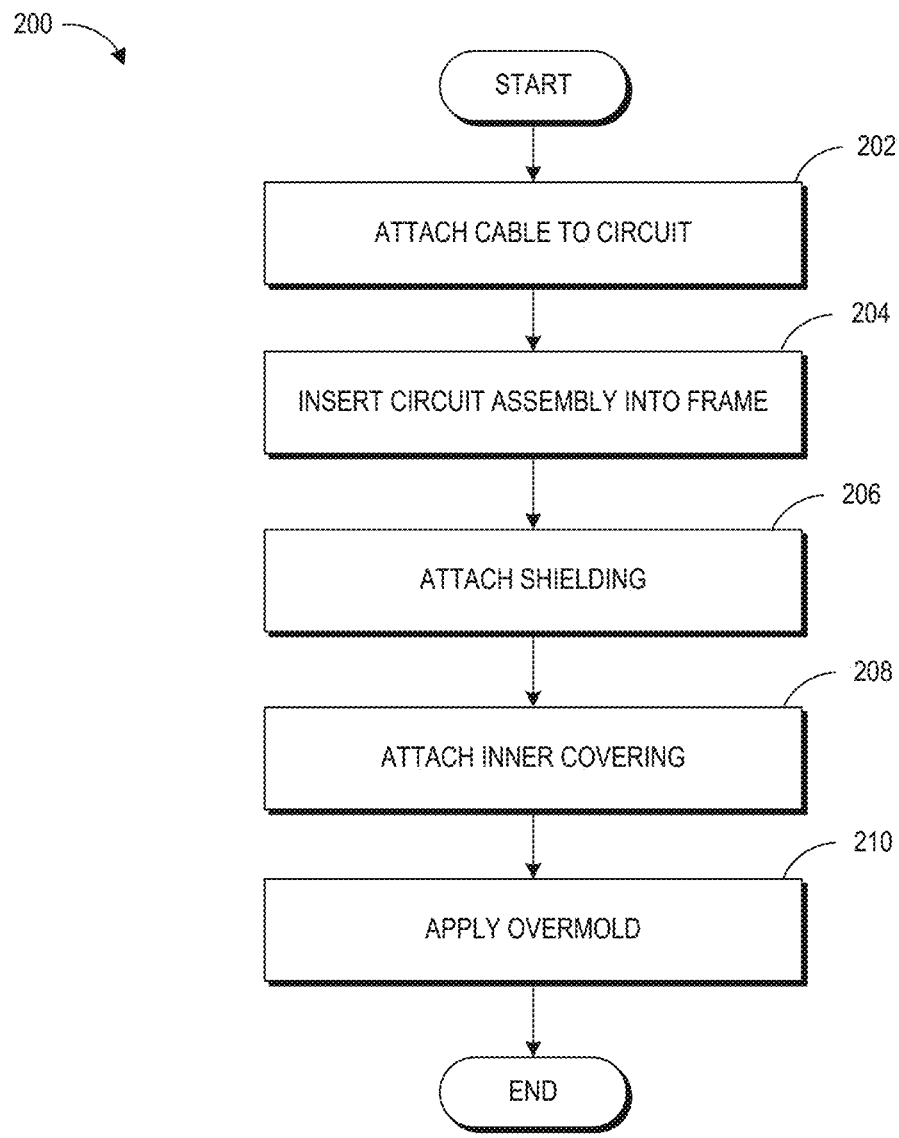
FIG. 2 is a flowchart of a method of assembling a connector, according to some embodiments of the present disclosure.

Turning to FIG. 2, a connector assembly process 200 is shown. The process 200 provides example approaches to assemble a connector. Depending on the embodiment, the method 200 may include fewer or additional blocks and/or the blocks may be performed in order different than is illustrated.

At block 202, a cable is attached to a circuit. A cable can include conductor strands. The circuit can include an opening in the distal portion of the circuit. The cable can be looped through the opening in the circuit. In some embodiments, the cable can include a fiber material, such as a synthetic fiber and/or a para-aramid synthetic fiber, which can be looped through the opening in the circuit. The loop can be pulled snug to the circuit and knotted. An adhesive, such as a cyanoacrylate adhesive, can be applied to the connection between the cable and the circuit, such as where the fiber material is connected to the circuit. An example amount of adhesive is a drop. Additional details regarding attaching a cable to a circuit are described above with respect to FIG. 5A.

At block 204, the circuit assembly can be inserted into a frame. The frame can include and/or can be made of plastic, such as polycarbonate and/or a polycarbonate blend. An adhesive, such as a cyanoacrylate adhesive, can be applied to connect the circuit to the frame. Example amounts of adhesive are beads or drops. A bead of adhesive can be applied to a proximal portion of the frame that contacts the proximal end of the circuit. A drop of adhesive can be applied to the edges of the circuit and the frame, which can be applied after insertion of the circuit into the frame. Additional details regarding inserting a circuit assembly into a frame are described above with respect to FIGS. 5A and/or 5B.

At block 206, a shield can be attached to the frame assembly. The shield can include and/or can be made of copper. The shield may advantageously reduce electromagnetic interference. In some embodiments, the cable strands can be connected to the circuit and/or the shield. A first set of cable strands can be soldered to the circuit and a second set of cable strands can be soldered to the shield. Additional details regarding attaching a shield to a frame assembly are described above with respect to FIGS. 5B and/or 5C.

At block 208, an inner covering can be attached to the connector assembly. An example inner covering is an inner mold that can include and/or can be made of a thermoplastic polymer, such as polypropylene. In some embodiments, the inner mold can have a low viscosity during application and can flow in and fill in spaces well, which may advantageously improve sealing and/or water resistance. The inner mold, which can include a thermoplastic polymer or other material, may also advantageously be a cost-effective means of providing sealing. The inner molding process may advantageously be a consistent manufacturing process for producing water resistant cable assemblies. An injection molding technique may be applied to create the inner mold, which can include and/or can be made of a thermoplastic polymer, such as polypropylene. Additional details regarding attaching an inner covering are described above with respect to FIGS. 5D and/or 5E.

At block 210, an overmold can be applied to the connector assembly. An example overmold material is a thermoplastic elastomer. The overmold can advantageously provide water resistance. An injection molding technique may be applied to create the overmold, which can include or can be made of a thermoplastic elastomer. The overmold may also advantageously be a cost-effective means of providing sealing. The overmold process may advantageously be a consistent manufacturing process for producing water resistant cable assemblies. The overmold can include a rib. The manufacturing process of the rib may advantageously tolerate variances in the height of the rib. Since the rib can include or can be made of the thermoplastic elastomer, a slightly higher rib created during the manufacturing process may require a slightly higher insertion force; however, the higher rib may still be insertable into the receiving socket to create a water resistant seal. The overmold can be created with a draft angle that improves positive interference and/or the forming of a water resistant seal when the connector is inserted into another connector. In some embodiments, the overmold can include both a rib and a draft angle. In other embodiments, an overmold can include one of a rib or a draft angle. Additional details regarding an example overmold are described above with respect to FIGS. 4A-4F.

Figure 3:
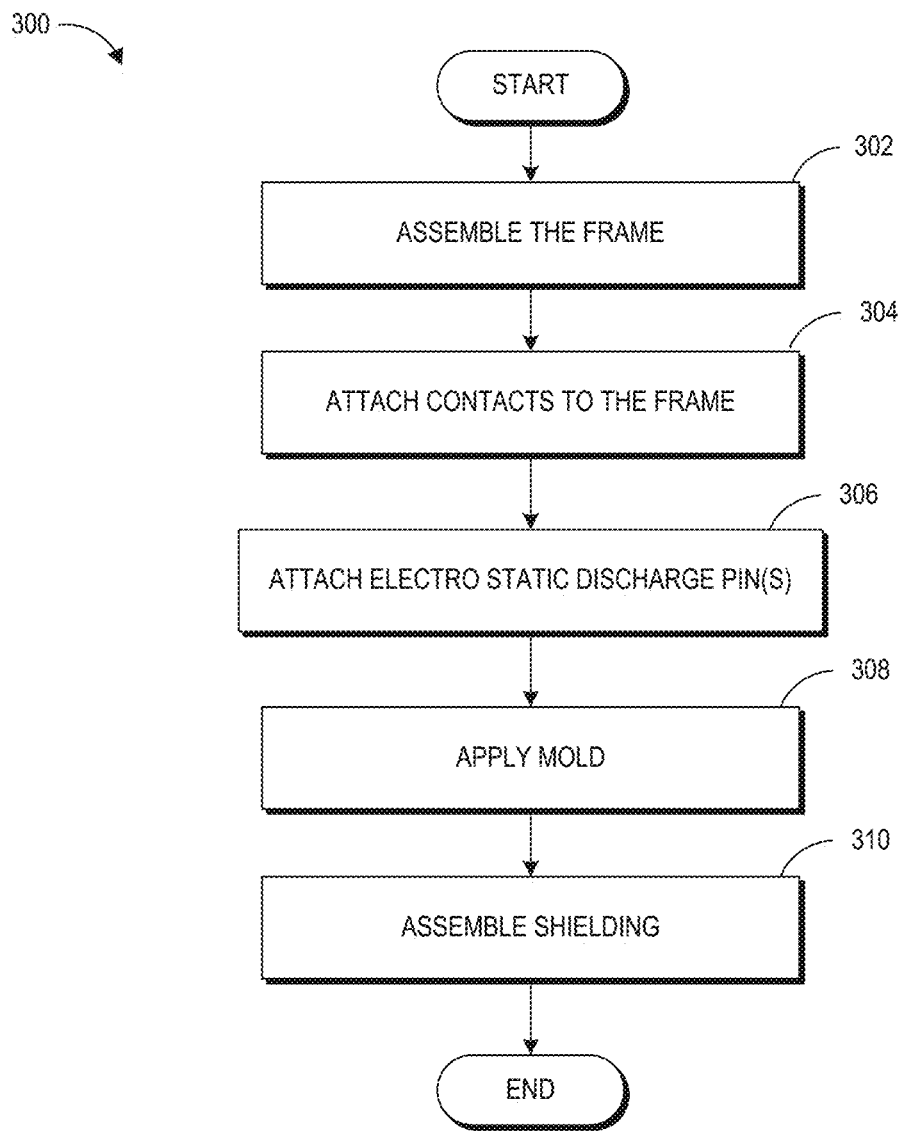
FIG. 3 is a flowchart of another method of assembling a connector, according to some embodiments of the present disclosure.

Turning to FIG. 3, another connector assembly process 300 is shown. The process 300 provides additional example approaches by which a connector can be assembled. Depending on the embodiment, the method 300 may include fewer or additional blocks and/or the blocks may be performed in order different than is illustrated. One or more blocks of the method 300 may be similar to one or more blocks of the method 200 of FIG. 2.

At block 302, the frame can be assembled. The frame can include and/or can be made of plastic, such as polycarbonate and/or a polycarbonate blend. The frame can include one or more detent holders and one or more caps. A detent holder can be an opening in the frame, which also can be a pocket when combined with a cap. A detent of a first connector may engage with a detent holder of a second connector that prevents motion until released. The detent system may advantageously provide positive feedback to a user when inserting and/or removing a first connector from a second connector. The one or more caps can be connected to the frame. An adhesive, such as a cyanoacrylate adhesive, can be applied to a recess in the frame where the recess can engage with the cap that covers the detent holder of the frame. In some embodiments, designing the frame with one or more detent holders that are covered with one or more caps is an efficient method for creating a frame with a detent holder. In other embodiments, a frame is created without caps and with cutouts on the inside of the frame that are the detent holders. Additional details regarding assembling a frame are described above respect to FIGS. 8M and/or 8N.

At block 304, one or more contacts can be attached to the frame assembly. The frame can include one or more openings that can fit one or more contacts. The one or more openings may advantageously improve the water resistance of the connector. The one or more contacts can be attached to one or more boards. The one or more boards can be attached to a connector header with one or more pins. The one or more pins of the connector header can fit within the one or more openings in the one or more boards. Additional details regarding attaching contacts to the frame assembly are described above respect to FIGS. 8O and/or 8P.

At block 306, one or more electrostatic discharge pins can be attached to the frame assembly. An electrostatic discharge pin can be inserted into an opening in the frame. In some embodiments, the one or more electrostatic discharge pens can be trimmed after being placed into the frame.

At block 308, a mold can be applied to the connector assembly. An example mold material a thermoplastic polymer, such as polypropylene. The mold material, such as a thermoplastic polymer, can have a low viscosity during application and can flow in and fill in spaces well, which may advantageously improve sealing and/or water resistance in a cost effective manner. An injection molding technique may be applied to create the mold, which can include and/or can be made of a thermoplastic polymer, such as polypropylene. Accordingly, the connector assembly with the mold and/or the pockets with the contacts can create a water resistant barrier. If water were to get into the opening with the contacts, the mold and/or the pockets prevent water from entering the device with the connector and the opening behaves like a cup. Thus, the mold and/or pockets can prevent and/or reduce electrical shorts. Additional details regarding applying a mold to a connector assembly are described above with respect to FIG. 8Q.

At block 310, a shield can be attached to the connector assembly. An example shield is a copper shield. The shield may advantageously reduce electromagnetic interference. In some embodiments, the ground pin can be located within a slit in the shield. The one or more electrostatic discharge pins can be folded to contact the shield. The one or more pins, such as the one or more electrostatic discharge pins and/or the ground pin, can be soldered to the shield. Additional details regarding attaching are described above with respect to FIGS. 8R and/or 8S.

VI. Connectors and Devices

Figure 10A:
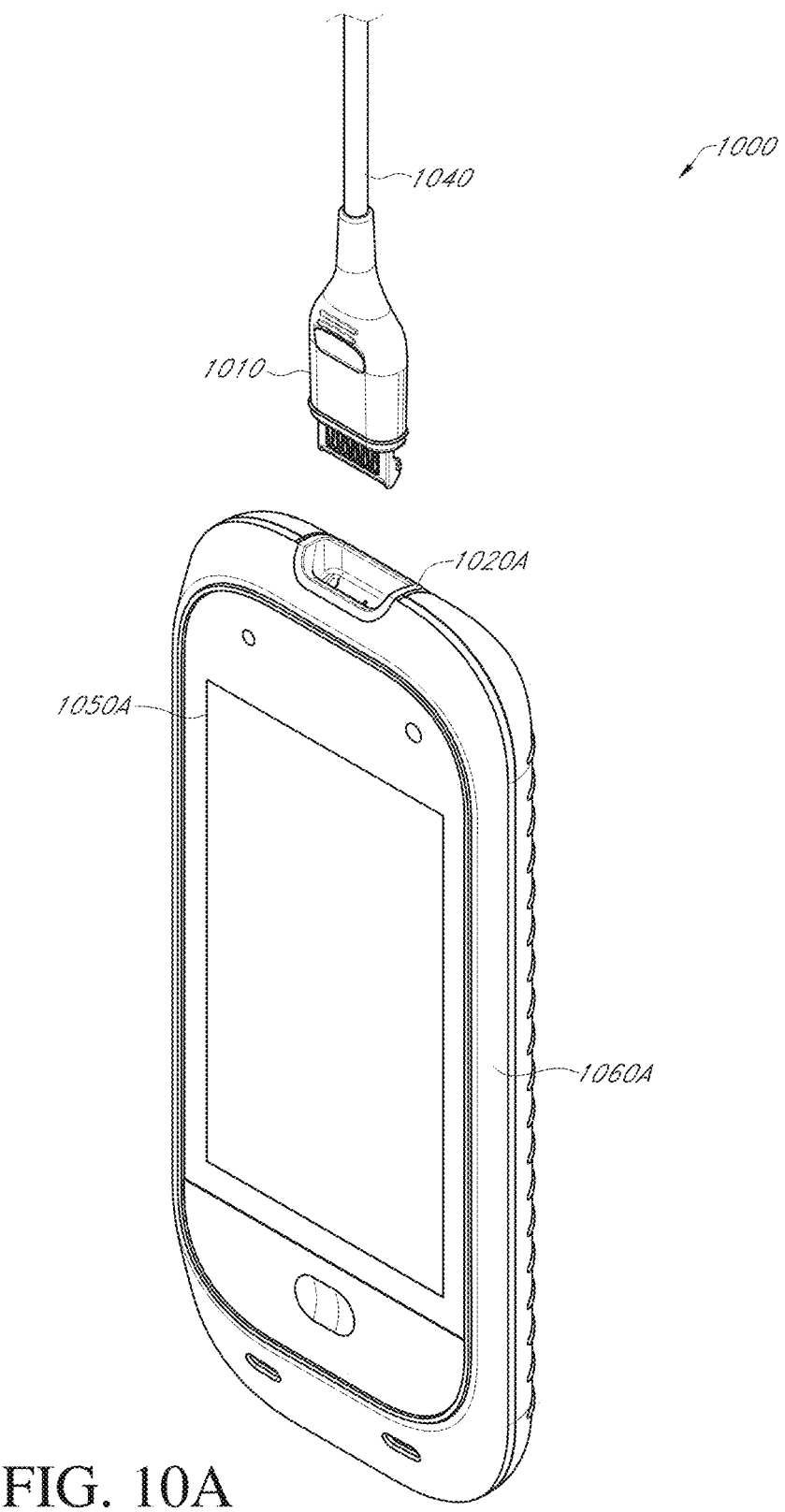
FIGS. 10A and 10B are top and perspective views of a male connector and female connectors in patient monitors, according to some embodiments of the present disclosure.
Figure 10B:
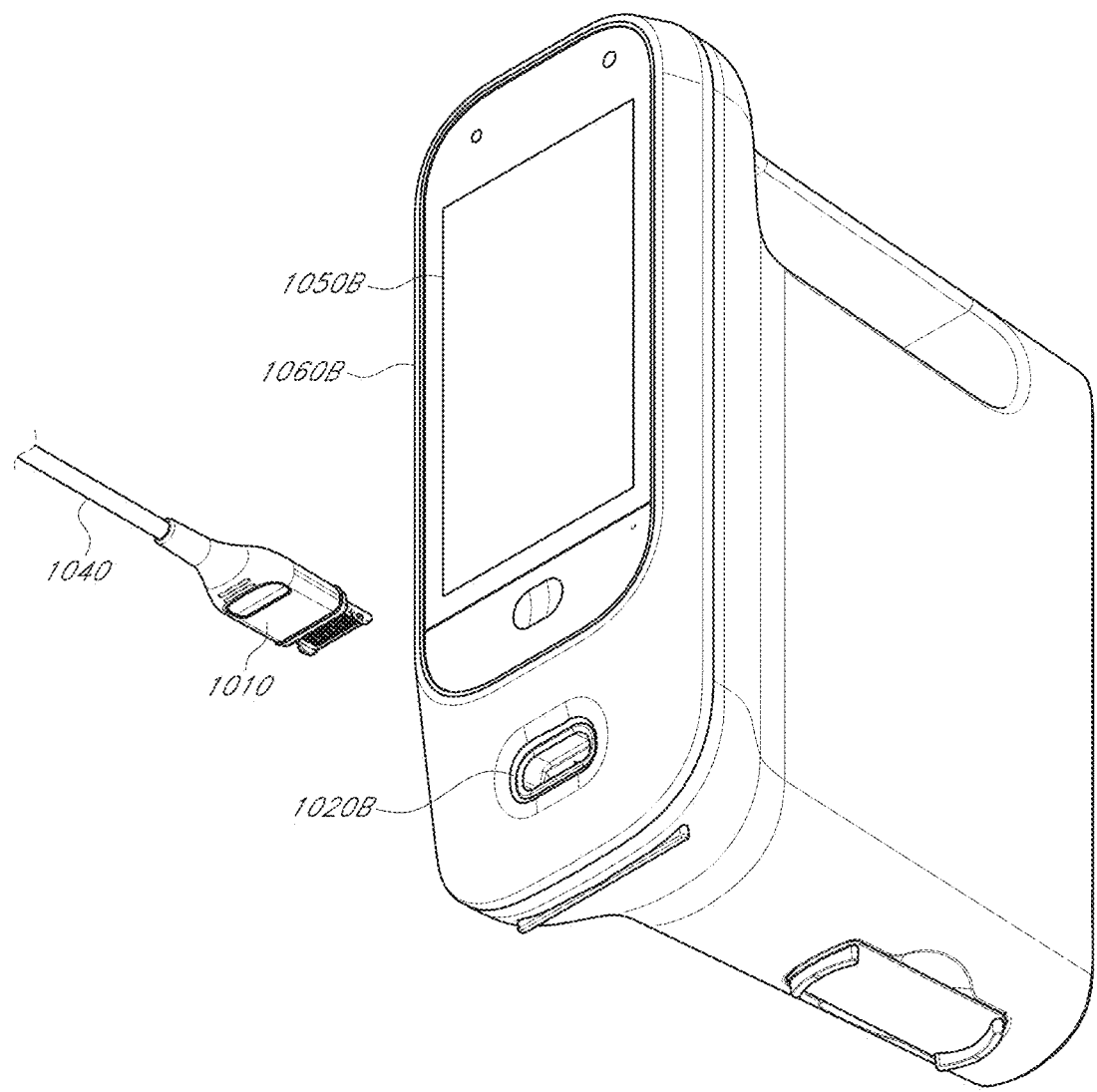

FIGS. 10A and 10B illustrate male and female connectors, and patient monitors. Turning to FIG. 10A, the connector environment 1000 can include a first cable assembly and a patient monitor 1060A. The first cable assembly can include a cable 1040 and a male connector 1010. The male connector 1010 may be similar to the connector 400 described above with respect to FIGS. 4A-4F. The patient monitor 1060A can include a female connector 1020A and a display 1050A. The female connector 1020A may be similar to the connector 820 described above with respect to FIGS. 8H-8K. The male connector 1010 can be inserted into the female connector 1020A. Turning to FIG. 10B, a connector environment 1080 is shown, which may be similar to the connector environment 1000 of FIG. 10A. However, the patient monitor 1060B may be different than the patient monitor 1060B of FIG. 10A. The patient monitor 1060B can include another female connector 1020B. The female connector 1020B may be similar to the connector 920 described above with respect to FIGS. 9B-9F.

In some embodiments, the cable assemblies of FIGS. 10A and 10B can interface one or more noninvasive physiological sensors with the patient monitors 1060A and 1060B. The male connector 1010 can be attached to the cable 1040 and can couple the cable 1040 with the patient monitor 1060A and/or 1060B so as to convey the physiological signals from the physiological sensor to the patient monitor 1060A and/or 1060B. The patient monitor 1060A and/or 1060B can process the physiological signals to obtain one or more measurements. The displays 1050A and 1050B of the patient monitors 1060A and 1060B, respectively, can present at least some of the measurements.

Figure 11A:
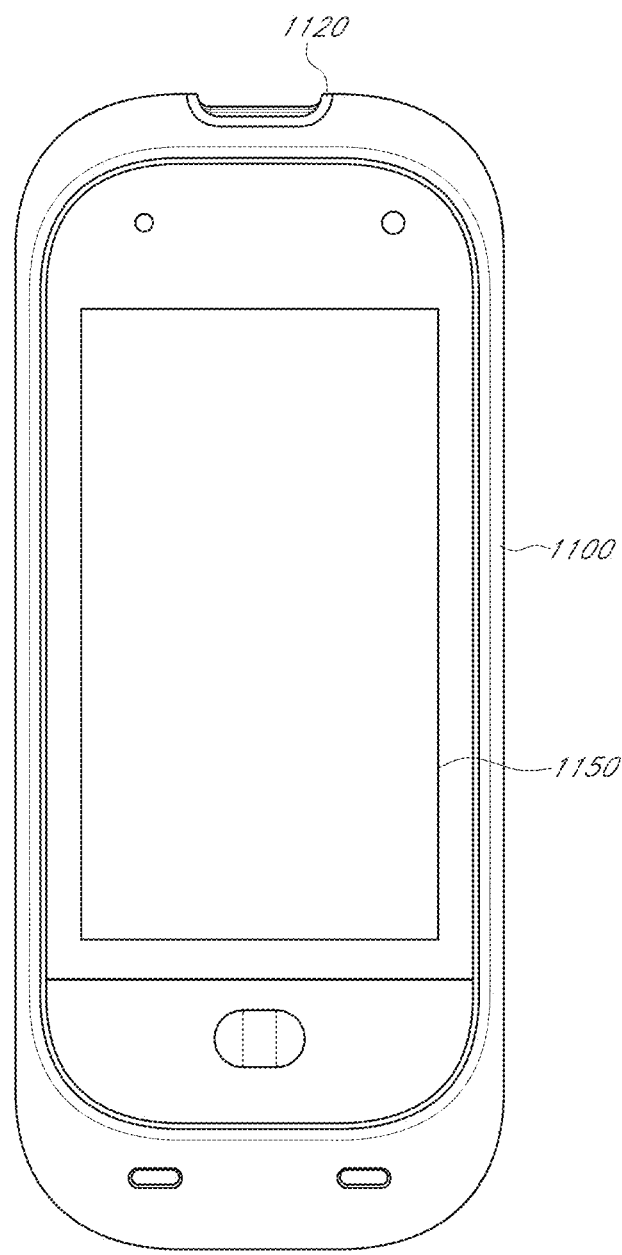
FIGS. 11A-11D are top, perspective, and front views of another female connector in a patient monitor, according to some embodiments of the present disclosure.
Figure 11B:
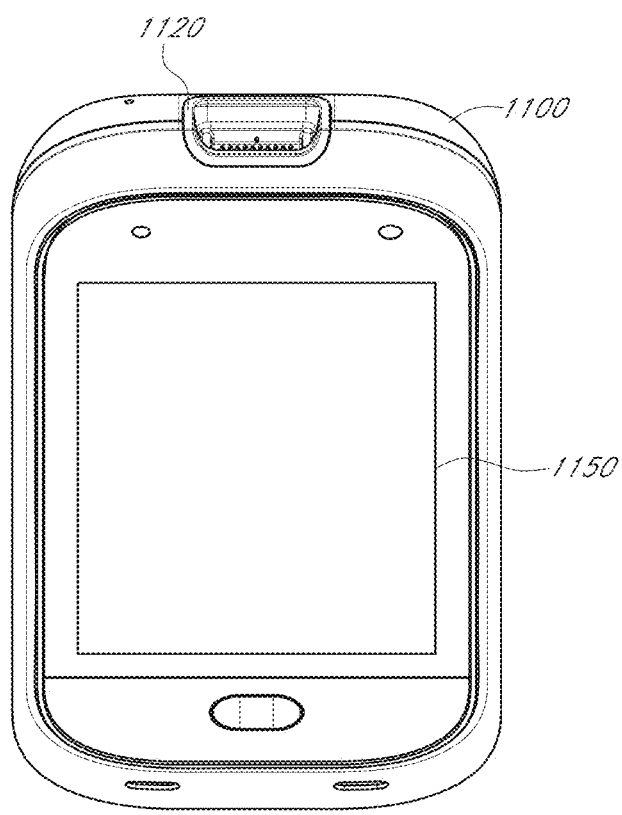
Figure 11C:
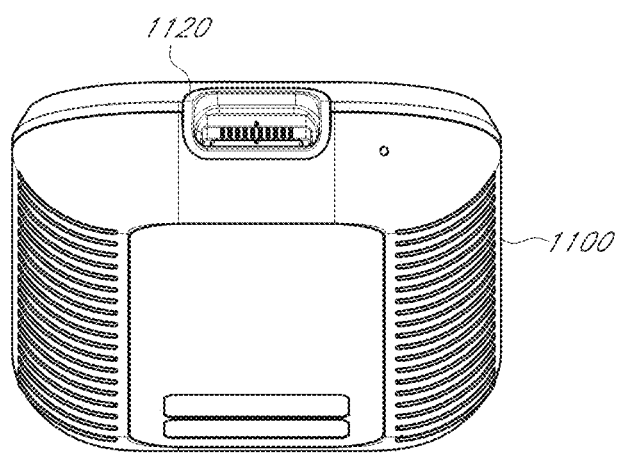
Figure 11D:
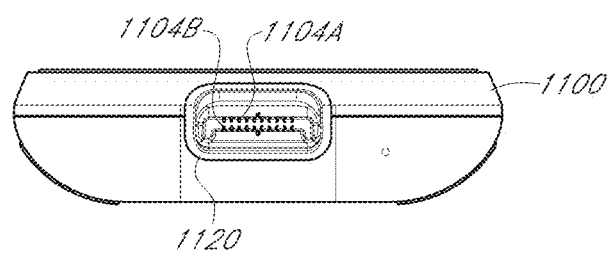

FIGS. 11A-11D illustrate views of a female connector and a patient monitor. In FIG. 11A a top view of the patient monitor 1100 is shown. The patient monitor 1100 may be similar to the patient monitor 1060A of FIG. 10A. The patient monitor 1100 can include a female connector 1120 and a display 1150. The female connector 1120 may be similar to the connector 820 described above with respect to FIGS. 8H-8K. Turning to FIG. 11B, a top perspective view of the patient monitor 1100 is shown. Turning to FIG. 11C, a bottom perspective view of the patient monitor 1100 is shown. Turning to FIG. 11D, a front view of the patient monitor 1100 is shown. As illustrated, the patient monitor 1100 can include the female connector 1120. The female connector 1120 can include one or more contacts 1104A and 1104B.

Figure 12A:
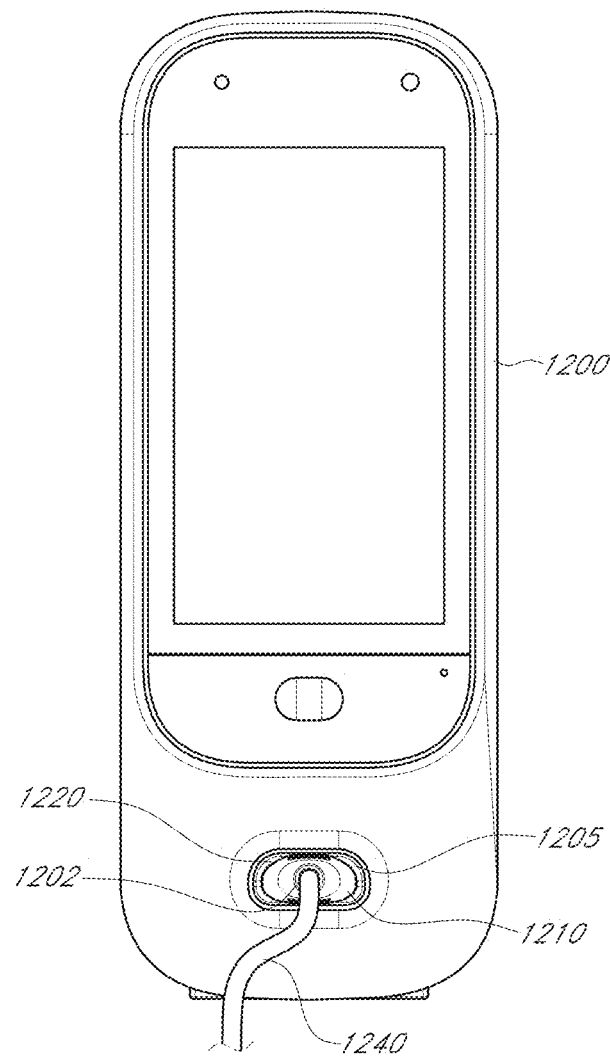
FIGS. 12A and 12B are front and perspective views of a male connector connected to a female connector in another patient monitor, according to some embodiments of the present disclosure.
Figure 12B:
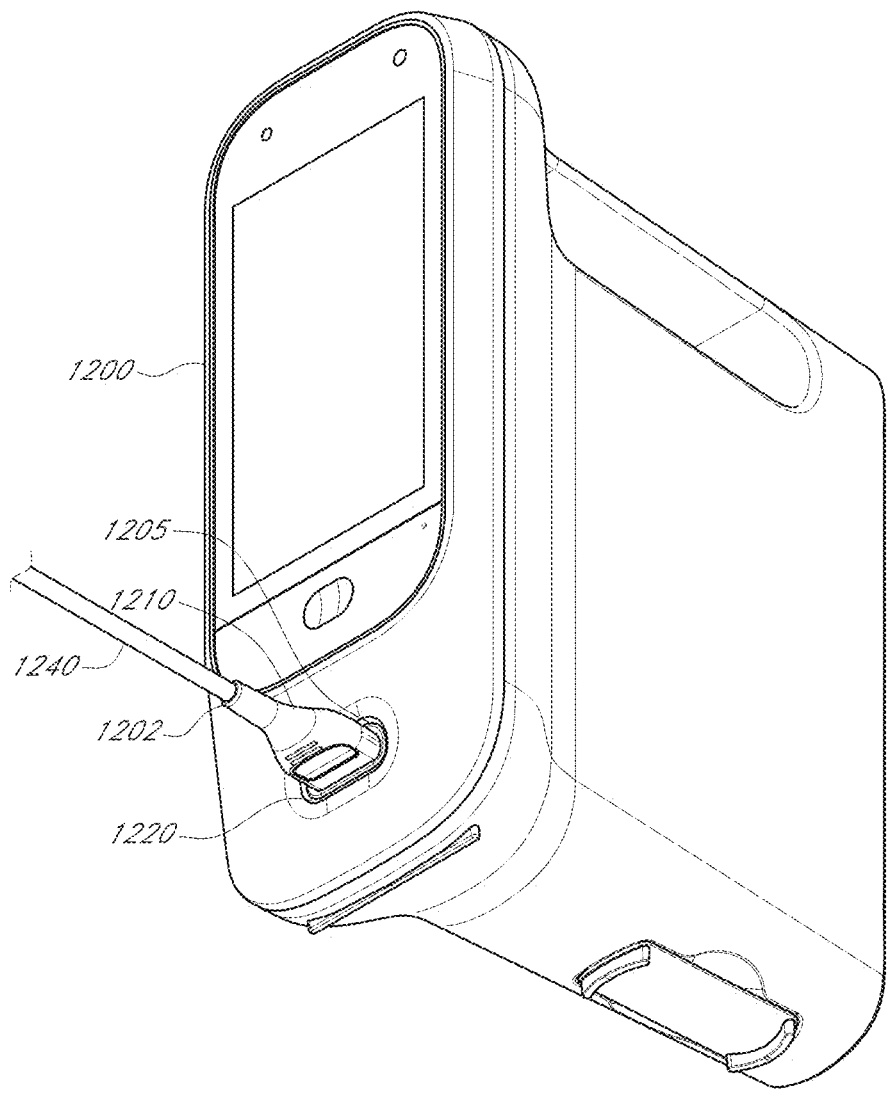

FIGS. 12A-12B illustrate views of a male connector engaged with a female connector of a patient monitor. Turning to FIG. 12A, the male connector 1210 can be engaged with the female connector 1220. The male connector 1210 can be attached to the cable 1240. The male connector 1210 may be similar to the connector 400 described above with respect to FIGS. 4A-4F. The patient monitor 1200 can include a female connector 1220. The female connector 1220 may be similar to the connector 920 described above with respect to FIGS. 9B-9F. Turning to FIG. 12B, a perspective view of the male connector 1210 as engaged with the female connector 1220 of the patient monitor 1200 is shown.

In FIGS. 12A-12B, the male connector 1210 can be inserted into the female connector 1220. In some embodiments, the male connector 1210 can include an overmold from a distal point 1202 and up to and including a proximal point 1205. The overmold can be pliable and/or may be water-resistant. The male connector 1210 can include a rib (not shown) that can create a seal with the female connector 1220 when the male connector 1210 is inserted into the female connector 1220 as shown. The rib can circumferentially surround the overmold. As illustrated, when the male connector 1210 is inserted into the female connector 1220, the rib of the male connector 1210 can be inserted past an outer edge of the female connector 1220. When the male connector 1210 is inserted into the female connector 1220, the contacts (not shown) of the male connector 1210 may no longer exposed to air, such that a water-resistant seal can be created between the male connector 1210 and the female connector 1220.

In some embodiments, the water-resistant medical device cable assembly, including the male connector 1210 and the cable 1240, can interface one or more noninvasive physiological sensors with the patient monitor 1200. The cable 1240 can connect to a physiological sensor. The cable 1240, which can include one or more conductors, can obtain physiological signals from a patient. The male connector 1210 can be attached to the cable 1240 and can couple the cable 1240 with the patient monitor 1200 so as to convey one or more physiological signals from the physiological sensor to the patient monitor 1200.

Figure 13:
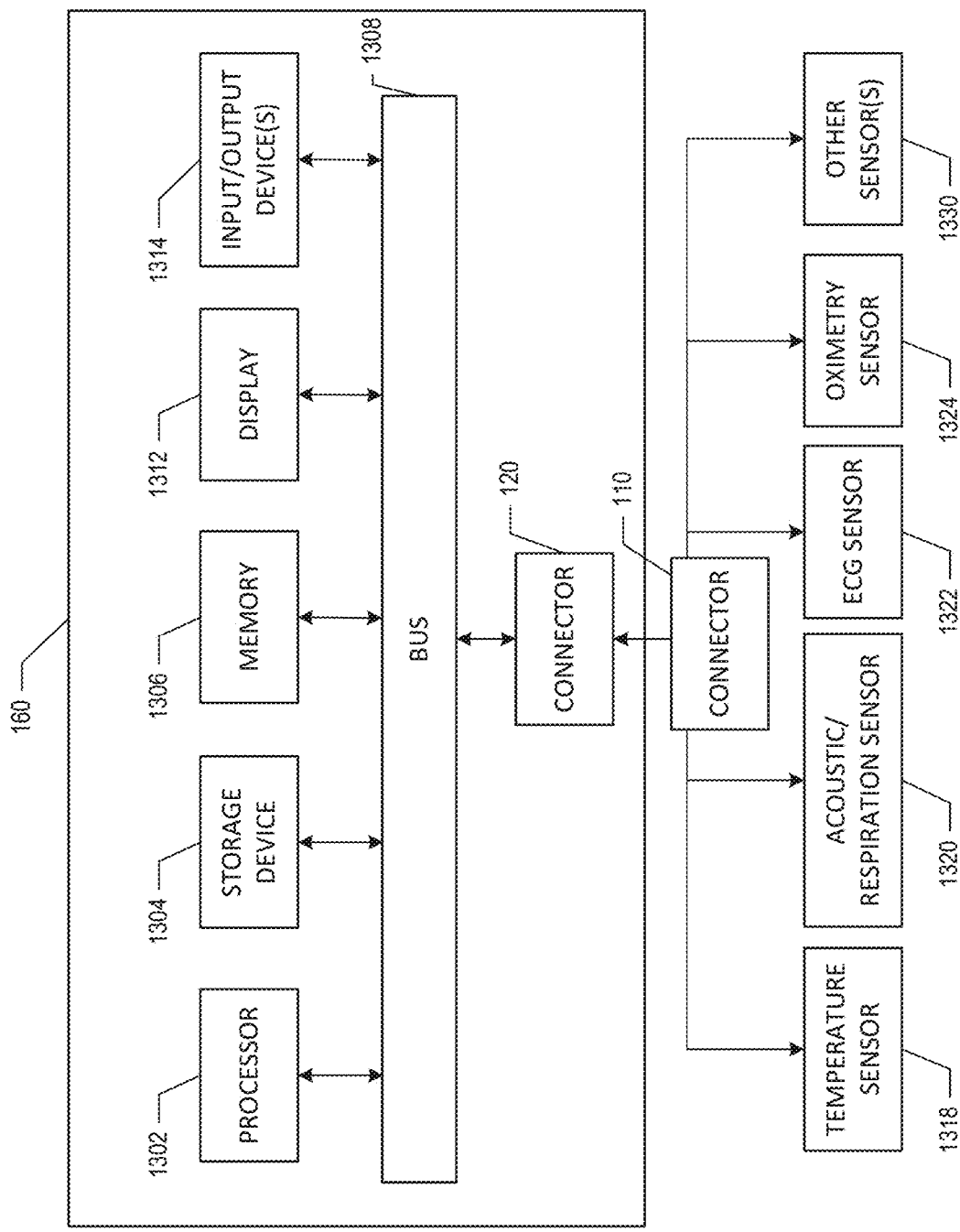
FIG. 13 is a block diagram illustrating an operating environment for a patient monitoring system including a patient monitor, connectors, and sensors.

FIG. 13 is a block diagram that illustrates example components of the patient monitor and/or computing device 160. The patient monitor 160 can include a hardware processor 1302, a data storage device 1304, a memory device 1306, a bus 1308, a display 1312, and one or more input/output devices 1314. A processor 1302 can also be implemented as a combination of computing devices, e.g., a combination of a digital signal processor and a microprocessor, a plurality of microprocessors, one or more microprocessors in conjunction with a digital signal processor, or any other such configuration. The processor 1302 can be configured, among other things, to process data, execute instructions to perform one or more functions, such as process one or more physiological signals to obtain one or measurements, as described herein. The data storage device 1304 can include a magnetic disk, optical disk, or flash drive, etc., and is provided and coupled to the bus 1308 for storing information and instructions. The memory 1306 can include one or more memory devices that store data, including without limitation, random access memory (RAM) and read-only memory (ROM). The patient monitor 160 may be coupled via the bus 1308 to a display 1312, such as a LCD display or touch screen, for displaying information to a user, such as a clinician. The patient monitor 160 may be coupled via the bus 1308 to one or more input/output devices 1314. The input device 1314 can include, but is not limited to, a keyboard, mouse, digital pen, microphone, touch screen, gesture recognition system, voice recognition system, imaging device (which may capture eye, hand, head, or body tracking data and/or placement), gamepad, accelerometer, or gyroscope.

In some embodiments, the hardware processor and/or digital signal processor 1302 can process physiological signals into representations of physiological parameters and/or measurements. The signals can be processed into multiple readings of each physiological parameter over a period of time such as, for example, 10 minutes, 30 minutes, or 1 hour. Additional details regarding processing of physiological signals to obtain measurements are described in at least U.S. patent application Ser. No. 11/366,208, filed Mar. 1, 2006, titled Noninvasive Multi-Parameter Patient Monitor, now issued as U.S. Pat. No. 8,130,105, and U.S. patent application Ser. No. 12/559,815, filed Sep. 15, 2009, titled Patient Monitor Including Multi-Parameter Graphical Display, now issued as U.S. Pat. No. 8,911,377, which is hereby incorporated by reference in its entirety.

In some embodiments, one or more cable assemblies can interface one or more sensors 1318, 1320, 1322, 1324, and/or 1330 with the patient monitor 160. The one or more sensors 1318, 1320, 1322, 1324, and/or 1330 can be connected via a cable to the male connector 110. When the male connector 110 is engaged with the female connector 120, one or more physiological signals can be obtained from the one or more sensors 1318, 1320, 1322, 1324, and/or 1330 and can be transmitted to the patient monitor 160.

A temperature sensor 1318 may capture one or more physiological signals related to a patient's temperature, such as a body core temperature. The processor 1302 can process the one or more physiological signals to measure the patient's body core temperature, which is a vital sign used by clinicians to monitor and manage patients' conditions. The temperature sensor 1318 can include a thermocouple, a temperature-measuring device having two dissimilar conductors or semiconductors that contact each other at one or more spots. A temperature differential can be experienced by the different conductors. The thermocouple can produce a voltage when the contact spot differs from a reference temperature. Thermocouples may be self-powered and therefore may not require an external power source for operation. In some embodiments, the temperature sensor 1318 can include a thermistor. A thermistor is a type of resistor whose resistance value can vary depending on its temperature. Thermistors typically offer a high degree of precision within a limited temperature range.

The acoustic respiration sensor 1320 may capture one or more physiological signals related to vibrational motion from the patient's body (e.g., the patient's chest) that are indicative of various physiologic parameters and/or conditions, including without limitation, heart rate, respiration rate, snoring, coughing, choking, wheezing, and respiratory obstruction (e.g., apneic events). Additional details regarding an example acoustic respiration sensor are described in U.S. patent application Ser. No. 12/643,939, filed Dec. 21, 2009, titled Acoustic Sensor Assembly, now issued as U.S. Pat. No. 8,771,204, which is hereby incorporated by reference in its entirety.

The electrocardiogram (ECG) sensor 1322 may capture one or more physiological signals related to cardiac activity. The processor 1302 can process the one or more physiological signals to measure the patient's cardiac activity. In some embodiments, the processor 1302 can process the ECG signal to detect arrhythmias, such as bradycardia, tachyarrhythmia, or ventricular fibrillation.

The oximetry sensor 1324 may capture one or more physiological signals related to pulse oximetry. The processor 1302 can process the one or more physiological signals to measure the patient's pulse oximetry, a widely accepted noninvasive procedure for measuring the oxygen saturation level of arterial blood, an indicator of a person's oxygen supply. Example oximetry sensor(s) 1324 include an optical sensor clipped onto a portion of the patient's body (such as, for example, a fingertip, an ear lobe, and/or a nostril). The processor 1302 can process the signals to measure the relative volume of oxygenated hemoglobin in pulsatile arterial blood flowing within the portion of the body being sensed, which includes measurements such as Oxygen saturation (SpO2), pulse rate, a plethysmograph waveform, perfusion index (PI), pleth variability index (PVi®), methemoglobin (MetHb), carboxyhemoglobin (CoHb), total hemoglobin (tHb), and/or glucose.

The temperature sensor 1318, acoustic respiration sensor 1320, ECG sensor 1322, and oximetry sensor 1324 are example sensors. Other physiological sensors 1330 may transmit physiological signals to the patient monitor 160 via the connectors 110 and 1120.

VII. Additional Embodiments and Terminology

While the present disclosure discusses example connectors in the medical device and/or patient monitoring context, the apparatuses, systems, and methods described herein may be agnostic to the particular context, and, therefore, may be used in any connector environment. Further, while the present disclosure discusses advantages of the example connectors as including water resistance, other embodiments of devices, apparatuses, systems, and/or methods described herein may not necessarily be water resistant and may have other advantages, as described herein.

Conditional language used herein, such as, among others, "can," "might," "may," "e.g.," "for example," and the like, unless specifically stated otherwise, or otherwise understood within the context as used, is generally intended to convey that certain embodiments include, while other embodiments do not include, certain features, elements, or states. Thus, such conditional language is not generally intended to imply that features, elements or states are in any way required for one or more embodiments.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Such disjunctive language is not generally intended to, and should not, imply that certain embodiments require at least one of X, at least one of Y, or at least one of Z to each be present. Thus, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

The term "a" as used herein should be given an inclusive rather than exclusive interpretation. For example, unless specifically noted, the term "a" should not be understood to mean "exactly one" or "one and only one"; instead, the term "a" means "one or more" or "at least one," whether used in the claims or elsewhere in the specification and regardless of uses of quantifiers such as "at least one," "one or more," or "a plurality" elsewhere in the claims or specification.

The terms "comprising," "including," "having," and the like are synonymous and are used inclusively, in an open-ended fashion, and do not exclude additional elements, features, acts, operations, and so forth.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments described herein can be embodied within a form that does not provide all of the features and benefits set forth herein, as some features can be used or practiced separately from others.

What is claimed is:

1. A water-resistant medical device cable assembly configured to interface one or more noninvasive physiological sensors with a patient monitor, the cable assembly comprising:
    a cable configured to connect to a physiological sensor, the cable comprising a plurality of conductors configured to obtain patient physiological signals; and
    a male connector attached to the cable and configured to couple the cable with a patient monitor so as to convey the patient physiological signals from the physiological sensor to the patient monitor, the male connector comprising:
    a rigid frame;
    a circuit board disposed within the rigid frame and connected with the conductors in the cable;
    a plurality of electrical contacts disposed on the circuit board, the plurality of electrical contacts operative to contact second electrical contacts in a corresponding female connector of the patient monitor when the male connector is inserted into the female connector; and
    a pliable overmold configured to cover a portion of the rigid frame and a portion of the circuit board but not the plurality of electrical contacts,
    wherein the plurality of electrical contacts are open to air when the male connector is disconnected from the female connector of the patient monitor,
    wherein the pliable overmold is further configured to create a seal with the female connector when the male connector is inserted into the female connector, such that when the male connector is inserted into the female connector, the plurality electrical contacts of the male connector are no longer exposed to air, such that a water-resistant seal is created between the male connector and the female connector,
    wherein the pliable overmold further comprises a first portion and a second portion, the first portion located between the plurality of electrical contacts and the second portion, the second portion adjacent to the cable, wherein a first width of a proximal end of the first portion is narrower than a second width of a distal end of the first portion, and wherein the first width being narrower than the second width reduces an insertion force to create the seal with the female connector when the male connector is inserted into the female connector.

2. The water-resistant medical device cable assembly of claim 1, further comprising:
    an inner covering configured to cover a portion of the cable, the inner covering is adjacent to the rigid frame and is located between the rigid frame and a distal end of the cable, wherein the inner covering is further configured to seal a distal end of the rigid frame and a proximal end of the cable, and wherein the pliable overmold is further configured to cover the inner covering.

3. The water-resistant medical device cable assembly of claim 1, wherein the first width is between approximately 2.03 centimeters and approximately 2.06 centimeters, and the second width is between approximately 2.06 centimeters and approximately 2.08 centimeters.

4. The water-resistant medical device cable assembly of claim 1, wherein the first width is between approximately 97% and approximately 98% of the second width.

5. The water-resistant medical device cable assembly of claim 1, further comprising a second connector attached to the cable.

6. The water-resistant medical device cable assembly of claim 5, wherein the second connector is a second female connector.

7. The water-resistant medical device cable assembly of claim 1, wherein the rigid frame comprises polycarbonate.

8. The water-resistant medical device cable assembly of claim 1, wherein the rigid frame comprises an insertion portion configured to be inserted into the female connector, the insertion portion comprises a detent configured to engage with a detent holder in the female connector.

9. The water-resistant medical device cable assembly of claim 8, wherein the insertion portion further comprises a second detent configured to engage with a second detent holder in the female connector.

10. The water-resistant medical device cable assembly of claim 1, wherein an angle between the proximal end and the distal end is between approximately 1 degree and approximately 2 degrees.

11. A water-resistant medical device cable assembly configured to interface with a patient monitor, the cable assembly comprising:
    a cable comprising a plurality of conductors; and
    a male connector attached to the cable and configured to couple the cable with a patient monitor, the male connector comprising:
    a rigid frame;
    a circuit board disposed within the rigid frame and connected with the conductors in the cable;
    a plurality of electrical contacts disposed on the circuit board, the plurality of electrical contacts operative to contact second electrical contacts in a corresponding female connector of the patient monitor when the male connector is inserted into the female connector; and
    a pliable overmold configured to cover a portion of the rigid frame and a portion of the circuit board but not the plurality of electrical contacts,
    wherein the plurality of electrical contacts are open to air when the male connector is disconnected from the female connector of the patient monitor,
    wherein the pliable overmold is further configured to create a seal with the female connector when the male connector is inserted into the female connector, such that when the male connector is inserted into the female connector, the plurality electrical contacts of the male connector are no longer exposed to air, such that a water-resistant seal is created between the male connector and the female connector, wherein the pliable overmold further comprises a first portion and a second portion, the first portion located between the plurality of electrical contacts and the second portion, the second portion adjacent to the cable, wherein a first width of a proximal end of the first portion is narrower than a second width of a distal end of the first portion, and wherein the first width being narrower than the second width reduces an insertion force to create the seal with the female connector when the male connector is inserted into the female connector.

12. The water-resistant medical device cable assembly of claim 11, further comprising:
   an inner covering configured to cover a portion of the cable, the inner covering is adjacent to the rigid frame and is located between the rigid frame and a distal end of the cable, wherein the inner covering is further configured to seal a distal end of the rigid frame and a proximal end of the cable, and wherein the pliable overmold is further configured to cover the inner covering.

13. The water-resistant medical device cable assembly of claim 11, wherein the first width is between approximately 2.03 centimeters and approximately 2.06 centimeters, and the second width is between approximately 2.06 centimeters and approximately 2.08 centimeters.

14. The water-resistant medical device cable assembly of claim 11, wherein the first width is between approximately 97% and approximately 98% of the second width.

15. The water-resistant medical device cable assembly of claim 11, further comprising a second connector attached to the cable.

16. The water-resistant medical device cable assembly of claim 15, wherein the second connector is a second female connector.

17. The water-resistant medical device cable assembly of claim 11, wherein the rigid frame comprises polycarbonate.

18. The water-resistant medical device cable assembly of claim 11, wherein the rigid frame comprises an insertion portion configured to be inserted into the female connector, the insertion portion comprises a detent configured to engage with a detent holder in the female connector.

19. The water-resistant medical device cable assembly of claim 18, wherein the insertion portion further comprises a second detent configured to engage with a second detent holder in the female connector.

20. The water-resistant medical device cable assembly of claim 11, wherein an angle between the proximal end and the distal end is between approximately 1 degree and approximately 2 degrees.

* * * * *